(12) United States Patent
Mizuki et al.

(10) Patent No.: US 9,997,719 B2
(45) Date of Patent: Jun. 12, 2018

(54) MATERIAL FOR ORGANIC ELECTROLUMINESCENCE DEVICE AND ORGANIC ELECTROLUMINESCENCE DEVICE

(71) Applicant: IDEMITSU KOSAN CO., LTD., Chiyoda-ku (JP)

(72) Inventors: Yumiko Mizuki, Sodegaura (JP); Nobuhiro Yabunouchi, Sodegaura (JP); Takushi Shiomi, Sodegaura (JP); Kazuki Nishimura, Sodegaura (JP); Mitsuru Eida, Sodegaura (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 732 days.

(21) Appl. No.: 14/039,539

(22) Filed: Sep. 27, 2013

(65) Prior Publication Data
US 2016/0104845 A1    Apr. 14, 2016

Related U.S. Application Data

(60) Provisional application No. 61/707,349, filed on Sep. 28, 2012.

(30) Foreign Application Priority Data

Sep. 28, 2012  (JP) .................................. 2012-217991

(51) Int. Cl.
H01L 51/50    (2006.01)
H01L 51/00    (2006.01)
(Continued)

(52) U.S. Cl.
CPC ........ *H01L 51/0072* (2013.01); *C07D 403/14* (2013.01); *C09K 11/025* (2013.01);
(Continued)

(58) Field of Classification Search
None
See application file for complete search history.

(56) References Cited

U.S. PATENT DOCUMENTS

2012/0223276 A1    9/2012  Parham et al.
2013/0056720 A1*   3/2013  Kim ..................... C07D 401/14
                                                     257/40
2013/0313536 A1   11/2013  Nishimura et al.

FOREIGN PATENT DOCUMENTS

WO    WO 2011/ 057706 A2    5/2011
WO    WO 2012/036482 A1    3/2012
(Continued)

OTHER PUBLICATIONS

International Search Report dated Dec. 10, 2013 in PCT/JP2013/076143 (with English language translation).

*Primary Examiner* — Gregory D Clark
(74) *Attorney, Agent, or Firm* — Oblon, McClelland, Maier & Neustadt, L.L.P.

(57) ABSTRACT

A material for organic electroluminescence device including a specific compound having a specific group in the central skeleton and an organic electroluminescence device including an organic thin film layer between an anode and a cathode. The organic thin film layer includes a light emitting layer and at least one layer of the organic thin film layer includes the material for organic electroluminescence device. The organic electroluminescence device has a long lifetime and the material for organic electroluminescence device realizes such a device.

19 Claims, 1 Drawing Sheet

(51) Int. Cl.
*C07D 403/14* (2006.01)
*C09K 11/06* (2006.01)
*H05B 33/14* (2006.01)
*C09K 11/02* (2006.01)

(52) U.S. Cl.
CPC .......... *C09K 11/06* (2013.01); *H01L 51/0067* (2013.01); *H01L 51/0085* (2013.01); *H05B 33/14* (2013.01); *C09K 2211/1007* (2013.01); *C09K 2211/1011* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *C09K 2211/185* (2013.01); *H01L 51/5016* (2013.01)

(56) References Cited

FOREIGN PATENT DOCUMENTS

| WO | WO 2012/087007 A1 | 6/2012 |
| WO | WO 2012/121561 A1 | 9/2012 |
| WO | WO 2012/134124 A1 | 10/2012 |
| WO | WO 2013/073874 A1 | 5/2013 |
| WO | WO 2013/085243 A1 | 6/2013 |
| WO | WO 2013/162284 A1 | 10/2013 |

* cited by examiner

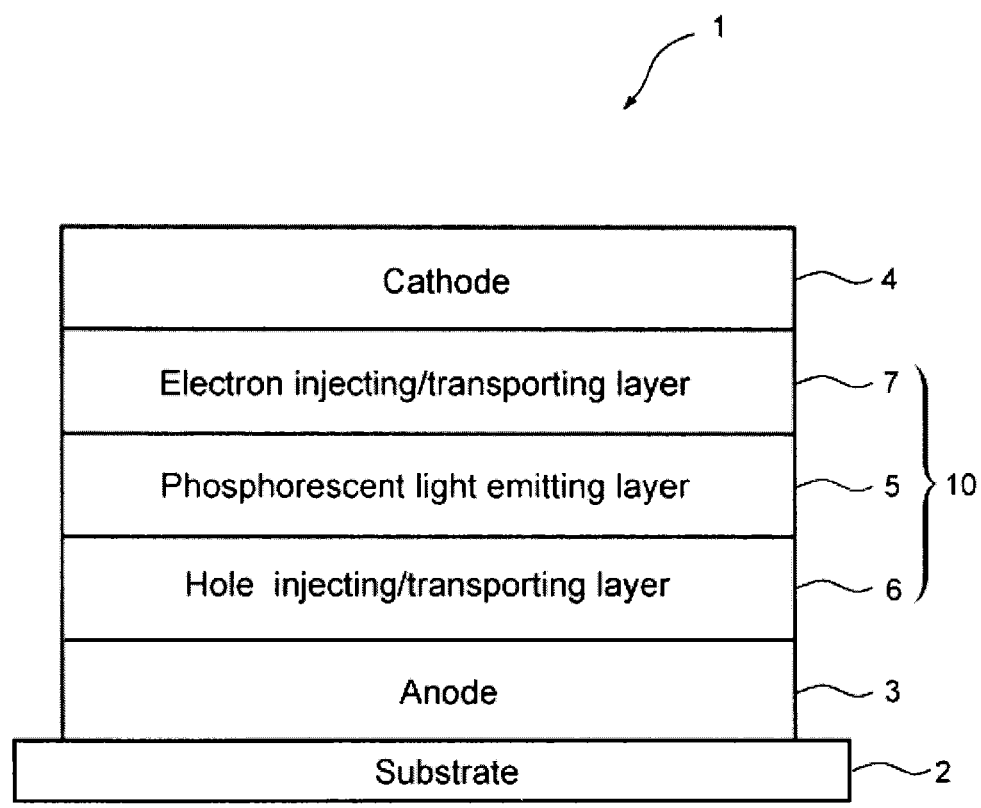

MATERIAL FOR ORGANIC ELECTROLUMINESCENCE DEVICE AND ORGANIC ELECTROLUMINESCENCE DEVICE

TECHNICAL FIELD

The present invention relates to materials for organic electroluminescence devices and organic electroluminescence devices employing the materials.

BACKGROUND ART

By applying voltage to an organic electroluminescence device (also referred to as "organic EL device"), holes from an anode and electrons from a cathode are injected into a light emitting layer. The holes and electrons injected into the light emitting layer recombine to form excitons. The singlet exciton and the triplet exciton are formed at a ratio of 25%:75% according to spin-statistics theorem. Since the fluorescence is the emission from singlet excitons, it has been known that the internal quantum efficiency of a fluorescent organic EL device is limited to 25%. In contrast, since the phosphorescence is the emission from triplet excitons, it has been known that the internal quantum efficiency of a phosphorescent organic EL device can be increased to 100% if the intersystem crossing occurs efficiently.

In the development of known organic EL devices, an optimum device design has been made depending upon the emission mechanism such as fluorescence and phosphorescence. It has been known in the art that a high-performance phosphorescent organic EL device cannot be obtained by a mere application of the fluorescent technique to the phosphorescent device, because the emission mechanisms are different from each other. This may be generally because the following reasons.

Since the phosphorescence is the emission from triplet excitons, a compound with larger energy gap is required to be used in the light emitting layer. This is because that the singlet energy (energy difference between the lowest excited singlet state and the ground state) of a compound is generally larger than its triplet energy (energy difference between the lowest excited triplet state and the ground state).

Therefore, to effectively confine the triplet energy of a phosphorescent dopant material within a device, a host material having triplet energy larger than that of the phosphorescent dopant material should be used in the light emitting layer. In addition, if an electron transporting layer and a hole transporting layer is formed adjacent to the light emitting layer, a compound having triplet energy larger than that of the phosphorescent dopant material should be used also in the electron transporting layer and the hole transporting layer. Thus, the device design conventionally employed for developing a phosphorescent organic EL device results in the use of a compound having an energy gap larger than that of a compound for use in a fluorescent organic EL device, thereby increasing the voltage for driving an organic EL device.

A hydrocarbon compound highly resistant to oxidation and reduction, which has been known as a useful compound for a fluorescent device, has a small energy gap because of a broad distribution of π-electron cloud. Therefore, such a hydrocarbon compound is not suitable for use in a phosphorescent organic EL device and, instead, an organic compound having a heteroatom, such as oxygen and nitrogen, has been selected. However, a phosphorescent organic EL device employing such an organic compound having a heteroatom has a shorter lifetime as compared with a fluorescent organic EL device.

In addition, a phosphorescent dopant material has an extremely longer relaxation time of triplet excitons as compared with that of its singlet excitons, this largely affecting the device performance. Namely, in the emission from singlet excitons, since the relaxation speed which leads to emission is high, the diffusion of excitons into a layer adjacent to the light emitting layer (for example, a hole transporting layer and an electron transporting layer) is difficult to occur and efficient emission is expected. In contrast, the emission from triplet excitons is a spin-forbidden transition and the relaxation speed is low. Therefore, the diffusion of excitons into adjacent layers occurs easily and the thermal energy deactivation occurs in most compounds other than the specific phosphorescent compound. Thus, as compared with a fluorescent organic EL device, it is more important for a phosphorescent organic EL device to control the region for recombining electrons and holes.

For the above reasons, the development of a high performance phosphorescent organic EL device requires the selection of materials and the consideration of device design which are different from those for a fluorescent organic EL device.

A carbazole derivative having a high triplet energy and a carbazole skeleton known as a principal skeleton of hole transporting materials has been conventionally used as a useful phosphorescent host material.

Patent Document 1 describes, as a material for organic EL device, a compound in which a nitrogen-containing heterocyclic group is introduced into a biscarbazole skeleton which includes two carbazole structures connected to each other. The compound described in Patent Document 1 is molecularly designed to balance the charge transport by introducing an electron-deficient nitrogen-containing heterocyclic group to a hole transporting carbazole skeleton. Patent Document 2 describes that the charge injecting ability of a N,N-biscarbazole compound wherein two carbazole structures are bonded to each other via a biphenyl group is improved by introducing an electron-withdrawing group into the intervening biphenyl group between two carbazole structures.

However, the improvement of the lifetime of the proposed organic EL devices is still required and the development of a new material for organic EL device which realizes a longer lifetime has been demanded.

PRIOR ART DOCUMENTS

Patent Documents

Patent Document 1: WO 2011/132684
Patent Document 2: JP 2011-176258A

SUMMARY OF THE INVENTION

Problem to be Solved by the Invention

An object of the present invention is to provide a material for organic EL device which realizes a long-lifetime organic EL device and such an organic EL device.

Means for Solving Problem

As a result of extensive study for achieving the above object, the inventors have found that an organic EL device having a longer lifetime than before can be obtained by using a material for organic EL device represented by formula (I) mentioned below, wherein a substituent X selected from (i) an electron-withdrawing group, (ii) a group wherein a value of a substituent constant (σp (para)) of Hammett equation is positive, or (iii) an electron-withdrawing group wherein a value of a substituent constant (σp (para)) of Hammett equation is positive is bonded to a specific position of a central skeleton.

The present invention provides:

1 to 3. A material for organic electroluminescence device represented by formula (I):

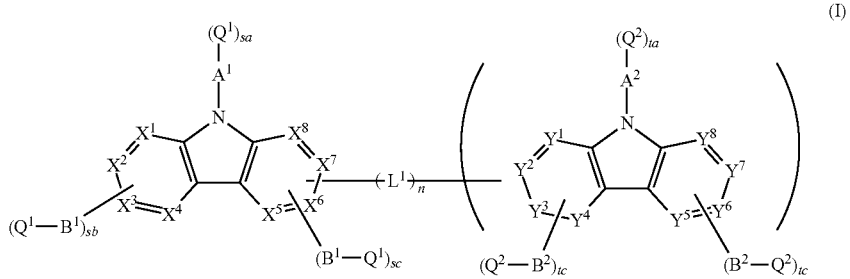

wherein:
each of $A^1$ and $A^2$ independently represents a single bond, a substituted or unsubstituted aromatic hydrocarbon group having 6 to 30 ring carbon atoms, or a substituted or unsubstituted heterocyclic group having 5 to 30 ring atoms;

each of $B^1$ and $B^2$ independently represents a single bond, a substituted or unsubstituted divalent aromatic hydrocarbon group having 6 to 30 ring carbon atoms, or a substituted or unsubstituted divalent heterocyclic group having 5 to 30 ring atoms;

each of $X^1$ to $X^8$ and $Y^1$ to $Y^8$ independently represents N (nitrogen group) or $CR^a$ (C: carbon group), provided that when adjacent two of $X^1$ to $X^8$ and $Y^1$ to $Y^8$ are both $CR^a$, $R^a$ groups in adjacent $CR^a$ groups may be bonded to each other to form a ring;

$R^a$ independently represents a hydrogen atom, a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted silyl group, or a halogen atom, and when two or more $R^a$ groups exist, the $R^a$ groups may be the same or different;

$L^1$ represents a single bond, a substituted or unsubstituted divalent aromatic hydrocarbon group having 6 to 30 ring carbon atoms, or a substituted or unsubstituted divalent heterocyclic group having 5 to 30 ring atoms;

n represents an integer of 0 to 3, provided that when n=0, $L^1$ represents a single bond, and one of $X^5$ to $X^8$ is directly bonded to one of $Y^1$ to $Y^8$ and $A^2$;

one of $X^5$ to $X^8$ is bonded to one of $Y^1$ to $Y^8$ and $A^2$ via $L^1$ or directly;

each of sa and ta independently represents an integer of 0 to 5, each of sb, tb and tc independently represents an integer of 0 to 4, and sc represents an integer of 0 to 3, provided that sa+sb+sc+ta+tb+tc represents an integer of 1 to 5;

when sa represents 1 to 5, $A^1$ is boned to $Q^1$ of $(Q^1)_{sa}$;

when sb represents 1 to 4, at least one of $X^1$ to $X^4$ is bonded to $B^1$ of $(B^1\text{-}Q^1)_{sb}$ or $Q^1$ when $B^1$ represents a single bond;

when sc represents 1 to 3, at least one of $X^5$ to $X^8$ is bonded to $B^1$ of $(B^1\text{-}Q^1)_{sc}$ or $Q^1$ when $B^1$ represents a single bond;

when ta represents 1 to 5, $A^2$ is bonded to $Q^2$ of $(Q^2)_{ta}$;

when tb represents 1 to 4, at least one of $Y^5$ to $Y^8$ is bonded to $B^2$ of $(B^2\text{-}Q^2)_{tb}$ or $Q^2$ when $B^2$ represents a single bond;

when tc represents 1 to 4, at least one of $Y^1$ to $Y^4$ is bonded to $B^2$ of $(B^2\text{-}Q^2)_{tc}$ or $Q^2$ when $B^2$ represents a single bond;

each of $Q^1$ and $Q^2$ independently represents $\text{-Az-W}_q$;

q represents an integer of 1 to 4;

when two or more $Q^1$ groups exist, the $Q^1$ groups may be the same or different, and when two or more $Q^2$ groups exist, the $Q^2$ groups may be the same or different;

Az represents a q+1 valent residue of a ring represented by formula (Z):

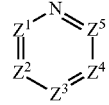

wherein:
each of $Z^1$ to $Z^5$ independently represents a nitrogen group or $CR^b$, wherein $R^b$ is as defined above with respect to $R^a$, provided that when adjacent two of $Z^1$ to $Z^5$ are both $CR^b$, $R^b$ groups of adjacent $CR^b$ groups may be boned to each other to form a ring;

when two or more $R^b$ groups exist, the $R^b$ groups may be the same or different;

when two or more Az groups exist, the Az groups may be the same or different;

W represents a substituent X, a non-fused aromatic hydrocarbon group having 6 to 15 ring carbon atoms substituted with a substituent X, a fused aromatic hydrocarbon group having 12 to 30 ring carbon atoms substituted with a substituent X, or a heterocyclic group having 5 to 30 ring atoms substituted with a substituent X, provided that the aromatic hydrocarbon group having 6 to 15 ring carbon atoms substituted with a substituent X, the fused aromatic hydrocarbon group having 12 to 30 ring carbon atoms substituted with a substituent X, and the heterocyclic group having 5 to 30 ring atoms substituted with a substituent X may have a substituent other than the substituent X;

when two or more W groups exist, the W groups may be the same or different; and the substituent X represents (i) an electron-withdrawing group, (ii) a group wherein a value of a substituent constant (σp (para)) of Hammett equation is positive, or (iii) an electron-withdrawing group wherein a value of a substituent constant (σp (para)) of Hammett equation is positive, provided that the substituent X cannot be a cyano group:

4. The material for organic electroluminescence device according to any one of items 1 to 3, wherein the material is represented by formula (II):

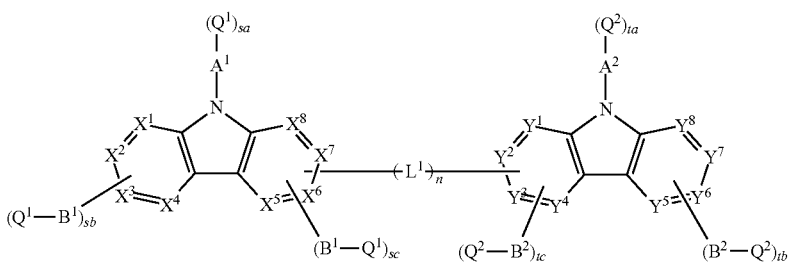
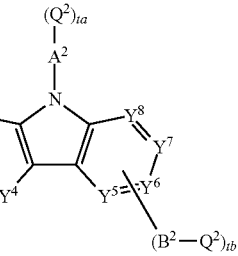

(II)

wherein:

$A^1$, $A^2$, $B^1$, $B^2$, $X^1$ to $X^8$, $Y^1$ to $Y^8$, $L^1$, n, sa, sb, sc, ta, tb, $Q^1$, and $Q^2$ are as defined above;

tc represents an integer of 0 to 3;

sa+sb+sc+ta+tb+tc represents an integer of 1 to 5; and one of $X^5$ to $X^8$ is bonded to one of $Y^1$ to $Y^4$ via $L^1$ or directly;

5. The material for organic electroluminescence device according to any one of items 1 to 4, wherein the material is represented by formula (III):

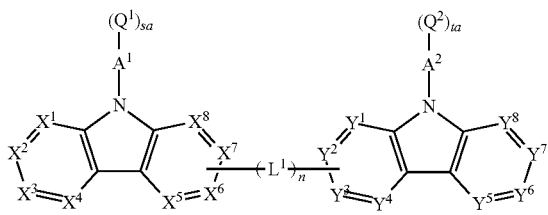

(III)

wherein:

$A^1$, $A^2$, $X^1$ to $X^8$, $Y^1$ to $Y^8$, $L^1$, n, $Q^1$, and $Q^2$ are as defined above;

each of sa and ta independently represents an integer of 0 to 5;

sa+ta represents an integer of 1 to 5; and one of $X^5$ to $X^8$ is bonded to one of $Y^1$ to $Y^4$ via $L^1$ or directly;

6. The material for organic electroluminescence device according to any one of items 1 to 5, wherein $X^7$ is bonded to $Y^3$ via $L^1$ or directly;

7. The material for organic electroluminescence device according to any one of items 1 to 5, wherein $X^6$ is bonded to $Y^2$ via $L^1$ or directly;

8. The material for organic electroluminescence device according to any one of items 1 to 5, wherein $X^6$ is bonded to $Y^3$ via $L^1$ or directly;

9. The material for organic electroluminescence device according to any one of items 1 to 8, wherein Az represents a q+1 valent residue of a ring selected from the group consisting of a substituted or unsubstituted pyrimidine ring, a substituted or unsubstituted triazine ring, and a substituted or unsubstituted pyridine ring;

10. The material for organic electroluminescence device according to any one of items 1 to 9, wherein $L^1$ represents a phenylene group when n=1 to 3 or a single bond when n=0;

11. The material for organic electroluminescence device according to any one of items 1 to 10, wherein the non-fused aromatic hydrocarbon group for W which represents the non-fused aromatic hydrocarbon group having 6 to 15 ring carbon atoms substituted with a substituent X is selected from a phenyl group and a biphenyl group;

12. The material for organic electroluminescence device according to any one of items 1 to 11, wherein the non-fused aromatic hydrocarbon group for W which represents the non-fused aromatic hydrocarbon group having 6 to 15 ring carbon atoms substituted with a substituent X is a phenylene group, and Az and the substituent X are in a para-relationship;

13. The material for organic electroluminescence device according to any one of items 1 to 10, wherein the fused aromatic hydrocarbon group for W which represents the fused aromatic hydrocarbon group having 12 to 30 ring carbon atoms substituted with a substituent X is selected from the group consisting of a naphthyl group, a phenanthrenyl group, a triphenylenyl group, a fluorenyl group, and a spirobifluorenyl group;

14. The material for organic electroluminescence device according to any one of items 1 to 10, wherein the heterocyclic group for W which represents the heterocyclic group having 5 to 30 ring atoms substituted with a substituent X is selected from a dibenzofuranyl group and a dibenzothiophenyl group;

15. The material for organic electroluminescence device according to any one of items 1 to 14, wherein the substituent X for W is selected from the group consisting of —F, —Cl, —Br, —I, —$CO_2R^C$, —$COR^C$, —$CF_3$, —$SO_2R^C$, and —$NO_2$, wherein $R^C$ independently represents a hydrogen atom, a substituted or unsubstituted aromatic hydrocarbon group having 6 to 30 ring carbon atoms, a substituted or unsubstituted heterocyclic group having 5 to 30 ring atoms, and a substituted or unsubstituted alkyl group having 1 to 30 carbon atoms;

16. The material for organic electroluminescence device according to any one of items 1 to 15, wherein the substituent X for W is selected from the group consisting of —F, —$CF_3$, —$CO_2R^C$, —$COR^C$, and —$SO_2R^C$;

17. The material for organic electroluminescence device according to any one of items 1 to 15, wherein the substituent X for W is —F;

18. The material for organic electroluminescence device according to any one of items 1 to 10, wherein W is a F-substituted phenyl group, a F-substituted biphenyl group, a F-substituted 9,9-dimethylfluorenyl group, a F-substituted dibenzofuranyl group, or a F-substituted dibenzothiophenyl group;

19. The material for organic electroluminescence device according to any one of items 1 to 4, wherein each of sa, sb, sc, ta, tb, and tc represents 0 or 1;

20. The material for organic electroluminescence device according to any one of items 1 to 4, wherein each of ta, tb and tc represents 0;

21. The material for organic electroluminescence device according to any one of items 1 to 4, wherein sa+sb+sc+ta+tb+tc represents 1;

22. The material for organic electroluminescence device according to any one of items 1 to 21, wherein q represents an integer of 2 to 4;

23. An organic electroluminescence device comprising one or more organic thin film layers between a cathode and an anode, wherein the organic thin film layers comprises a light emitting layer and at least one layer of the organic thin film layers comprises the material for organic electroluminescence device according to any one of items 1 to 22;

24. The organic electroluminescence device according to item 23, wherein the light emitting layer comprises the material for organic electroluminescence device; and 25. The organic electroluminescence device according to item 23 or 24, wherein the light emitting layer comprises a phosphorescent emitting material selected from an ortho-metallated complex of a metal selected from iridium (Ir), osmium (Os), and platinum (Pt).

Effect of the Invention

According to the present invention, a long-lifetime organic EL device with a high emission efficiency and an organic EL material which realizes such a device are provided.

BRIEF DESCRIPTION OF DRAWINGS

FIG. 1 is a schematic cross-sectional view of an exemplified organic EL device of the invention.

MODE FOR CARRYING OUT THE INVENTION

Material for Organic Electroluminescence Device

The material for organic electroluminescence device (hereinafter also referred to as "material for organic EL device") of the invention is represented by formula (I):

In formula (I):

each of $A^1$ and $A^2$ independently represents a single bond, a substituted or unsubstituted aromatic hydrocarbon group having 6 to 30 ring carbon atoms, or a substituted or unsubstituted heterocyclic group having 5 to 30 ring atoms.

Each of $B^1$ and $B^2$ independently represents a single bond, a substituted or unsubstituted divalent aromatic hydrocarbon group having 6 to 30 ring carbon atoms, or a substituted or unsubstituted divalent heterocyclic group having 5 to 30 ring atoms.

Each of $X^1$ to $X^8$ and $Y^1$ to $Y^8$ independently represents N (nitrogen group) or $CR^a$ (C: carbon group). When adjacent two of $X^1$ to $X^8$ and $Y^1$ to $Y^8$ are both $CR^a$, $R^a$ groups in adjacent two $CR^a$ groups may be bonded to each other to form a ring. $R^a$ independently represents a hydrogen atom, a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted silyl group, or a halogen atom.

When two or more $R^a$ groups exist, the $R^a$ groups may be the same or different.

$L^1$ represents a single bond, a substituted or unsubstituted divalent aromatic hydrocarbon group having 6 to 30 ring carbon atoms, or a substituted or unsubstituted divalent heterocyclic group having 5 to 30 ring atoms.

The subscript n represents an integer of 0 to 3, provided that when n=0, $L^1$ represents a single bond, and one of $X^5$ to $X^8$ is directly bonded to one of $Y^1$ to $Y^8$ and $A^2$.

One of $X^5$ to $X^8$ is bonded to one of $Y^1$ to $Y^8$ and $A^2$ via $L^1$ or directly.

Each of sa and ta independently represents an integer of 0 to 5, each of sb, tb and tc independently represents an integer of 0 to 4, and sc represents an integer of 0 to 3, provided that sa+sb+sc+ta+tb+tc represents an integer of 1 to 5.

When sa represents 1 to 5, $A^1$ is boned to $Q^1$ of $(Q^1)_{sa}$. When sb represents 1 to 4, at least one of $X^1$ to $X^4$ is bonded to $B^1$ of $(B^1\text{-}Q^1)_{sb}$ or bonded to $Q^1$ when $B^1$ represents a single bond. When sc represents 1 to 3, at least one of $X^5$ to $X^8$ is bonded to $B^1$ of $(B^1\text{-}Q^1)_{sc}$ or bonded to $Q^1$ when $B^1$ represents a single bond.

When ta represents 1 to 5, $A^2$ is bonded to $Q^2$ of $(Q^2)_{ta}$. When tb represents 1 to 4, at least one of $Y^5$ to $Y^8$ is bonded to $B^2$ of $(B^2\text{-}Q^2)_{tb}$ or bonded to $Q^2$ when $B^2$ represents a single bond. When tc represents 1 to 4, at least one of $Y^1$ to $Y^4$ is bonded to $B^2$ of $(B^2\text{-}Q^2)_{tc}$ or bonded to $Q^2$ when $B^2$ represents a single bond.

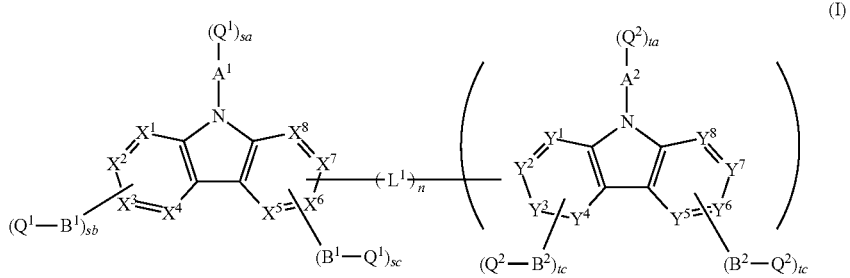

(I)

Each of $Q^1$ and $Q^2$ independently represents $\text{-Az-W}_q$, wherein q represents an integer of 1 to 4.

When two or more $Q^1$ groups exist, the $Q^1$ groups may be the same or different, and when two or more $Q^2$ groups exist, the $Q^2$ groups may be the same or different.

Az represents a q+1 valent residue of a ring represented by formula (Z):

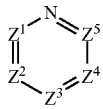
(Z)

wherein:
each of $Z^1$ to $Z^5$ independently represents a nitrogen group or $CR^b$, wherein $R^b$ is as defined above with respect to $R^a$, provided that when adjacent two of $Z^1$ to $Z^5$ are both $CR^b$, $R^b$ groups of in the adjacent two $CR^b$ groups may be boned to each other to form a ring; and when two or more $R^b$ groups exist, the $R^b$ groups may be the same or different.

When two or more Az groups exist, the Az groups may be the same or different.

W represents a substituent X, a non-fused aromatic hydrocarbon group having 6 to 15 ring carbon atoms substituted with a X-substituted, a fused aromatic hydrocarbon group having 12 to 30 ring carbon atoms substituted with a X-substituted, or a heterocyclic group having 5 to 30 ring atoms substituted with a X-substituted, provided that the aromatic hydrocarbon group having 6 to 15 ring carbon atoms substituted with a X-substituted, the fused aromatic hydrocarbon group having 12 to 30 ring carbon atoms substituted with a X-substituted, and the heterocyclic group having 5 to 30 ring atoms substituted with a X-substituted may have a substituent other than the substituent X. The substituent X represents (i) an electron-withdrawing group, (ii) a group wherein a value of a substituent constant (σp (para)) of Hammett equation is positive, or (iii) an electron-withdrawing group wherein a value of a substituent constant (σp (para)) of Hammett equation is positive, provided that the substituent X cannot be a cyano group. When two or more W groups exist, the W groups may be the same or different.

The material for organic EL device represented by formula (I) is preferably represented by formula (II):

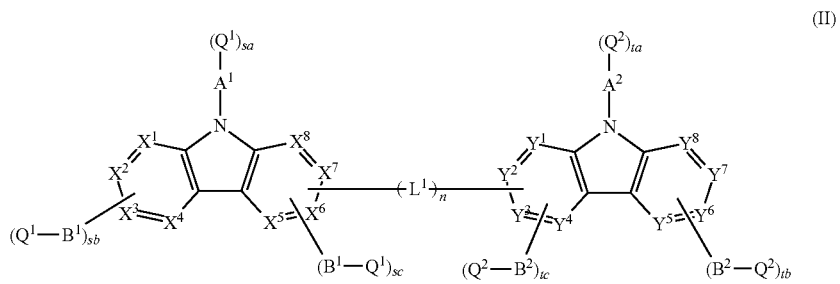
(II)

wherein:
$A^1$, $A^2$, $B^1$, $B^2$, $X^1$ to $X^8$, $Y^1$ to $Y^8$, $L^1$, n, sa, sb, sc, ta, tb, $Q^1$, and $Q^2$ are as defined above;
tc represents an integer of 0 to 3;
sa+sb+sc+ta+tb+tc represents an integer of 1 to 5; and
one of $X^5$ to $X^8$ is bonded to one of $Y^1$ to $Y^4$ via $L^1$ or directly.

The bonding between one of $X^5$ to $X^8$ and one of $Y^1$ to $Y^4$ via $L^1$ or directly is represented, for example, by $X^6$-$(L^1)_n$-$Y^3$, $X^6$-$(L^1)_n$-$Y^2$, $X^6$-$(L^1)_n$-$Y^1$, $X^6$-$(L^1)_n$-$Y^4$, $X^7$-$(L^1)_n$-$Y^3$, $X^7$-$(L^1)_n$-$Y^2$, $X^7$-$(L^1)_n$-$Y^1$, $X^7$-$(L^1)_n$-$Y^4$, $X^5$-$(L^1)_n$-$Y^3$, $X^5$-$(L^1)_n$-$Y^2$, $X^5$-$(L^1)_n$-$Y^1$, $X^5$-$(L^1)_n$-$Y^4$, $X^8$-$(L^1)_n$-$Y^3$, $X^8$-$(L^1)_n$-$Y^2$, $X^8$-$(L^1)_n$-$Y^1$, and $X^8$-$(L^1)_n$-$Y^4$.

The material for organic EL device represented by formula (I) is more preferably represented by formula (II-1):

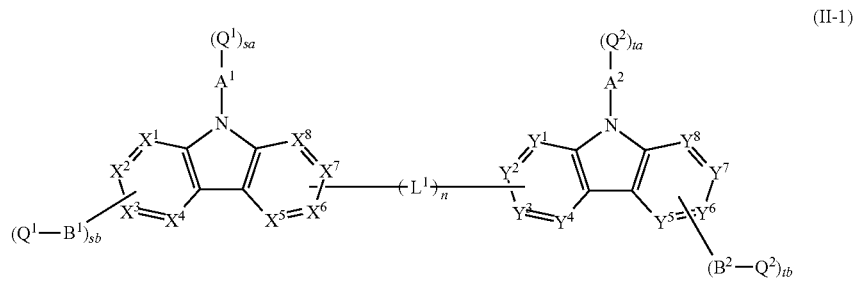
(II-1)

wherein:

$A^1$, $A^2$, $B^1$, $B^2$, $X^1$ to $X^8$, $Y^1$ to $Y^8$, $L^1$, n, sa, sb, ta, tb, $Q^1$, and $Q^2$ are as defined above; and one of $X^5$ to $X^8$ is bonded to one of $Y^1$ to $Y^4$ via $L^1$ or directly.

The material for organic EL device represented by formula (I) is more preferably represented by formula (III):

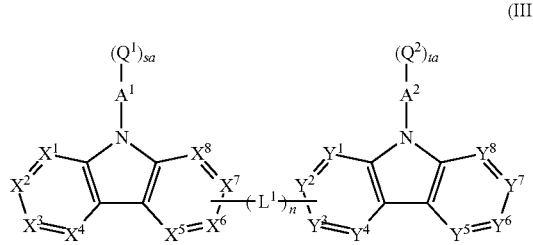

(III)

wherein:

$A^1$, $A^2$, $X^1$ to $X^8$, $Y^1$ to $Y^8$, $L^1$, n, $Q^1$, and $Q^2$ are as defined above;

each of sa and ta independently represents an integer of 0 to 5;

sa+ta represents an integer of 1 to 5; and one of $X^5$ to $X^8$ is bonded to one of $Y^1$ to $Y^4$ via $L^1$ or directly.

In a preferred embodiment of formulae (I) to (III), $X^7$ and $Y^3$ are bonded to each other via $L^1$ or directly, $X^6$ and $Y^2$ are bonded to each other via $L^1$ or directly, or $X^6$ and $Y^3$ are bonded to each other via $L^1$ or directly, for example, as shown in formulae (I-1) to (I-3):

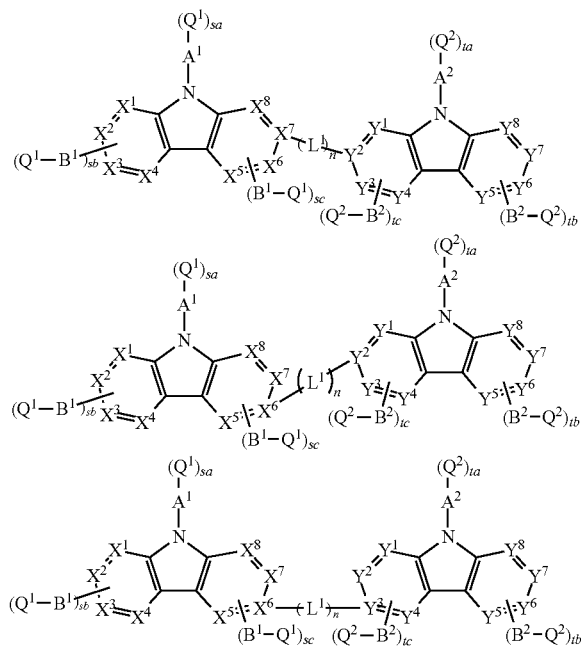

wherein $A^1$, $A^2$, $B^1$, $B^2$, $X^1$ to $X^8$, $Y^1$ to $Y^8$ $L^1$, n, sa, sb, sc, ta, tb, tc, $Q^1$, and $Q^2$ are as defined in formula (I).

Each of the groups in formulae (I) to (III), formula (II-1), and formulae (I-1) to (I-3) are described below in detail.

The aromatic hydrocarbon group having 6 to 30, preferably 6 to 14 ring carbon atoms for $A^1$, $A^2$, $R^a$, and $R^b$ may include a non-fused aromatic hydrocarbon group and a fused aromatic hydrocarbon group. Specific examples thereof include a phenyl group, a naphthyl group, a phenanthryl group, a biphenyl group, a terphenyl group, a quaterphenyl group, a fluoranthenyl group, a triphenylenyl group, a phenanthrenyl group, a fluorenyl group, a spirofluorenyl group, a 9,9-diphenylfluorenyl group, a 9,9'-spirobi[9H-fluorene]-2-yl group, a 9,9-dimethylfluorenyl group, a benzo[c]phenanthrenyl group, a benzo[a]triphenylenyl group, a naphtho[1,2-c]phenanthrenyl group, a naphtho[1,2-a]triphenylenyl group, a dibenzo[a,c]triphenylenyl group, and a benzo[b]fluoranthenyl group, with a phenyl group, a naphthyl group, a biphenyl group, a terphenyl group, a phenanthryl group, a triphenylenyl group, a fluorenyl group, a spirobifluorenyl group, and a fluoranthenyl group being preferred.

Examples of the divalent aromatic hydrocarbon group having 6 to 30 ring carbon atoms for $L^1$, $B^1$ and $B^2$ include divalent residues of the aromatic hydrocarbon groups described above with respect to $A^1$, $A^2$, $R^a$, and $R^b$, with a phenylene group, a biphenylene group, and a naphthylene group being preferred.

The heterocyclic group having 5 to 30, preferably 5 to 14 ring atoms for $A^1$, $A^2$, $R^a$ and $R^b$ may include a non-fused heterocyclic group or a fused heterocyclic group. Specific examples thereof include the residues of a pyrrole ring, an isoindole ring, a benzofuran ring, an isobenzofuran ring, a dibenzothiophene ring, an isoquinoline ring, a quinoxaline ring, a phenanthridine ring, a phenanthroline ring, a pyridine ring, a pyrazine ring, a pyrimidine ring, a pyridazine ring, a triazine ring, an indole ring, a quinoline ring, an acridine ring, a pyrrolidine ring, a dioxane ring, a piperidine ring, a morpholine ring, a piperazine ring, a carbazole ring, a furan ring, a thiophene ring, an oxazole ring, an oxadiazole ring, a benzoxazole ring, a thiazole ring, a thiadiazole ring, a benzothiazole ring, a triazole ring, an imidazole ring, a benzimidazole ring, a pyran ring, a dibenzofuran ring, and a benzo[c]dibenzofuran ring, and the residues of derivatives of these rings, with the residues of a dibenzofuran ring, a carbazole ring, a dibenzothiophene ring, and derivatives of these rings being preferred.

Examples of the divalent heterocyclic group having 5 to 30 ring atoms represented by $L^1$, $B^1$ and $B^2$ include divalent residues of the heterocyclic groups described above with respect to $A^1$, $A^2$, $R^a$, and $R^b$, with a dibenzofuranylene group and a dibenzothiophenylene group being preferred.

Examples of the alkyl group having 1 to 30, preferably 1 to 6 carbon atoms for $R^a$ and $R^b$ include a methyl group, an ethyl group, a n-propyl group, an isopropyl group, a n-butyl group, a s-butyl group, an isobutyl group, a t-butyl group, a n-pentyl group, a n-hexyl group, a n-heptyl group, a n-octyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a neopentyl group, a 1-methylpentyl group, a cyclopropyl group, a cyclobutyl group, a cyclopentyl group, a cyclohexyl group, a cyclooctyl group, and an adamantyl group, with a methyl group, an ethyl group, a n-propyl group, an isopropyl group, a n-butyl group, a s-butyl group, an isobutyl group, a t-butyl group, a cyclopentyl group, and a cyclohexyl group being preferred.

Examples of the substituted or unsubstituted silyl group for $R^a$ and $R^b$ include a trimethylsilyl group, a triethylsilyl group, a tributylsilyl group, a dimethylethylsilyl group, a t-butyldimethylsilyl group, a vinyldimethylsilyl group, a propyldimethylsilyl group, a dimethylisopropylsilyl group, a dimethylpropylsilyl group, a dimethylbutylsilyl group, a dimethyltertiarybutylsilyl group, a diethylisopropylsilyl group, a phenyldimethylsilyl group, a diphenylmethylsilyl group, a diphenyltertiarybutylsilyl group, and a triphenylsilyl group, with a trimethylsilyl group, a triethylsilyl group, a t-butyldimethylsilyl group, a vinyldimethylsilyl group, and a propyldimethylsilyl group being preferred.

Examples of the halogen atom for R$^a$ and R$^b$ include fluorine, chlorine, bromine, and iodine, with fluorine being preferred.

When sa and/or to is 1 or more, each of A$^1$ and A$^2$ is preferably selected so as to balance the carrier transporting abilities of the compound. Such a selection of A$^1$ and A$^2$ is also effective when the compound of the invention is used in the light emitting layer as the host material.

Each of A$^1$ and A$^2$ is preferably a single bond or a substituted or unsubstituted phenyl group, more preferably a single bond or a phenyl group.

Examples of the optional substituent indicated by "substituted or unsubstituted" referred to above or hereinafter include a halogen atom (fluorine, chlorine, bromine, iodine), a cyano group, an alkyl group having 1 to 20, preferably 1 to 6 carbon atoms, a cycloalkyl group having 3 to 20, preferably 5 to 12 carbon atoms, an alkoxyl group having 1 to 20, preferably 1 to 5 carbon atoms, a haloalkyl group having 1 to 20, preferably 1 to 5 carbon atoms, a haloalkoxyl group having 1 to 20, preferably 1 to 5 carbon atoms, an alkylsilyl group having 1 to 10, preferably 1 to 5 carbon atoms, an aryl group having 6 to 30, preferably 6 to 18 ring carbon atoms, an aryloxy group having 6 to 30, preferably 6 to 18 ring carbon atoms, an arylsilyl group having 6 to 30, preferably 6 to 18 carbon atoms, an aralkyl group having 7 to 30, preferably 7 to 20 carbon atoms, and a heteroaryl group having 5 to 30, preferably 5 to 18 ring atoms. Examples thereof include those as mentioned above with respect to R$^a$, with a fluorine atom, an alkyl group, a cycloalkyl group, an alkylsilyl group, an aryl group (aromatic hydrocarbon group), and a heteroaryl group (heterocyclic group) being particularly preferred. These groups may be further substituted with the optional substituent mentioned above.

The carbon number "a to b" in the expression of "a substituted or unsubstituted XX group having a to b carbon atoms" referred to herein is the carbon number of the unsubstituted XX group and does not include the carbon atom of the optional substituent.

The hydrogen atom referred to herein includes isotopes different from neutron numbers, i.e., light hydrogen (protium), heavy hydrogen (deuterium) and tritium. This definition equally applies to any of the hydrogen atoms present in the compounds of the invention.

Each of Q$^1$ and Q$^2$ independently represents -Az-W$_q$, wherein q represents an integer of 1 to 4, preferably an integer of 2 to 4 because the effect of the substituent X in W is further enhanced.

Az represents a q+1 valent residue of a ring represented by formula (Z).

In formula (Z), R$^b$ groups in adjacent CR$^b$ groups may be bonded to each other to form a ring. Examples of such a ring to be optionally formed include the rings corresponding to the aromatic hydrocarbon ring groups and the heterocyclic groups as mentioned above with respect to A$^1$, A$^2$, R$^a$, and R$^b$.

Examples of the q+1 valent residue of the ring represented by formula (Z) for Az include q+1 valent residues of an isoquinoline ring, a quinoxaline ring, phenanthridine ring, a phenanthroline ring, a pyridine ring, a pyrazine ring, a pyrimidine ring, a pyridazine ring, a triazine ring, a quinazoline ring, a quinoline ring, and an acridine ring. These rings may be substituted or unsubstituted. Preferred are q+1 valent residues of a pyrimidine ring, a triazine ring, a pyridine ring, a quinazoline ring, and a phenanthroline ring.

Az is particularly preferably a q+1 valent residue of a substituted or unsubstituted pyrimidine ring, a substituted or unsubstituted triazine ring, or a substituted or unsubstituted pyridine ring.

The substituent for the ring represented by formula (Z) is preferably an alkyl group having 1 to 30 carbon atoms, an alkoxy group having 1 to 30 carbon atoms, a haloalkyl group having 1 to 30 carbon atoms, a haloalkoxy group, a silyl group, an aromatic hydrocarbon group having 6 to 30 ring carbon atoms, or a heterocyclic group having 5 to 30 ring atoms.

Examples of the alkyl group, silyl group, aromatic hydrocarbon group, and heterocyclic group include those as mentioned above with respect to A$^1$, A$^2$, R$^a$ and R$^b$.

Examples of the haloalkyl group include the alkyl groups mentioned above wherein at least one hydrogen atom is substituted with a halogen atom, preferably a fluorine atom. Preferred are a trifluoromethyl group and a 2,2-trifluoroethyl group.

Examples of the alkoxy group include a methoxy group, a propoxy group, pentyloxy group, and a hexyloxy group. Examples of the haloalkoxy group include the alkoxy groups mentioned above wherein at least one hydrogen atom is substituted with a halogen atom, preferably a fluorine atom.

Examples of Q$^1$ and Q$^2$ are shown below.

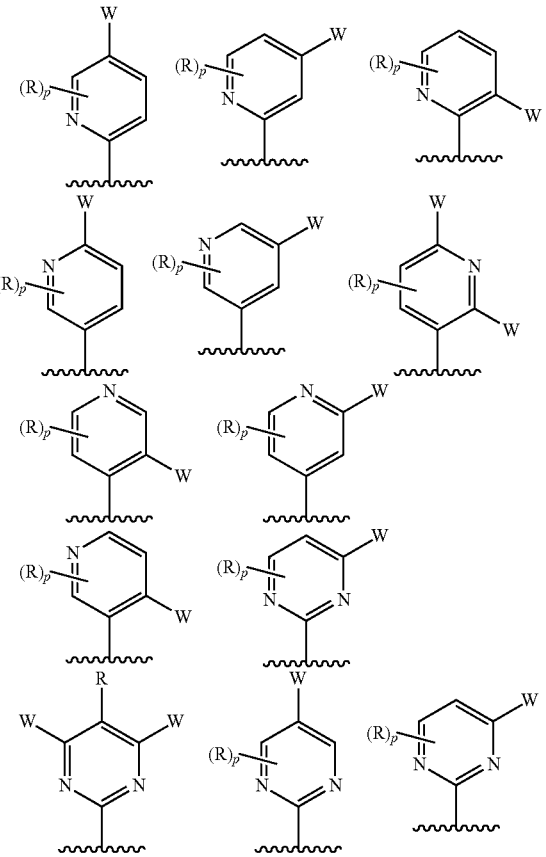

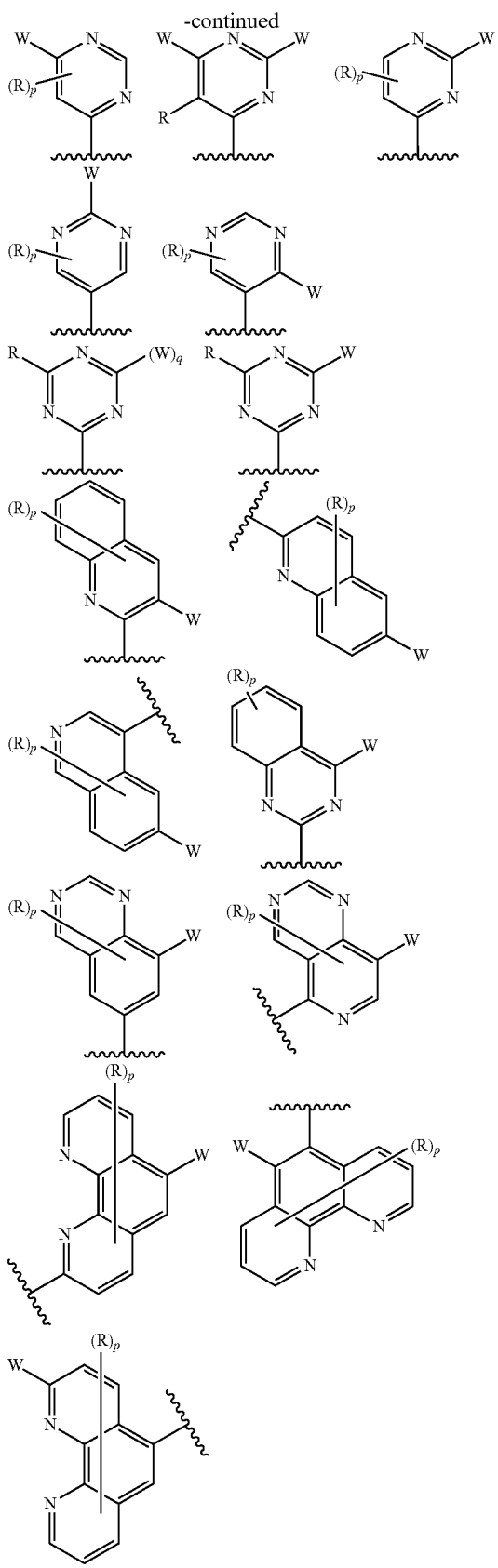

In the above formulae, each R represents a substituent which is defined as mentioned above with respect to $R^a$ and $R^b$. R is preferably a substituted or unsubstituted phenyl group, a substituted or unsubstituted biphenyl group, a substituted or unsubstituted fluorenyl group, a substituted or unsubstituted naphthyl group, a substituted or unsubstituted dibenzofuranyl group, or a substituted or unsubstituted thiophenyl group.

W is as defined above and p represents an integer of 1 to 5.

W represents a substituent X, a non-fused aromatic hydrocarbon group having 6 to 15 ring carbon atoms substituted with a substituent X, a fused aromatic hydrocarbon group having 12 to 30 ring carbon atoms substituted with a substituent X, or a heterocyclic group having 5 to 30 ring atoms substituted with a substituent X. The aromatic hydrocarbon group having 6 to 15 ring carbon atoms substituted with a substituent X, the fused aromatic hydrocarbon group having 12 to 30 ring carbon atoms substituted with a substituent X, and the heterocyclic group having 5 to 30 ring atoms substituted with a substituent X may have a substituent other than the substituent X. When two or more W groups exist, the W groups may be the same or different.

The number of the substituent X is 1 to 5, preferably 1 to 2, and more preferably 1.

The substituent X represents (i) an electron-withdrawing group, (ii) a group wherein a value of a substituent constant (σp (para)) of Hammett equation is positive, or (iii) an electron-withdrawing group wherein a value of a substituent constant (σp (para)) of Hammett equation is positive. However, the substituent X cannot be a cyano group.

The electron-withdrawing group, otherwise called an electron-accepting group, in the definition of the substituent X is known in the electronic theory as an atom or a group of atoms that withdraws electrons from another group of atoms to which it is attached by the inductive effect or the resonance effect.

The substituent X also includes a group wherein the value of a substituent constant (σp (para)) of Hammett equation is positive. Although the substituent constant (σp (para)) of phenyl group may be positive, the substituent X referred to herein does not include a phenyl group.

Examples of the substituent include —F (σp: +0.06), —Cl (σp: +0.23), —Br (σp: +0.23), —I (σp: +0.18), —CO$_2$R$^C$ (σp: +0.45 when R is Et), —COR$^C$ (σp: +0.50 when R is Me), —CF$_3$ (σp: +0.54), —SO$_2$R$^C$ (σp:+0.72 when R is Me), and —NO$_2$ (σp: +0.78).

The values of the substituent constant (σp (para)) of Hammett equation are described, for example, in Rikagaku Jiten, 5th ed.; Iwanami Shoten, Publishers: p 1063 and Hitomi Suzuki, Organic Reaction II Aromatic Compound, Organic Chemistry Course 2, p 119.

$R^C$ independently represents a hydrogen atom, a substituted or unsubstituted aromatic hydrocarbon group having 6 to 30 ring carbon atoms, a substituted or unsubstituted heterocyclic group having 5 to 30 ring atoms, or a substituted or unsubstituted alkyl group having 1 to 30 carbon atoms. Examples thereof are the same as those mentioned above with respect to $R^a$ and $R^b$.

The substituent X is preferably —F, —CF$_3$, —COR$^C$, or —SO$_2$R$^C$ in view of its chemical stability (hardly decomposed) or electrical stability (hardly generate radicals), and more preferably —F because the molecular weight of the resultant compound is low to reduce the deposition temperature and increase the heat stability.

In the compound of the invention, the azine ring represented by formula (Z) is substituted with W which represents a non-fused or fused aromatic hydrocarbon group substituted with the substituent X, a heterocyclic group substituted with the substituent X, or the substituent X. By the inductive effect of the substituent X, Af (electron affinity) of a compound wherein the azine ring is bonded to the specific position of its structure (particularly, a host material) is increased. Therefore, the electron barrier to the hole transporting layer is increased and the electrons are confined to decrease the deterioration of the hole injecting/transporting layer due to electrons, thereby improving the lifetime of organic EL device.

Particularly, when the substituent X is —F, since the triplet level of the host is maintained high if being substituted, the lifetime of organic EL device is improved.

When W is a non-fused aromatic hydrocarbon group having 6 to 15 ring carbon atoms substituted with the substituent X, the electron-withdrawing effect of the substituent X is sufficiently exhibited. Therefore, the resultant compound has a low molecular weight to reduce the vapor deposition temperature, thereby prevent the heat deterioration of the material. If the number of ring carbon atoms exceeds 15, since the substituent X is away from the azine (Az) ring, the electron-withdrawing effect becomes insufficient. In addition, the resultant compound has a higher molecular weight to increase the vapor deposition temperature, thereby likely to cause the heat deterioration of the material.

The non-fused aromatic hydrocarbon group having 6 to 15 ring carbon atoms is preferably a phenyl group and a biphenyl group.

In a preferred embodiment of the invention, the non-fused aromatic hydrocarbon group having 6 to 15 ring carbon atoms for W is a phenylene group and the substituent X is bonded at the para-position with respect to Az.

If satisfying the above conditions, the triplet level is high to improve the lifetime of organic EL device and make the compound effective for use in an organic EL device which emits short wavelength light, such as green light and bluish green light. When the substituent X is bonded at the meta-position, the triplet level is lowered to fail to improve the lifetime of organic EL device and limit the emission color of applicable organic EL device in some cases. When the substituent X is bonded at the ortho-position, the steric hindrance between the substituent X and Az is large, thereby likely to make the synthesis of the compound difficult or adversely affect the lifetime of organic EL device due to increased amount of impurities.

When W represents a fused aromatic hydrocarbon group having 12 to 30 ring carbon atoms substituted with a substituent X, the resonance effect with the substituent X is enhanced to moderately narrower the energy gap (singlet level) of the compound. Therefore, the material is structurally stabilized (photo-excitation stability) to effectively prolong the lifetime of organic EL device. If the number of ring carbon atoms exceeds 30, the energy gap (singlet level) of the resultant compound is made excessively narrow and the triplet level is made lower, to limit the emission color of applicable organic EL device. In addition, the substituent X is away from the azine (Az) ring to make the effect of the substituent X (inductive effect) insufficient and the resultant compound has a higher molecular weight to increase the vapor deposition temperature, thereby likely to cause the heat deterioration of the material.

Examples of the fused aromatic hydrocarbon group having 12 to 30 ring carbon atoms for W include a naphthyl group, a phenanthryl group, a fluoranthenyl group, a triphenylenyl group, a phenanthrenyl group, a fluorenyl group, a spirofluorenyl group, a 9,9-diphenylfluorenyl group, a 9,9'-supirobi[9H-fluorene]-2-yl group, a 9,9-dimethylfluorenyl group, a benzo[c]phenanthrenyl group, a benzo[a]triphenylenyl group, a naphtho[1,2-c]phenanthrenyl group, a naphtho[1,2-a]triphenylenyl group, a dibenzo[a,c]triphenylenyl group, and a benzo[b]fluoranthenyl, with a naphthyl group, a phenanthryl group, a triphenylenyl group, a fluorenyl group, and a spirobifluorenyl group being preferred.

When W represents a heterocyclic group having 5 to 30 ring atoms substituted with a substituent X, the triplet level is high to maintain or improve the efficiency of organic EL device and to make the compound effective for use in an organic EL device which emits short wavelength light, such as green light and bluish green light.

Preferred examples of the heterocyclic group having 5 to 30 ring atoms for W include a dibenzothiophenyl group and a dibenzofuranyl group.

The non-fused aromatic hydrocarbon group having 6 to 15 ring carbon atoms, the fused aromatic hydrocarbon group having 12 to 30 ring carbon atoms, and the heterocyclic group having 5 to 30 ring atoms for W may have a substituent other than the substituent X. Examples of the substituent other than the substituent X are those mentioned above with respect to the optional substituent of "substituted or unsubstituted."

W is preferably a F-substituted phenyl group, a F-substituted biphenyl group, a F-substituted 9,9-dimethylfluorenyl group, a F-substituted a dibenzofuranyl group, or a F-substituted dibenzothiophenyl group, because the triplet energy level tends to be high, thereby improving the lifetime of an organic EL device comprising such compound in the light emitting layer.

$L^1$ preferably represents a single bond, a substituted or unsubstituted divalent monocyclic hydrocarbon group having 6 ring carbon atoms, or a substituted or unsubstituted divalent hetero monocyclic group having 6 or less ring atoms. With such $L^1$, the distortion between the rings represented by formulae (a) and (b) (for example, carbazole rings and azacarbazole rings, which may be collectively referred to as "carbazole derivative") is minimized to make it easy to retain the conjugation of π-electrons. This allows HOMO (highest occupied molecular orbital) to extend throughout the whole biscarbazole skeleton formed by two carbazole derivatives, thereby to retain the hole injecting/transporting ability of the carbazole skeleton. In more preferred embodiment, $L^1$ is a phenylene group (n=1 to 3) or a single bond (n=0).

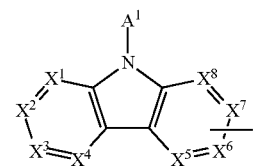

(a)

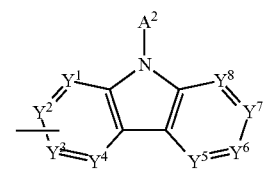

(b)

Each of sa, sb, sc, ta, tb, and tc is preferably 0 or 1, and each of ta, tb and tc is more preferably 0.

The sum of sa+sb+sc+ta+tb+tc is preferably 1.

The material for organic EL device of the invention comprises a hole transporting biscarbazole skeleton into which an electron transporting unit $Q^1$-$B^1$ and/or $Q^2$-$B^2$ (cyano group-containing azine ring) is introduced. Each of $Q^1$-$B^1$ and $Q^2$-$B^2$ includes -Az-$W_q$, wherein W represented by (i), (ii) or (iii) each including the substituent X is introduced into the azine ring Az. Therefore, the carrier balance in the molecule is good and the lifetime of an organic EL device employing the material is prolonged.

In a preferred embodiment of the material for organic EL device of the invention, the electron transporting unit $Q^1$-$B^1$ and/or $Q^2$-$B^2$ is preferably introduced into the terminal end of the biscarbazole skeleton. When introduced into the terminal end of the biscarbazole skeleton, the distribution of HOMO (distribution of π electron cloud) of the biscarbazole skeleton which acts as a hole transporting unit is kept broad, thereby allowing the biscarbazole skeleton to have a good hole transporting ability. In addition, the hole injecting/transporting carbazole skeleton and the electron injecting/transporting cyano group-containing group do not counteract each other's properties. Therefore, the carrier balance in the molecule is good and the lifetime of an organic EL device employing the material is prolonged.

In contrast, in the compound described in Patent Document 2, the distribution of HOMO on the biscarbazole skeleton is narrowed to decrease the hole transporting ability, because the electron-accepting cyano group is introduced into the linking group between two carbazole structures. Therefore, as compared with the material for organic EL device of the invention, the compound described in Patent Document 2 tends to lose the carrier balance in its molecule.

As compared with the nitrogen-containing heteroring having no group such as the substituent X, for example, the pyrimidine ring and triazine ring described in Patent Document 1, the azine ring derivatives comprising the substituent X in $Q^1$-$B^1$ and $Q^2$-$B^2$ tend to be more resistant to holes. Therefore, as compared with the organic EL device which employs the compound described in Patent Document 1, the organic EL device which employs the inventive material for organic EL device comprising the X-containing azine ring has a longer lifetime.

The production method of the material for organic EL device is not particularly limited and the material is produced according to a known method, for example, by a coupling reaction between a carbazole derivative and an aromatic halogenated compound in the presence of a copper catalyst described in Tetrahedron, 40 (1984), 1435 to 1456 or a palladium catalyst described in Journal of American Chemical Society, 123 (2001), 7727 to 7729.

Specific examples of the material for organic EL device of the invention are shown below, although not limited to the following compounds.

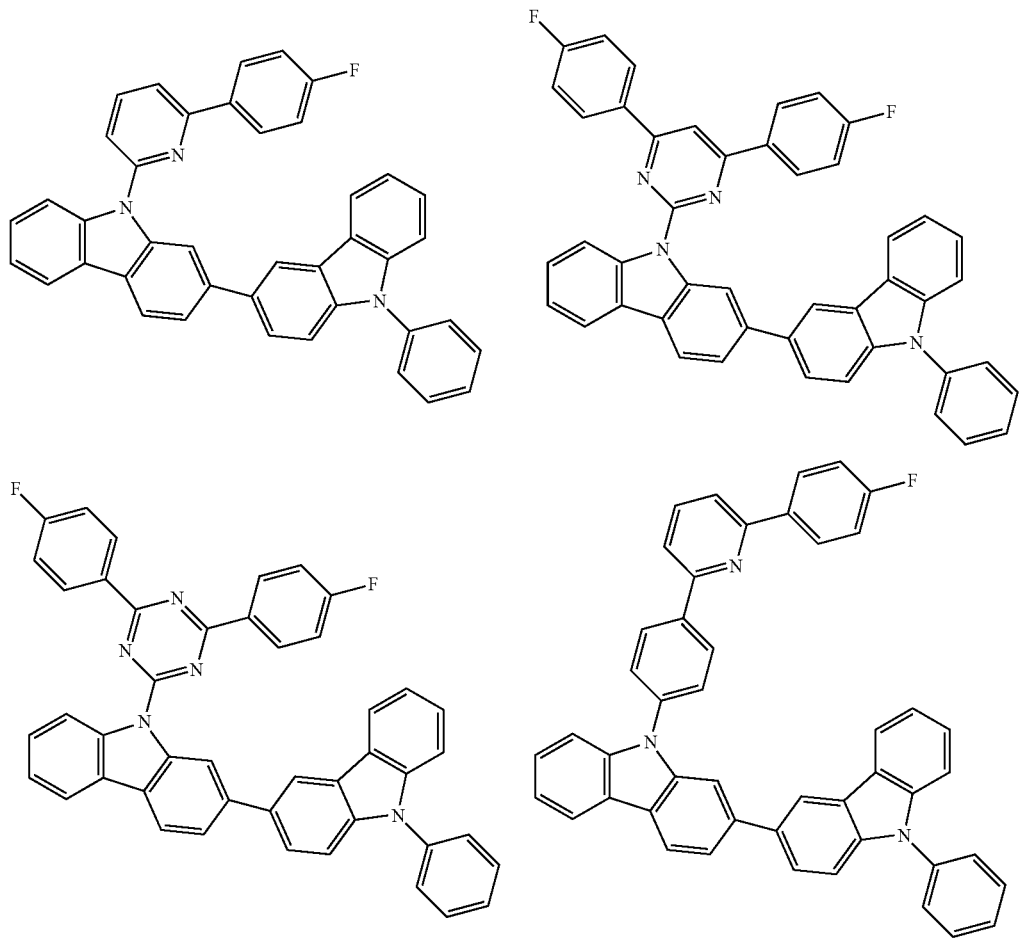

-continued
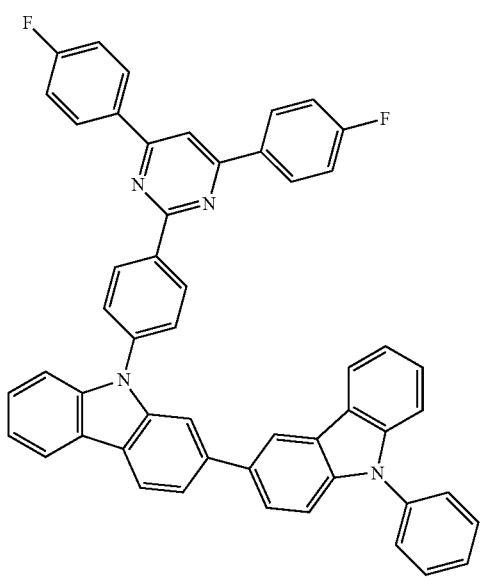
21
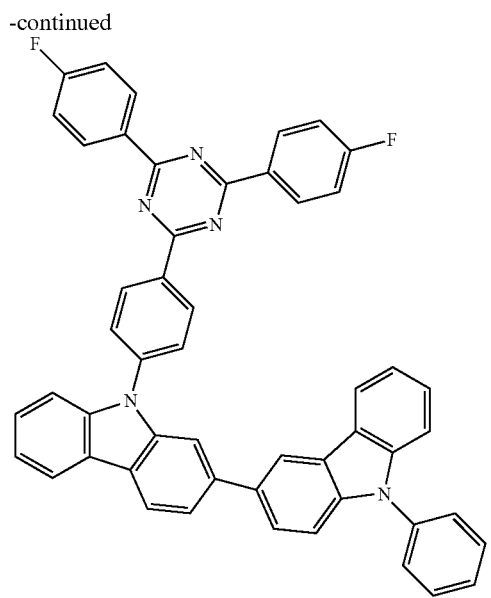
22
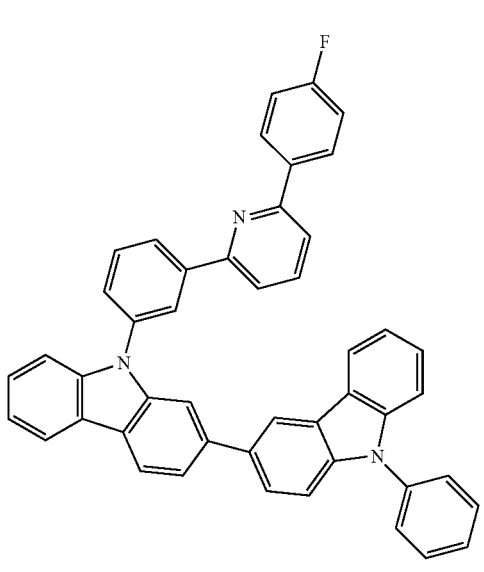
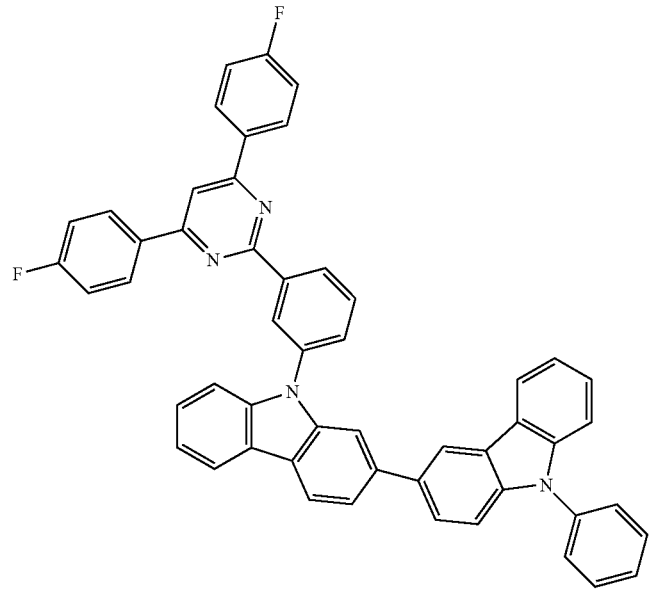

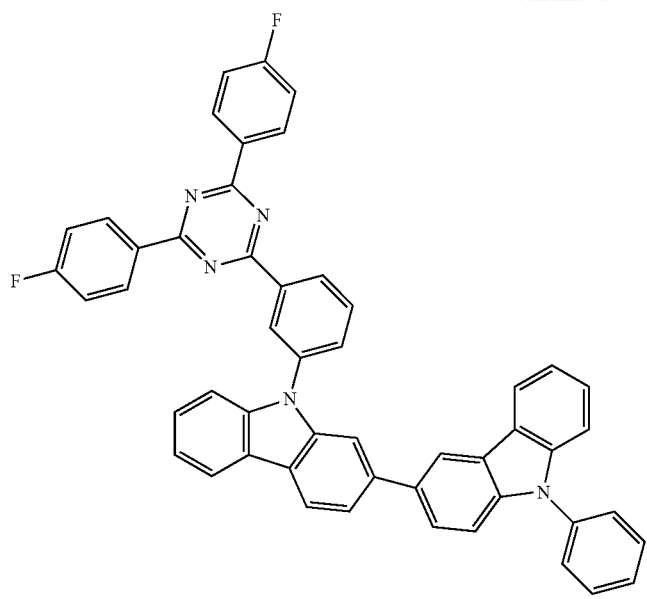
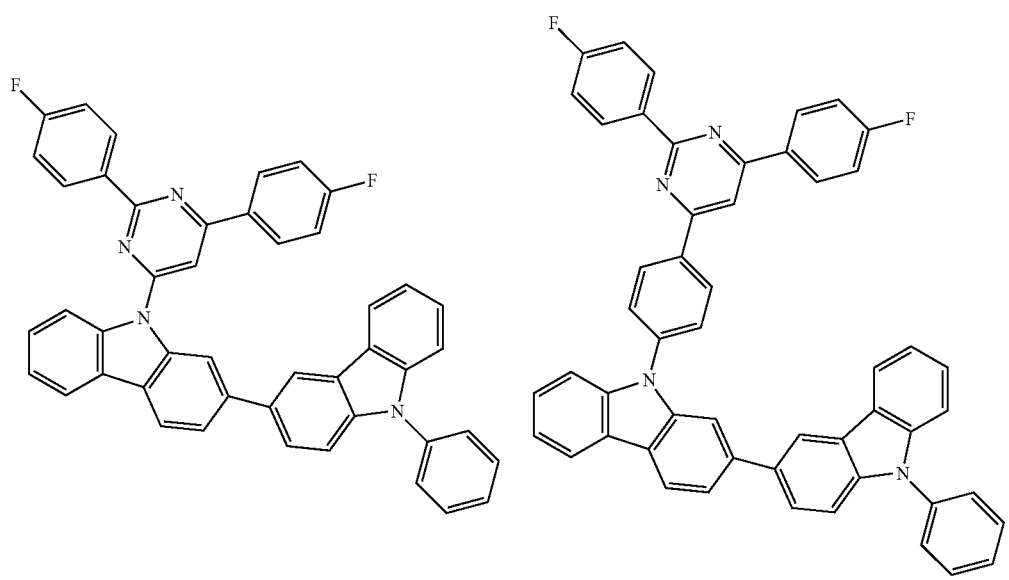

-continued
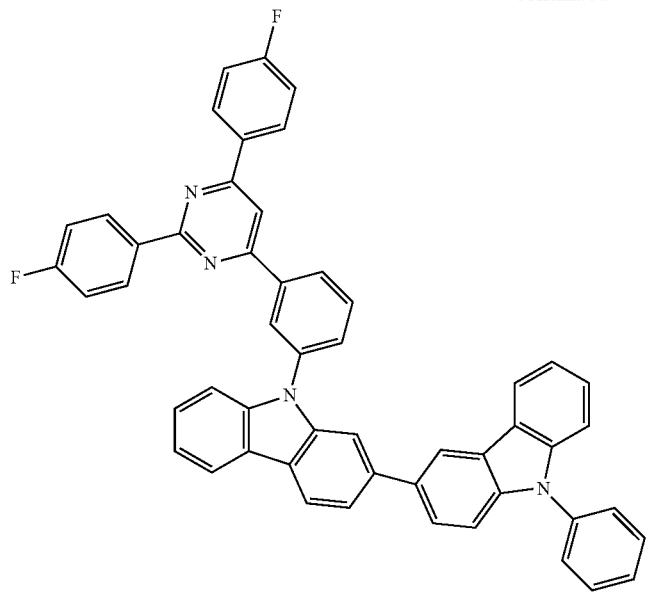
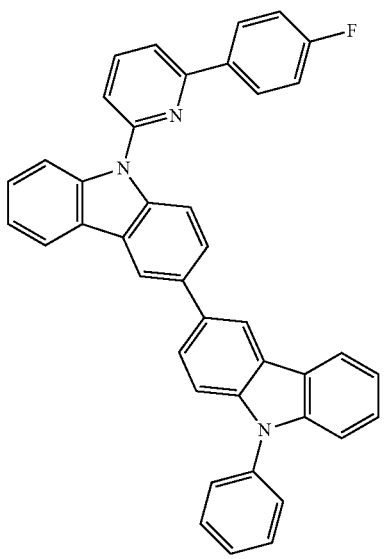
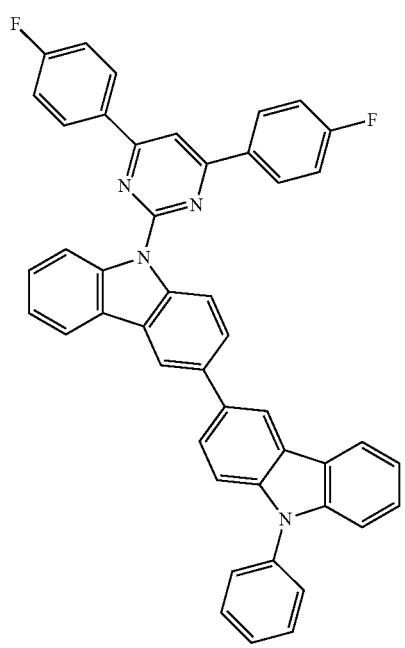
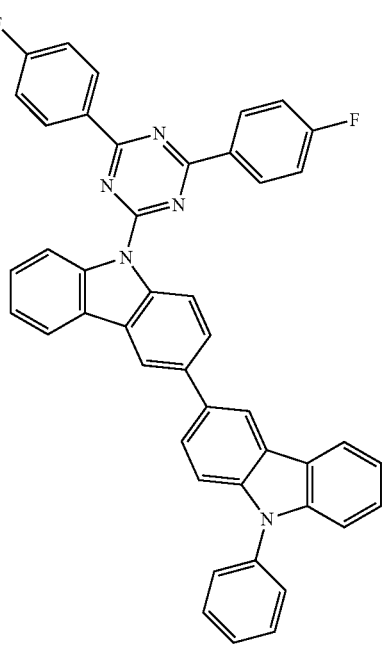

-continued
27
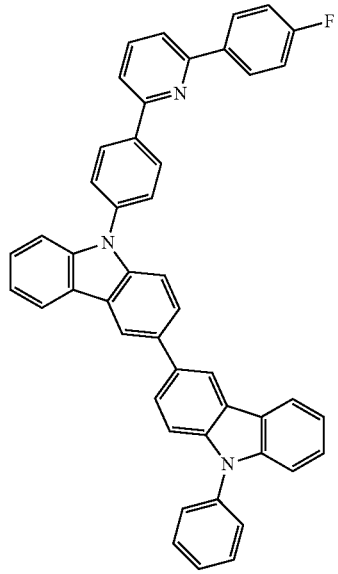
28
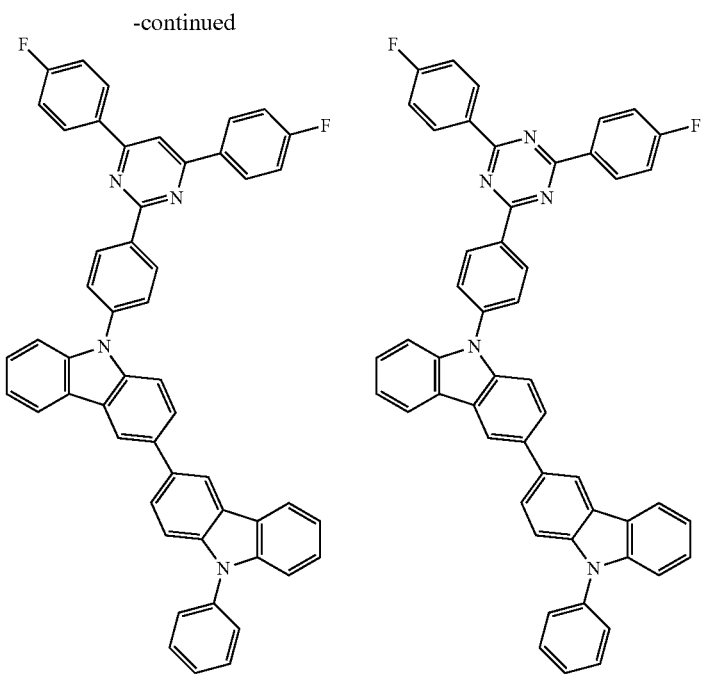
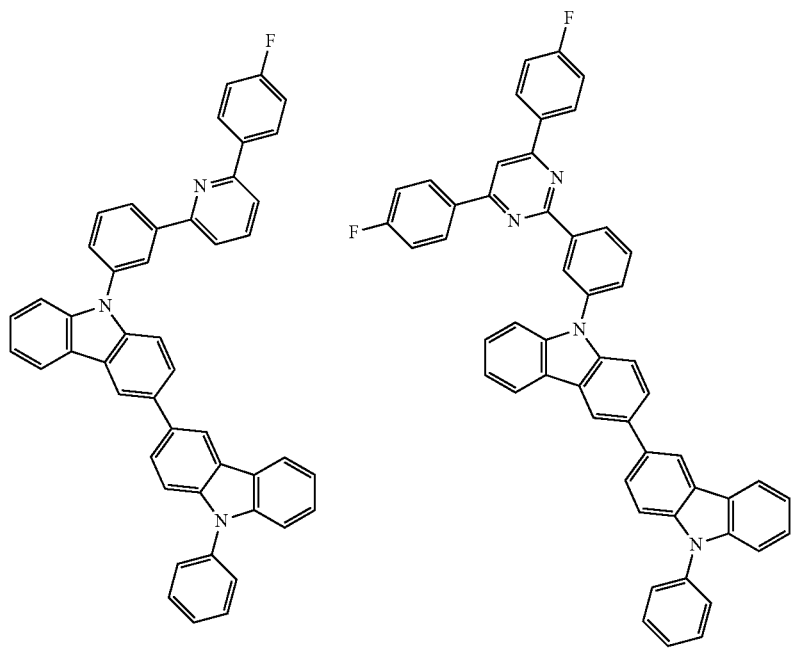

-continued
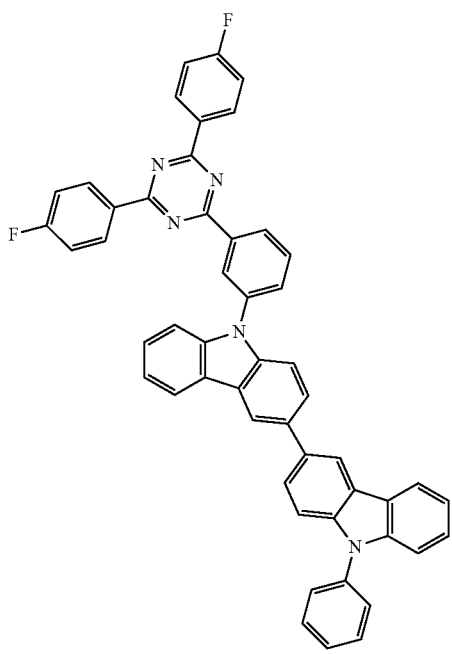
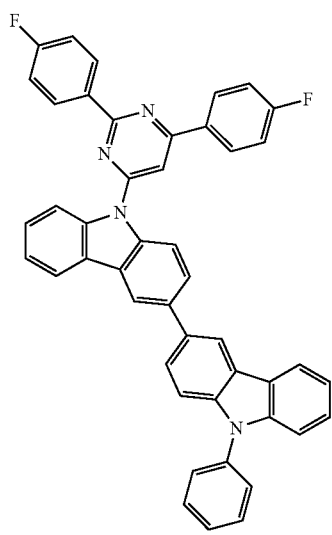
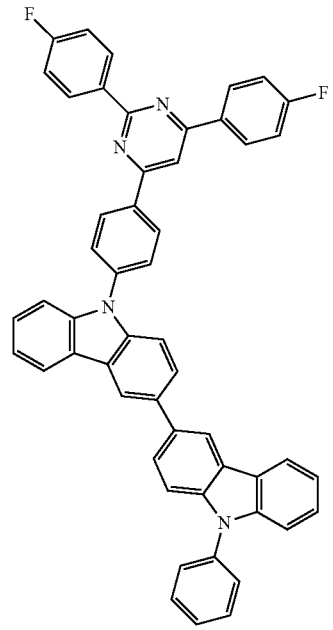
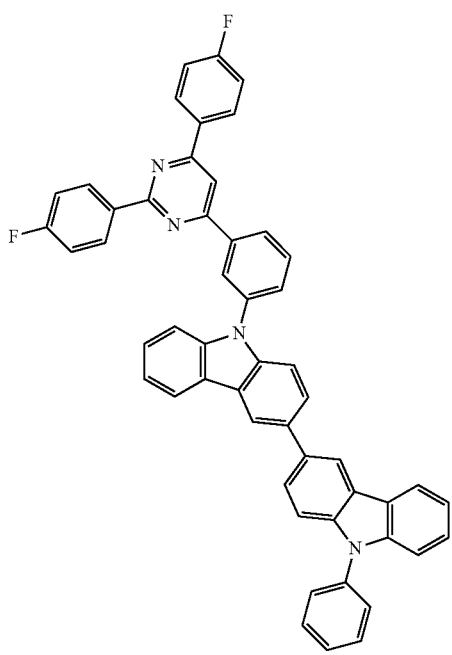
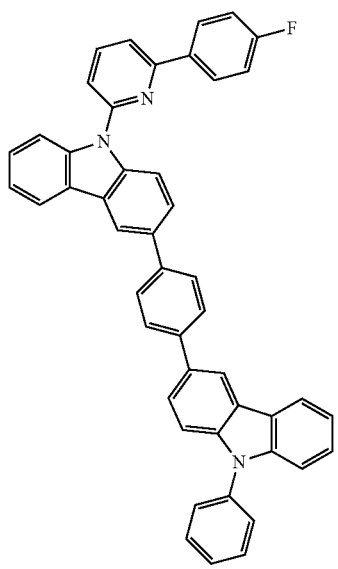

-continued
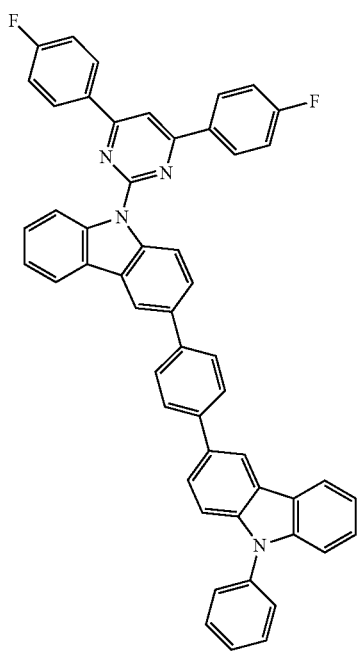 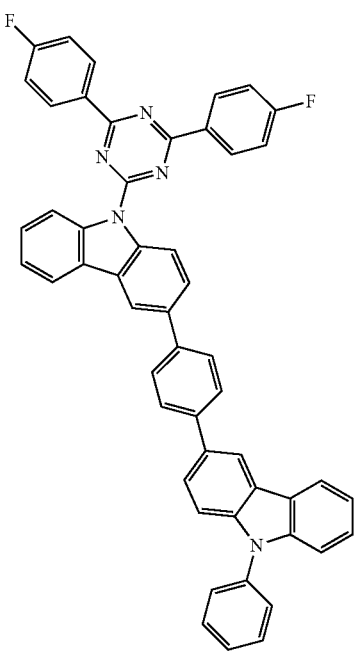 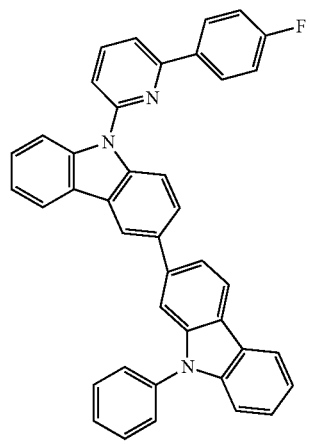
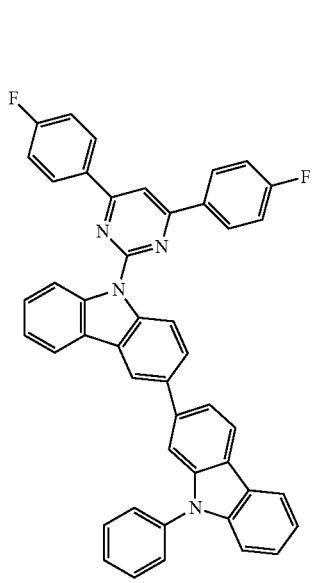 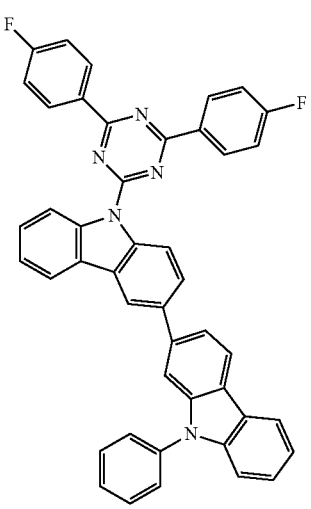 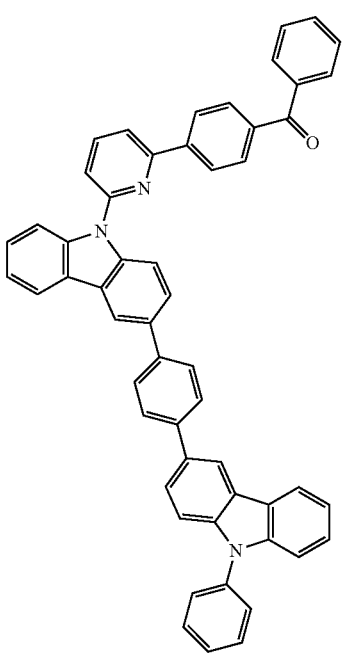

-continued
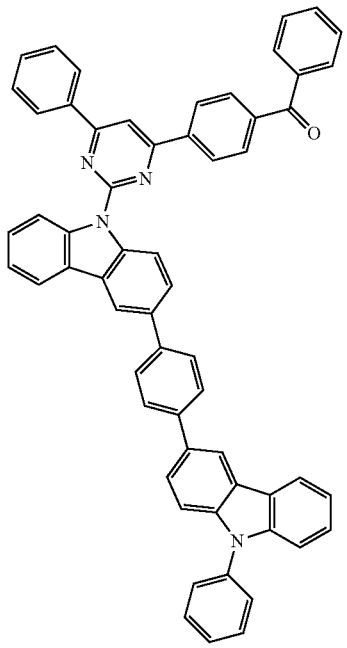
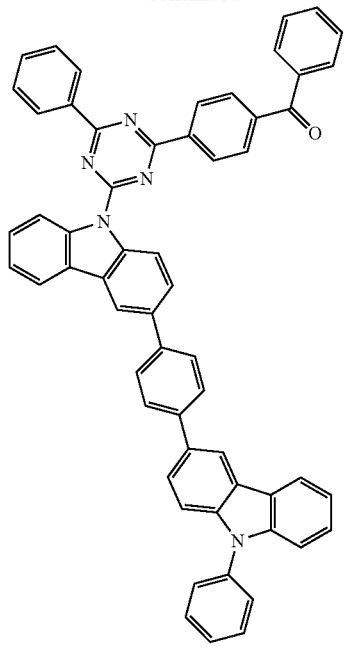
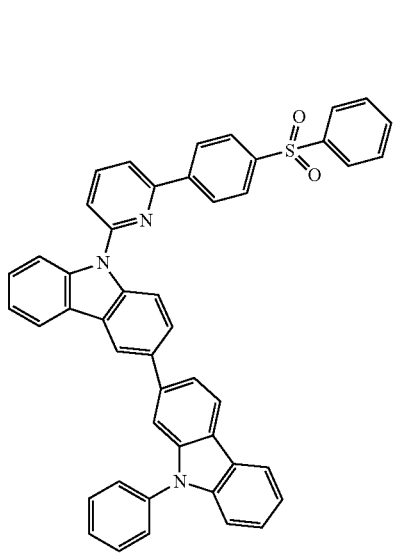
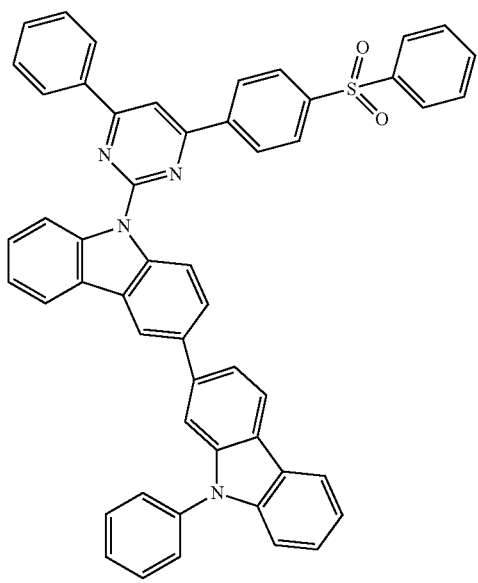
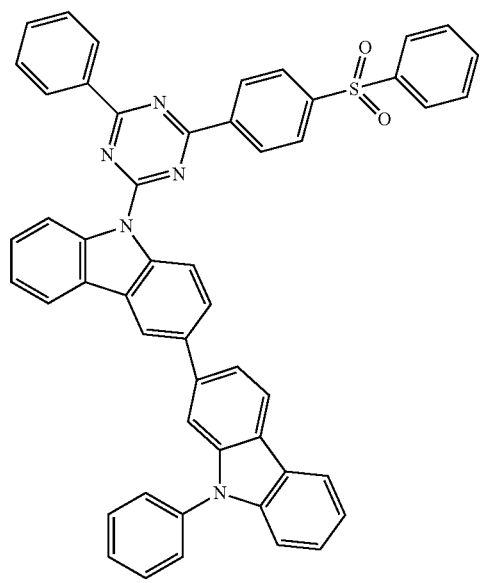
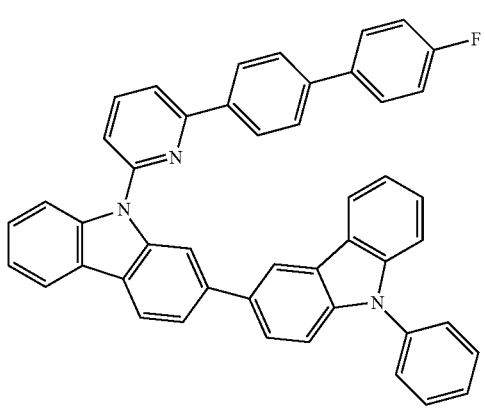
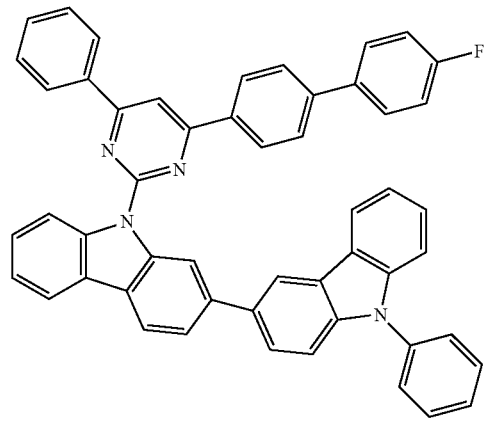

-continued
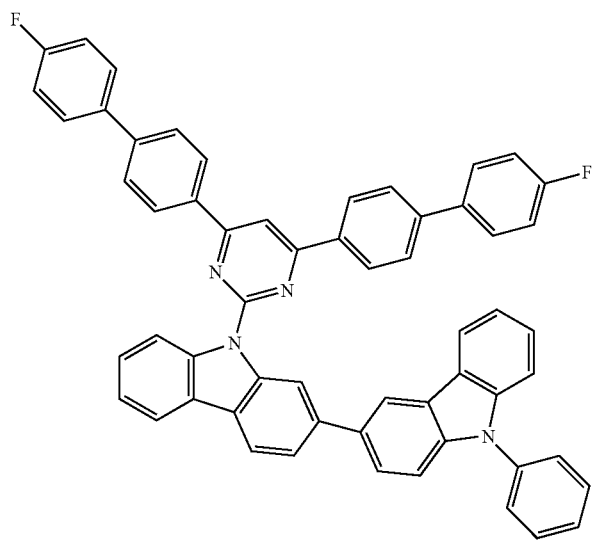
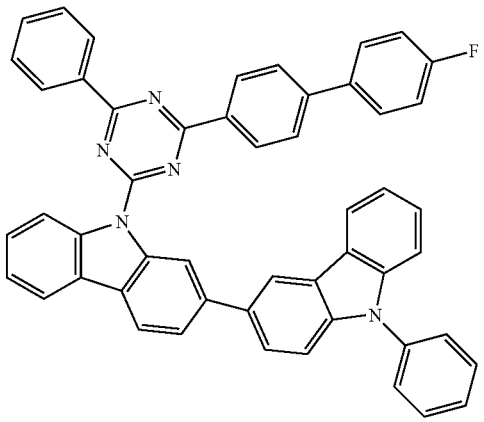
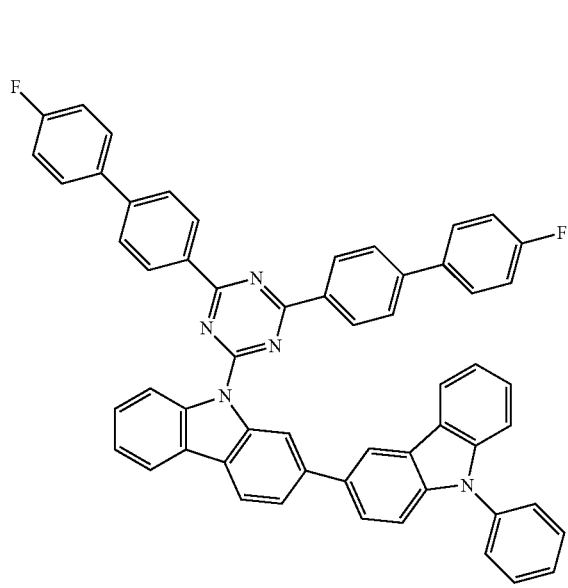
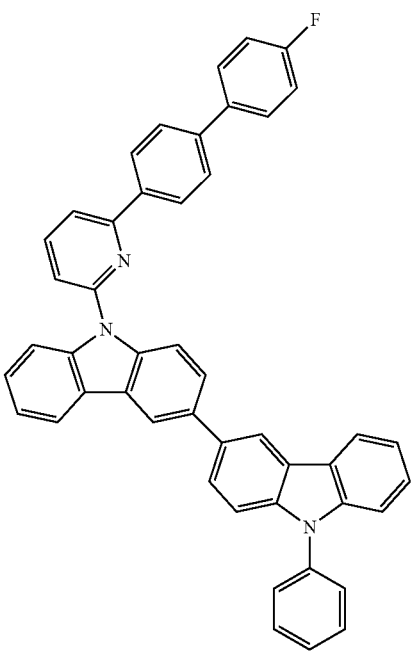

-continued
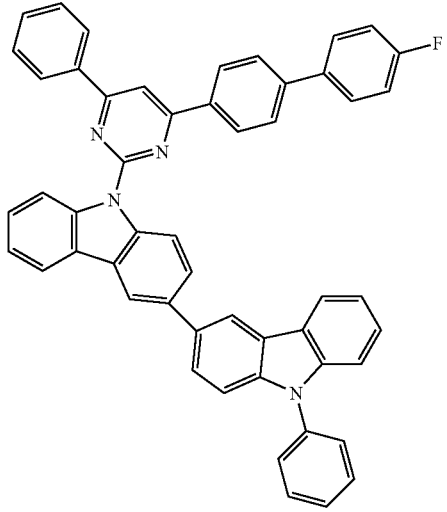
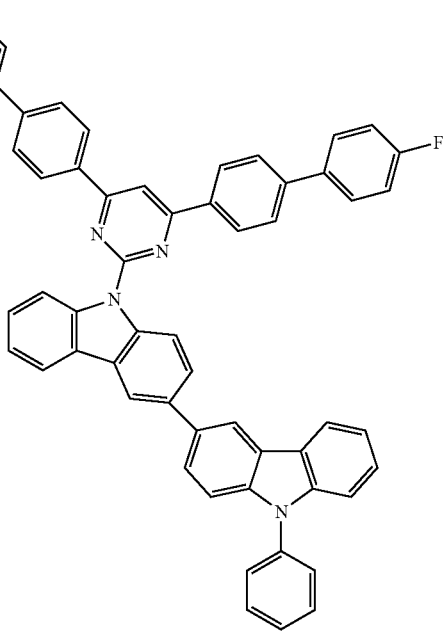
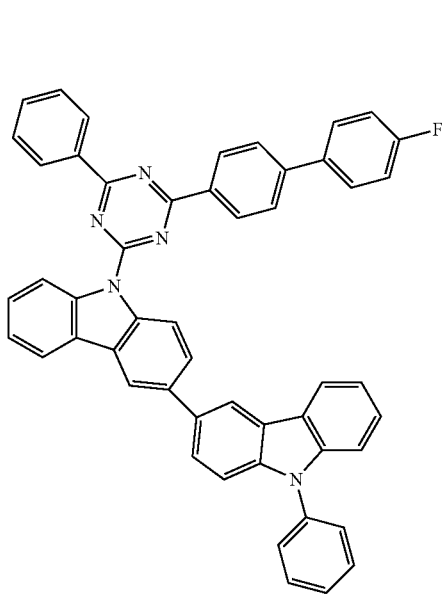
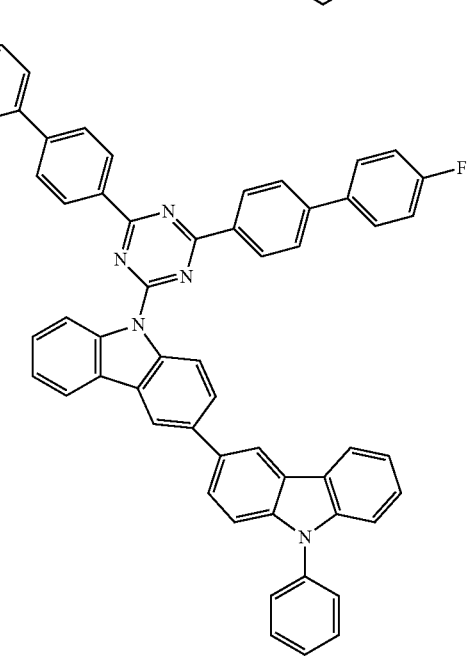
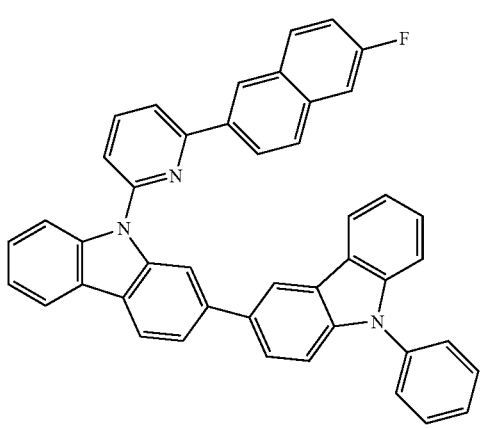
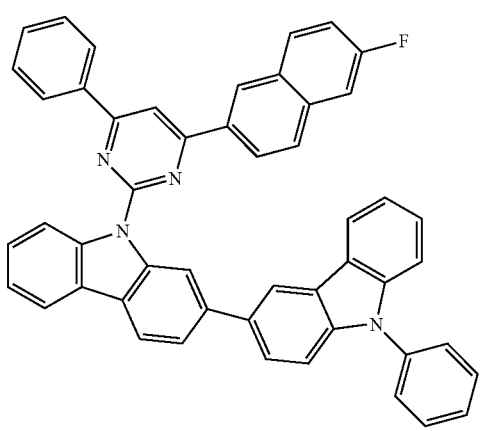

-continued
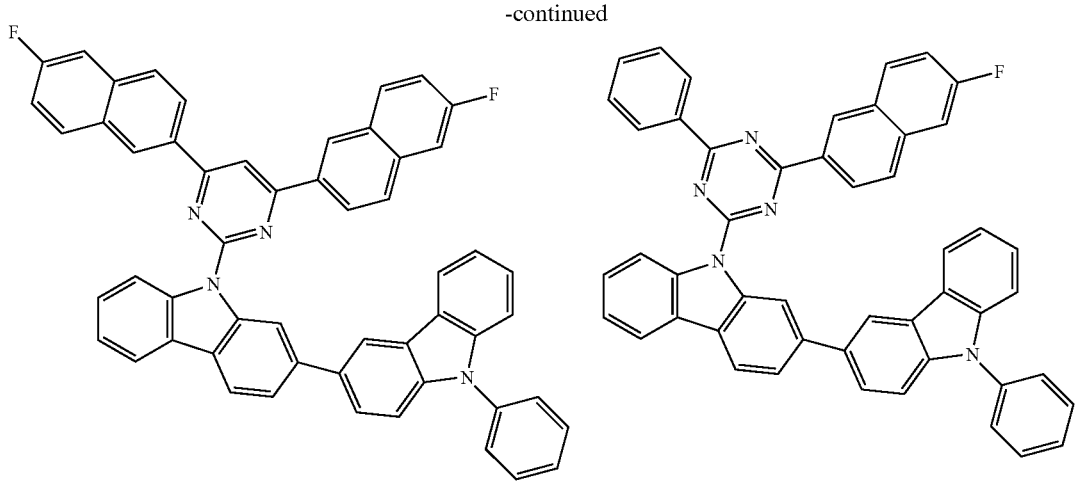
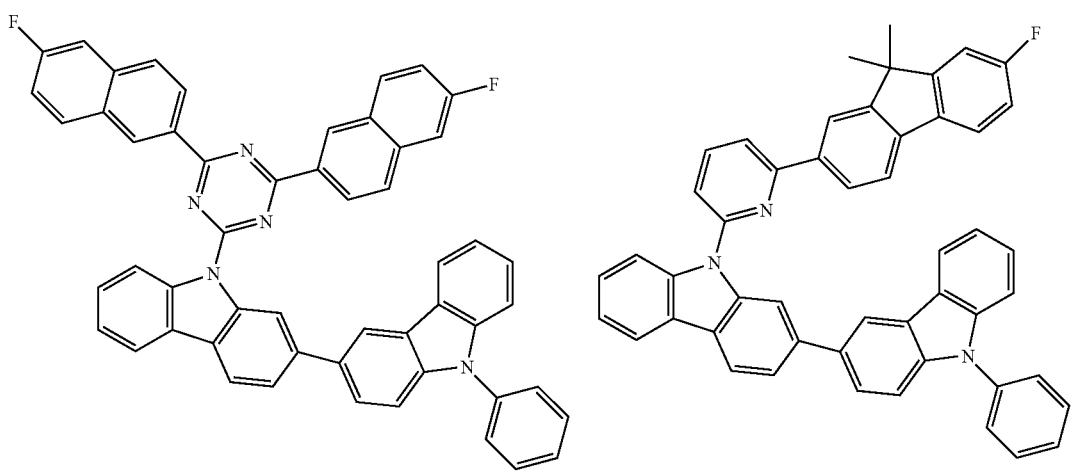
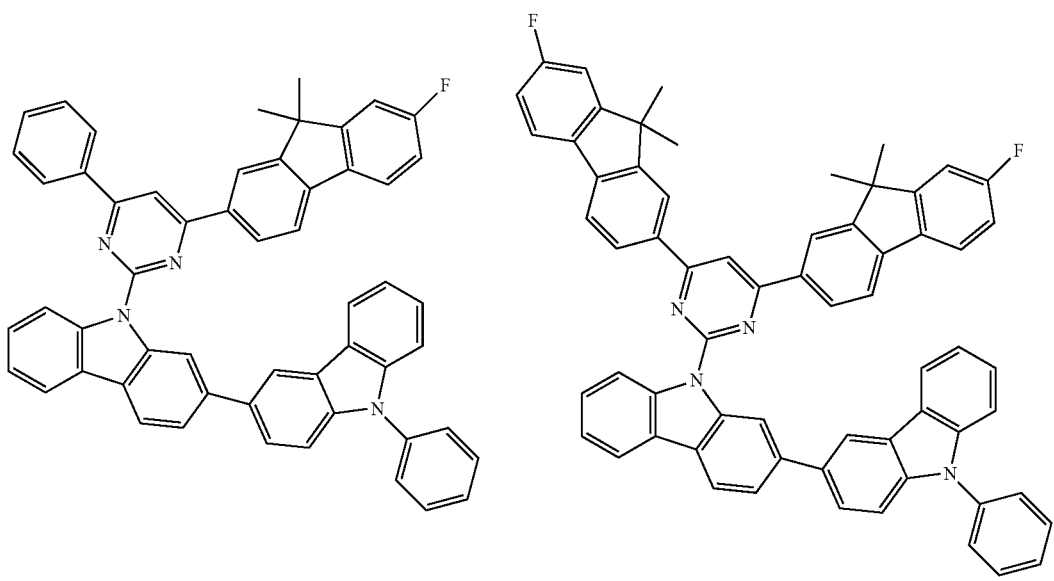

-continued
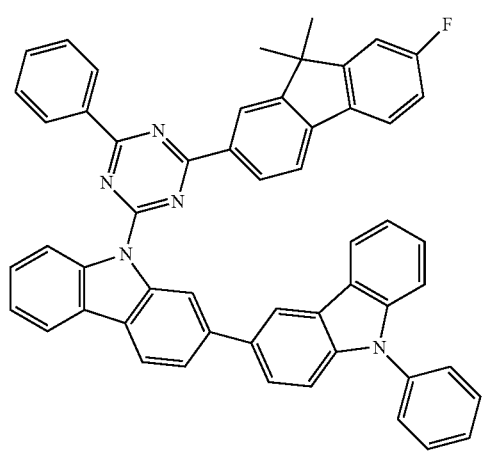
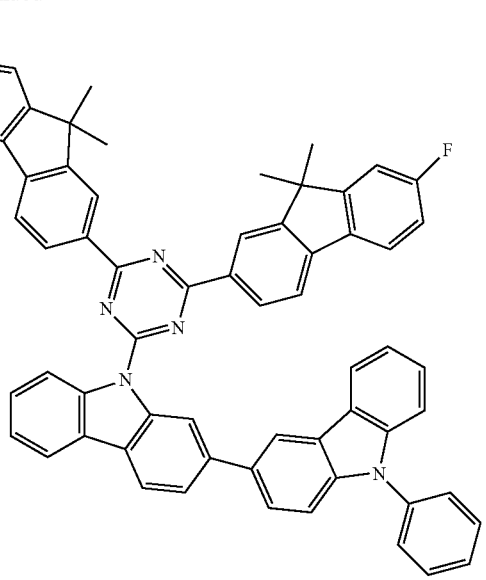
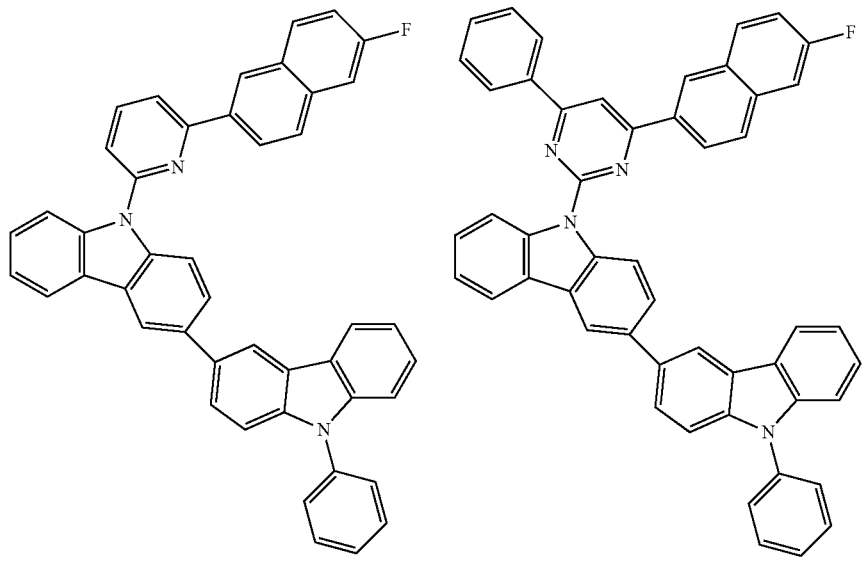

-continued
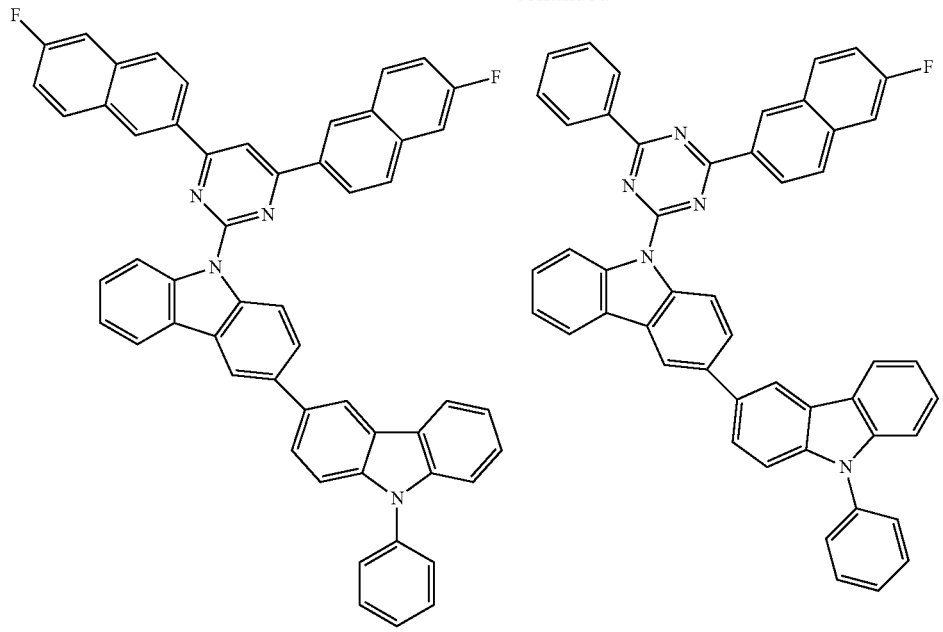
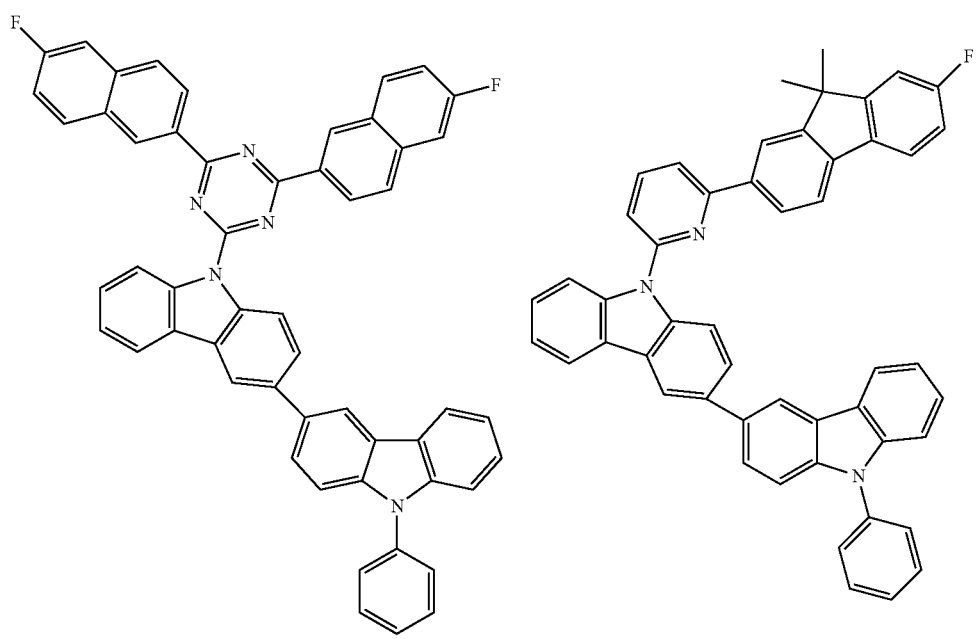

-continued
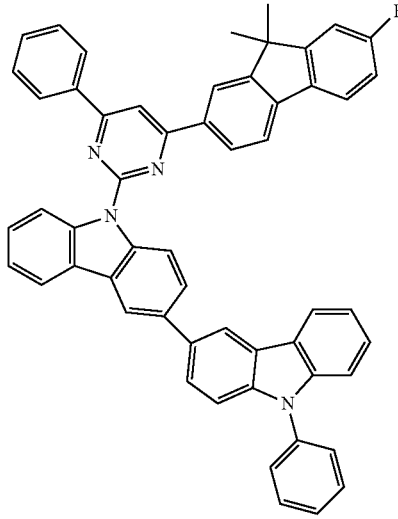
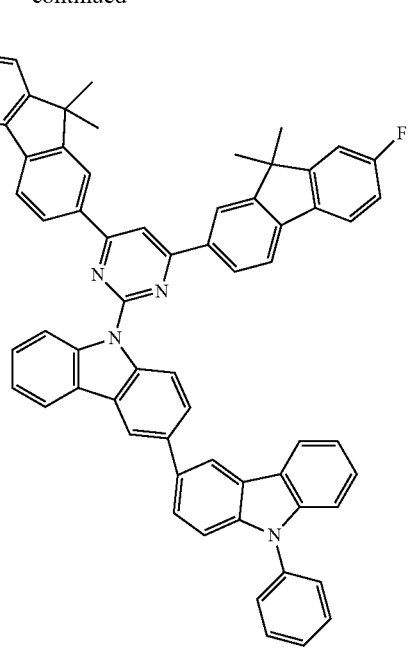
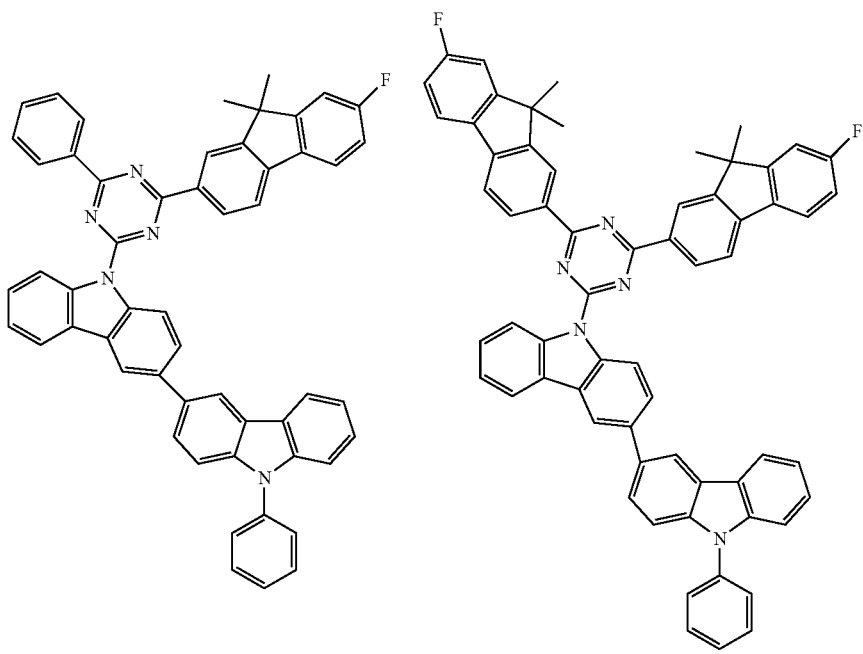

-continued
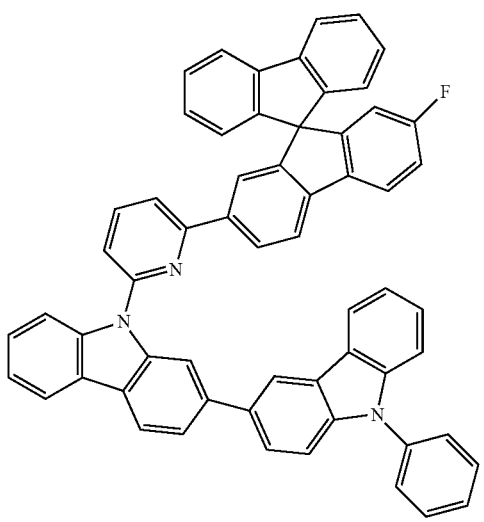
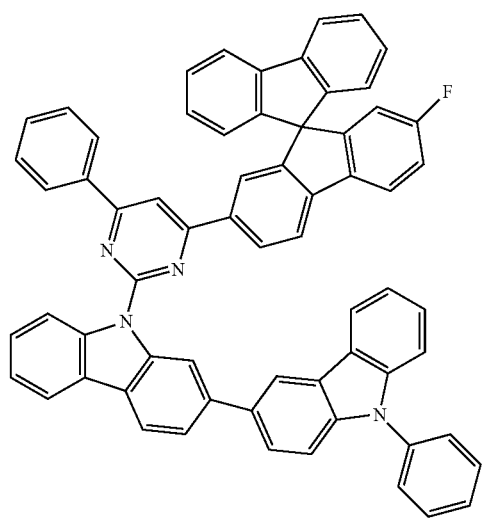
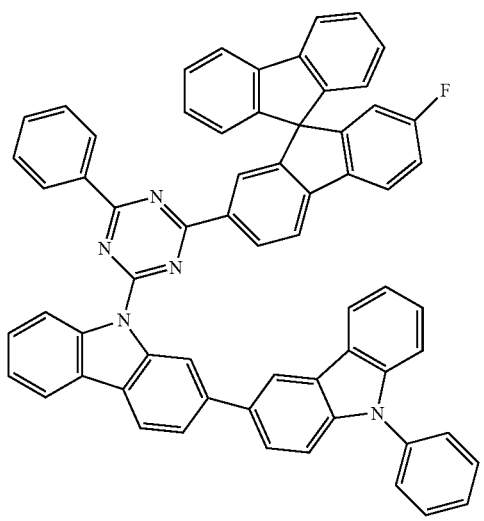
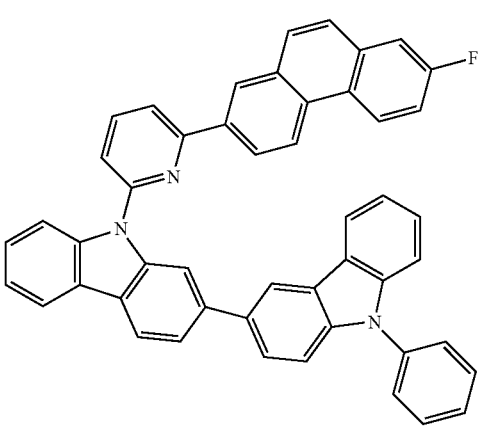
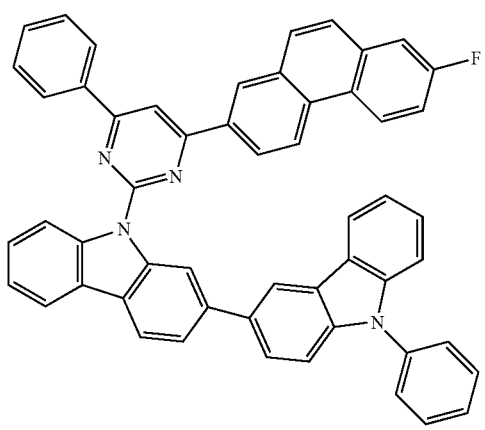
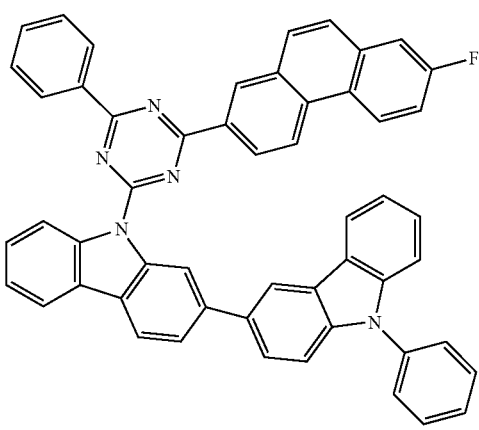

-continued
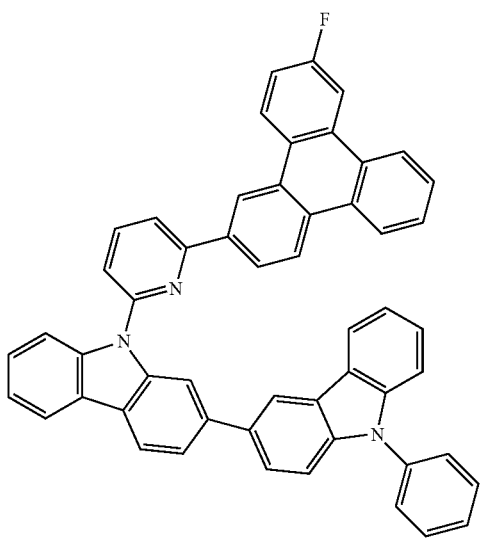
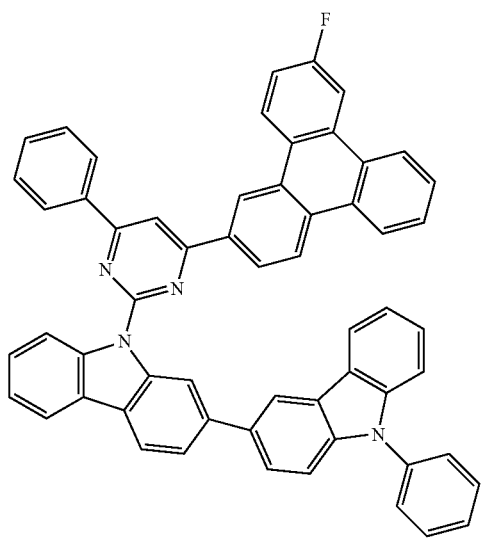
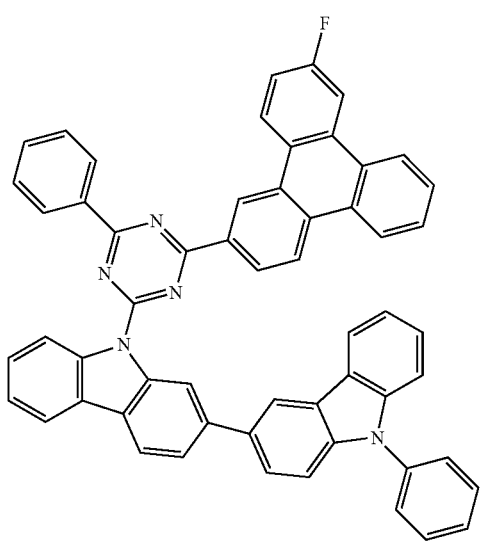
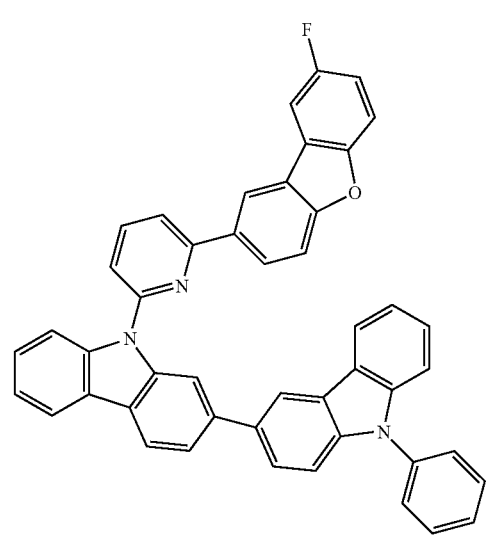
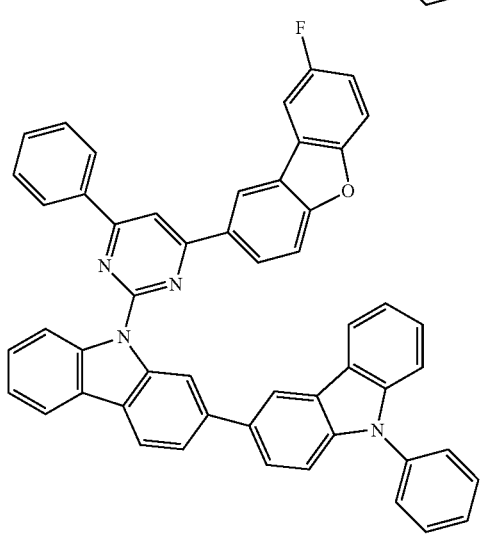
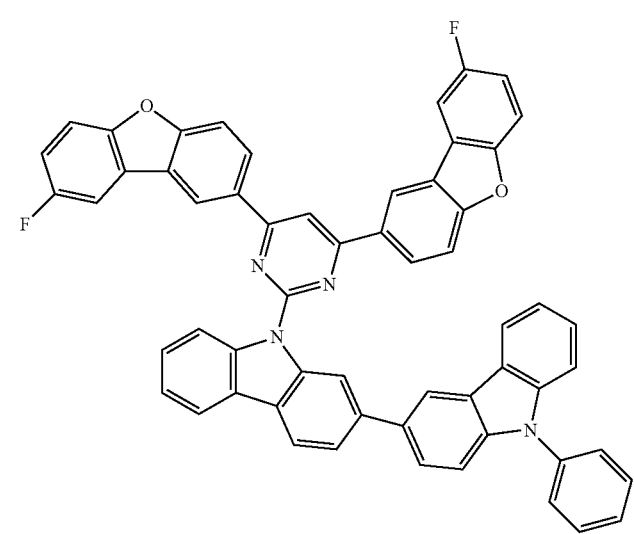

-continued
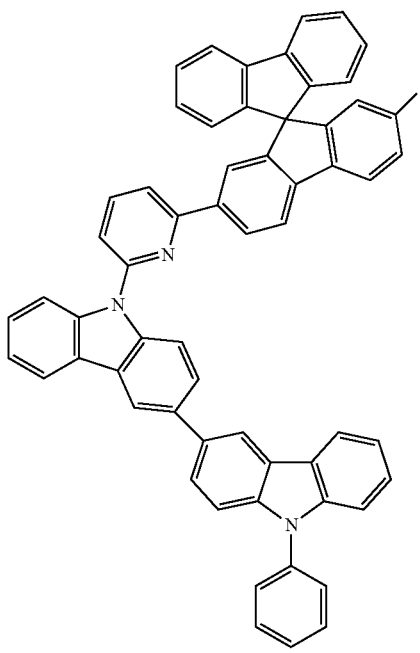
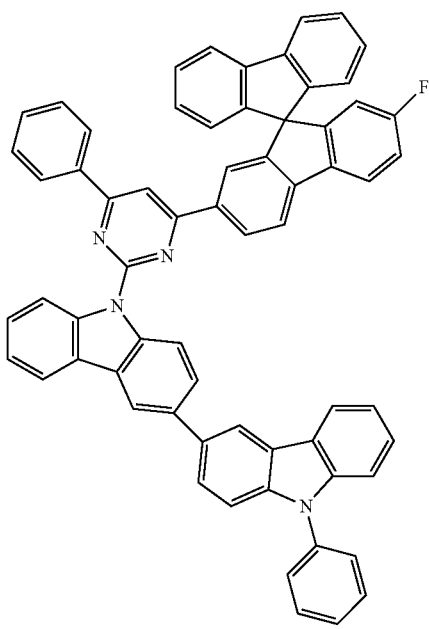
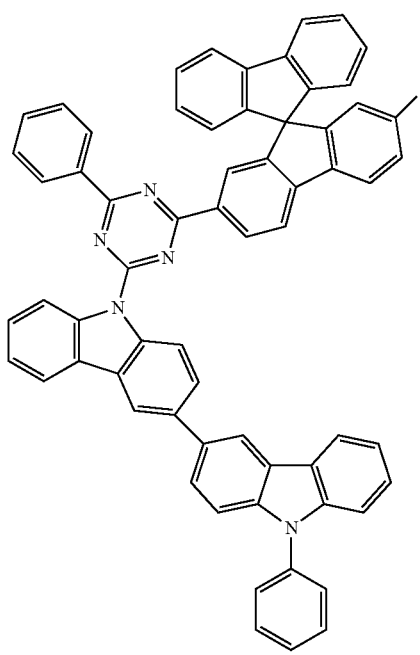
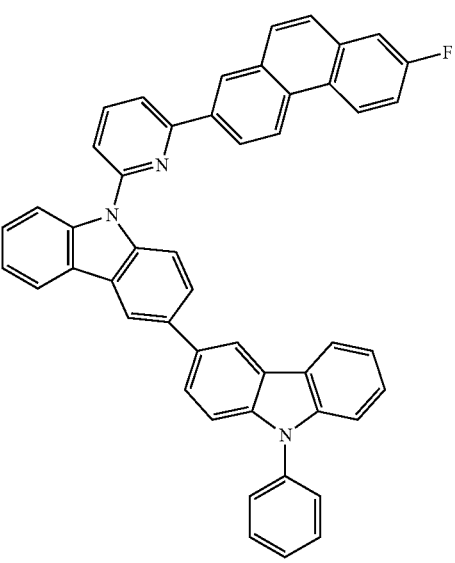

-continued
53
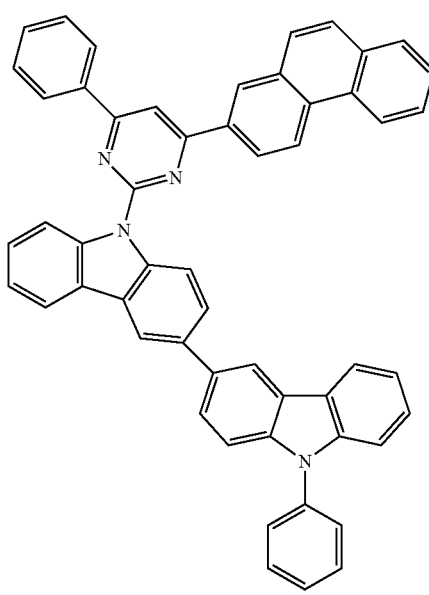
54
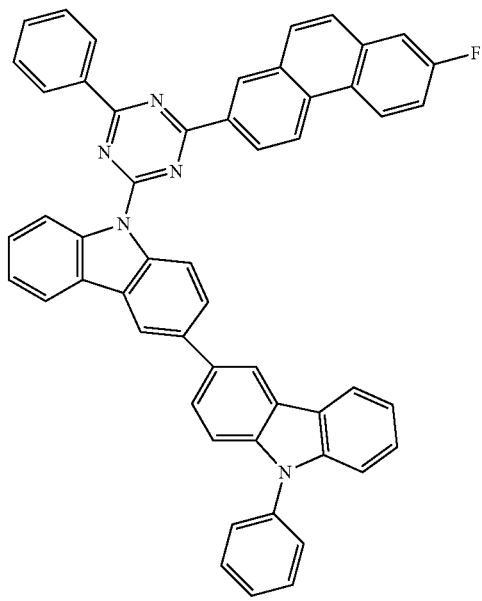
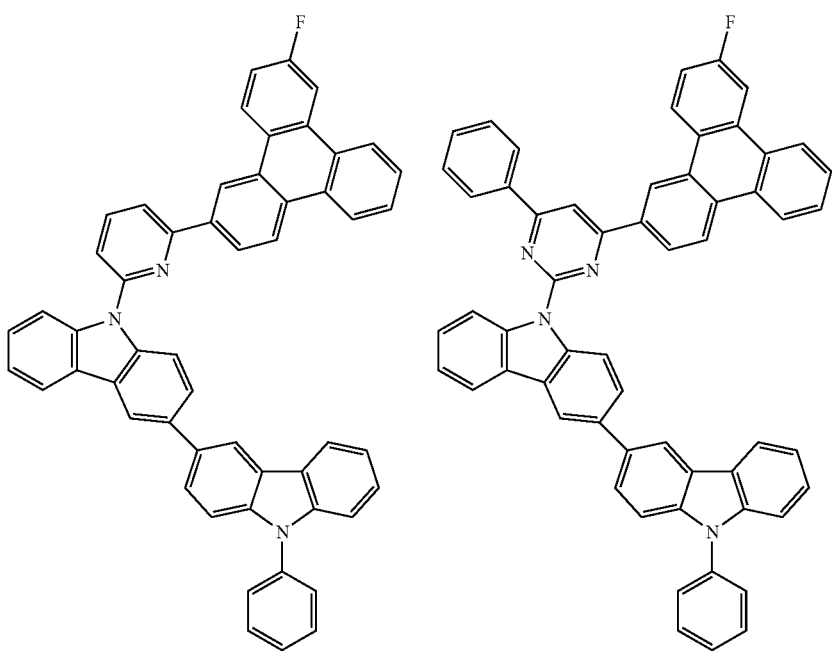

-continued
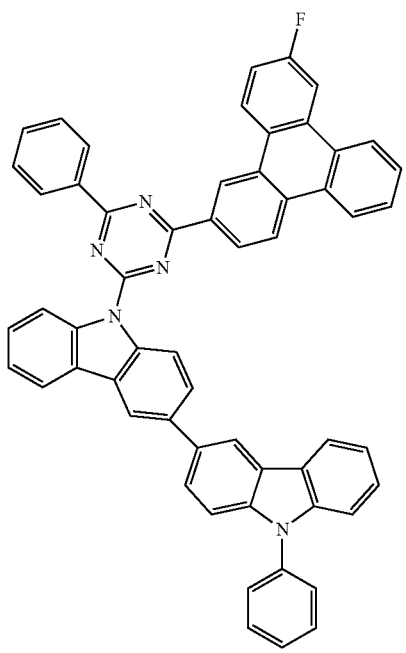
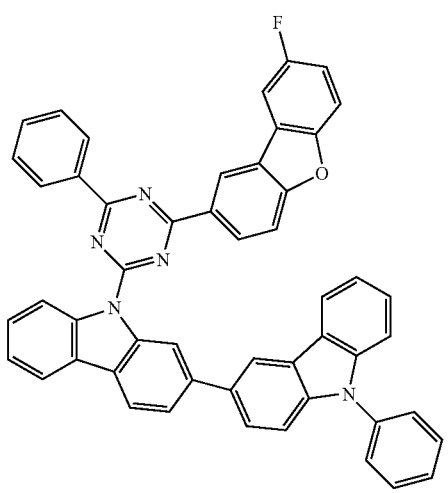
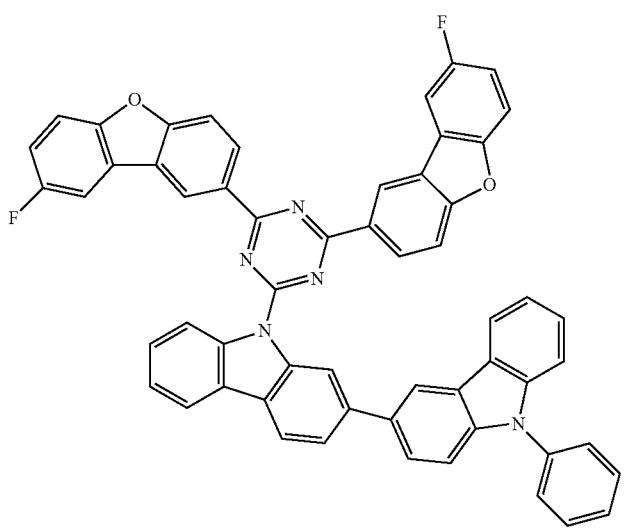
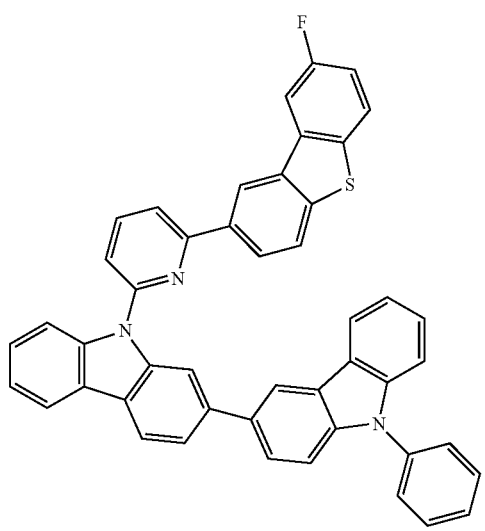
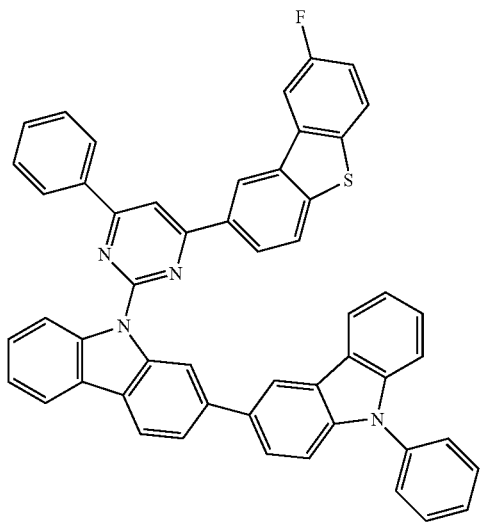
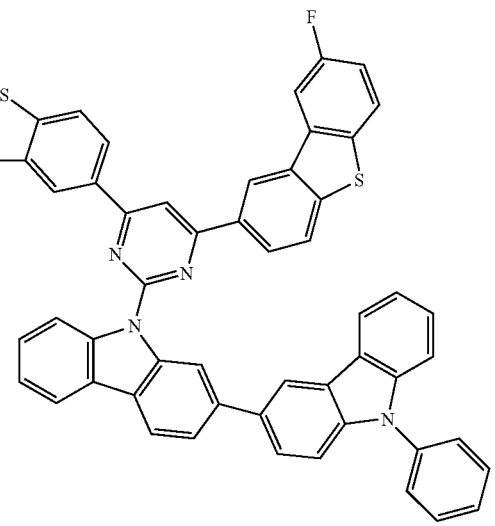

-continued
57
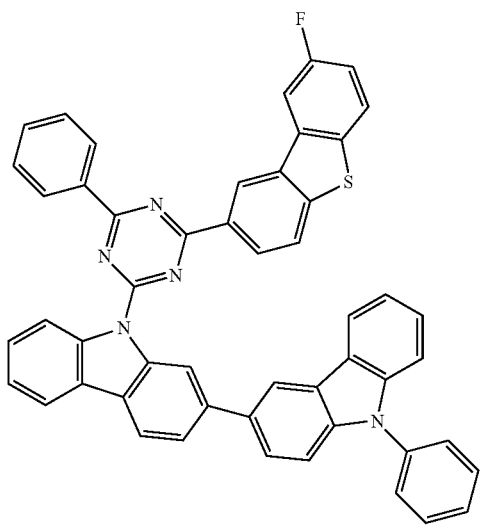
58
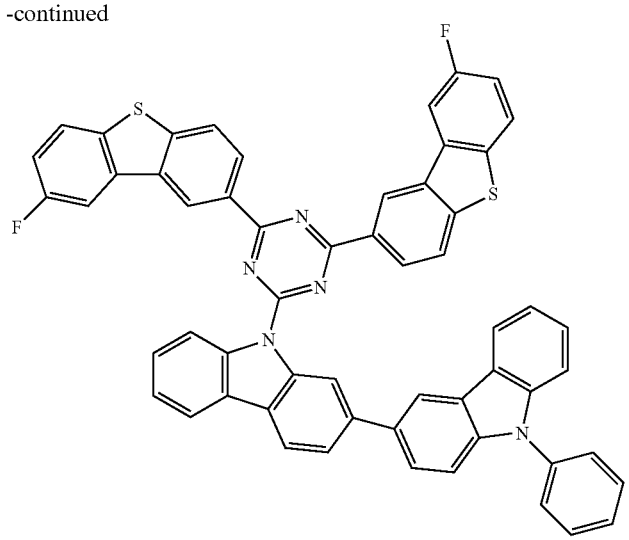
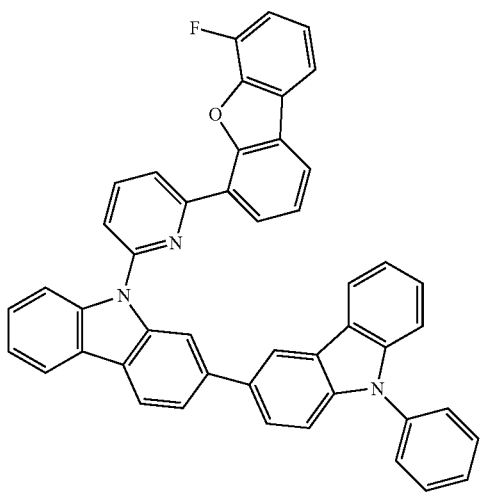
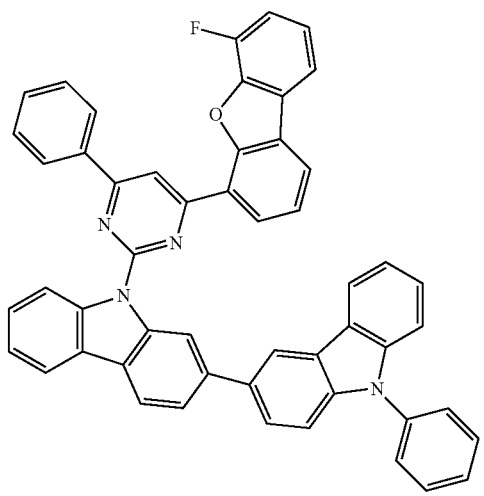
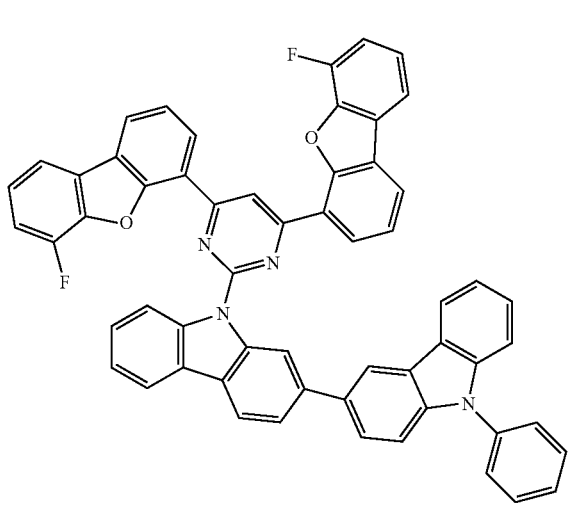
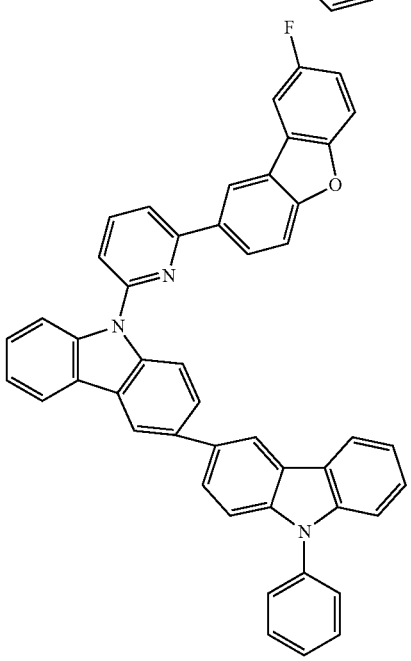

-continued
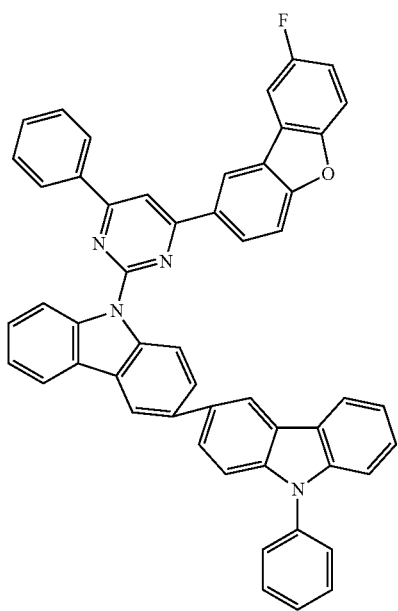
59
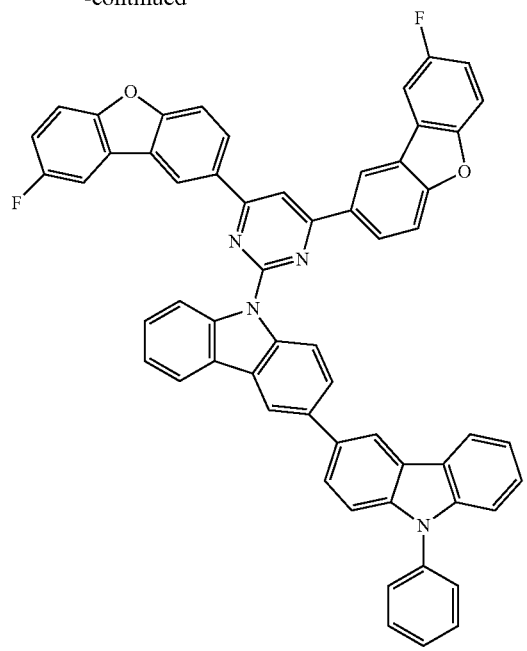
60
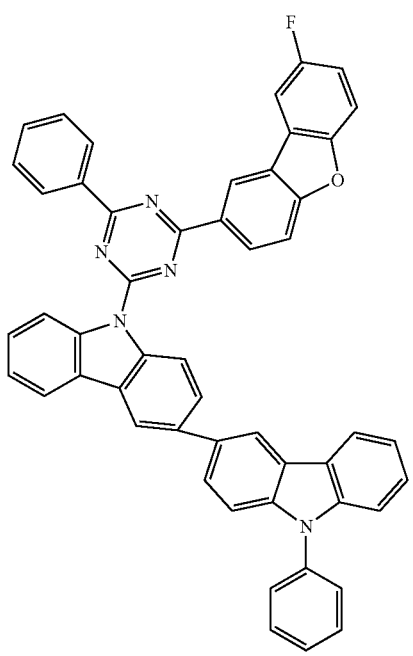
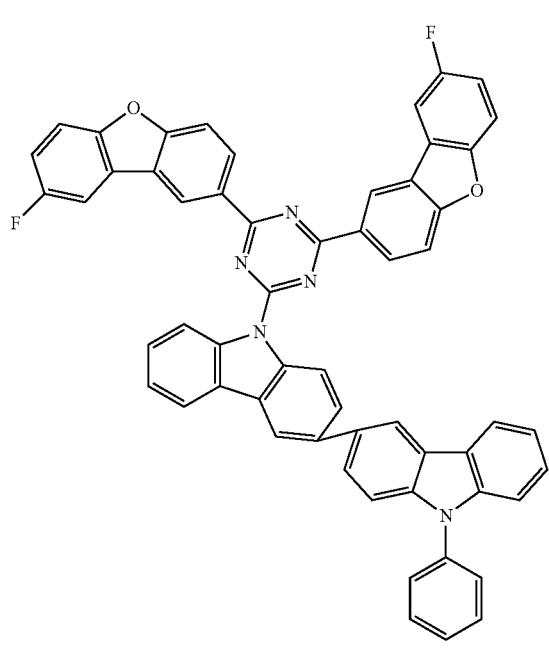

-continued
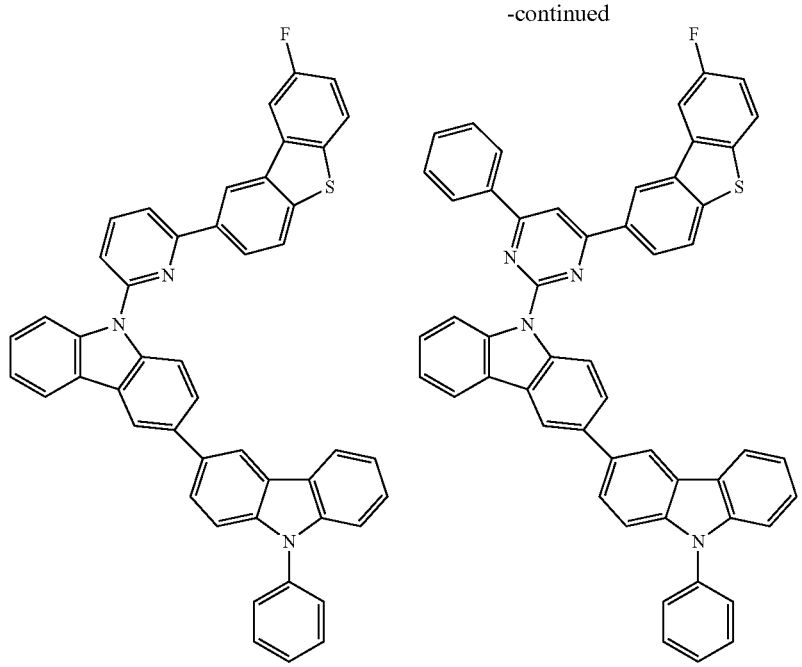
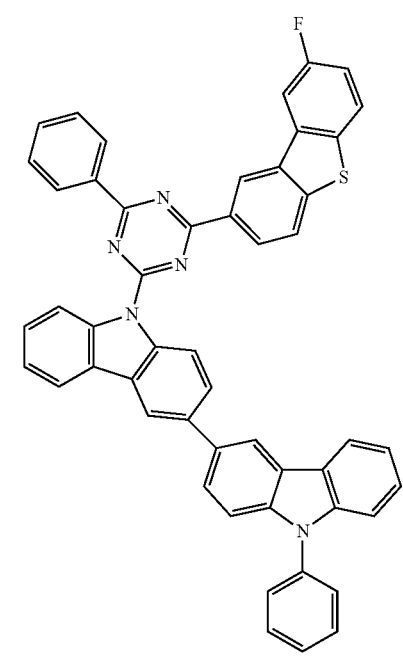

-continued
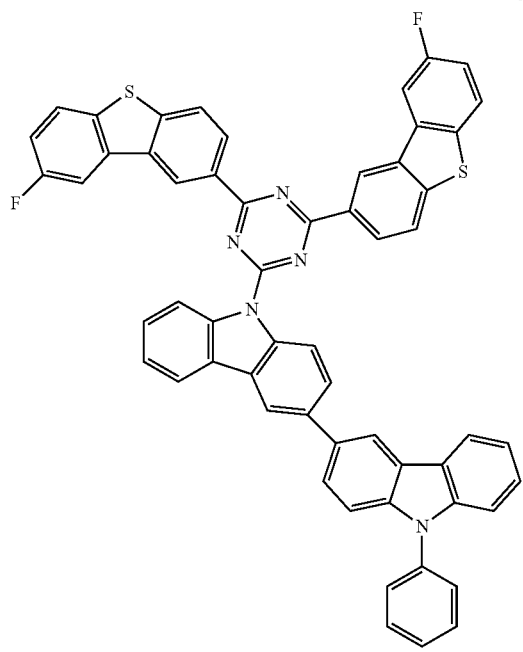 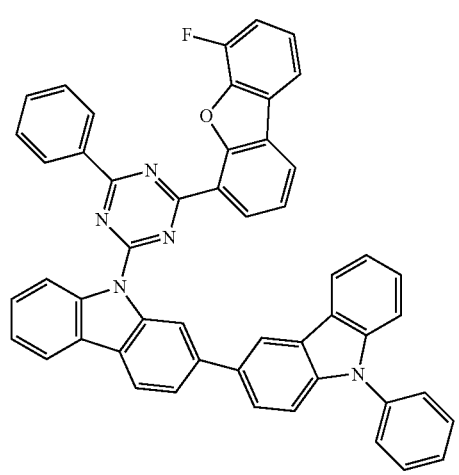
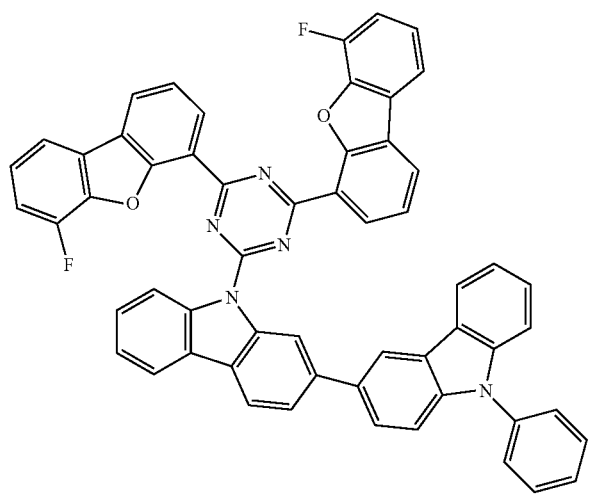 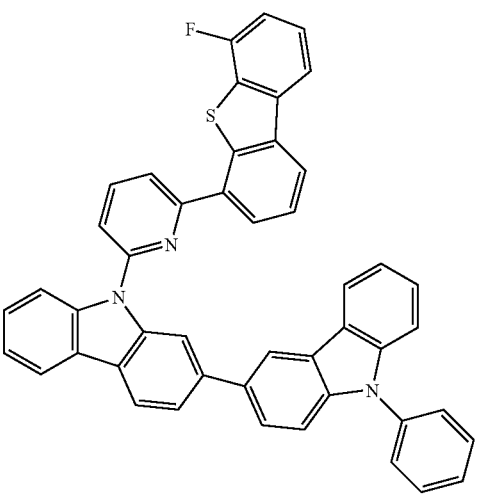
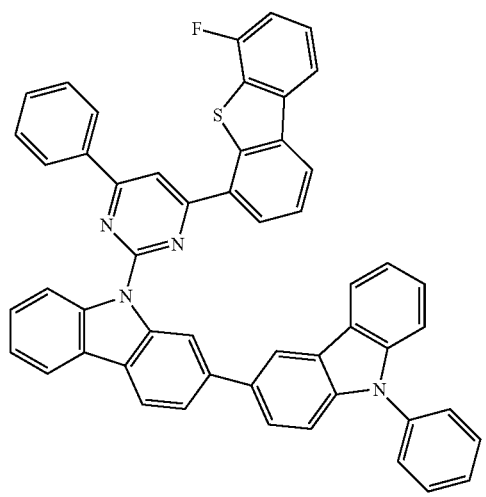 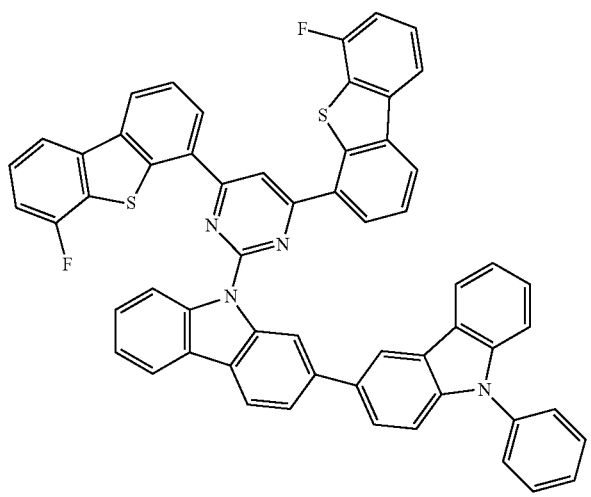

65
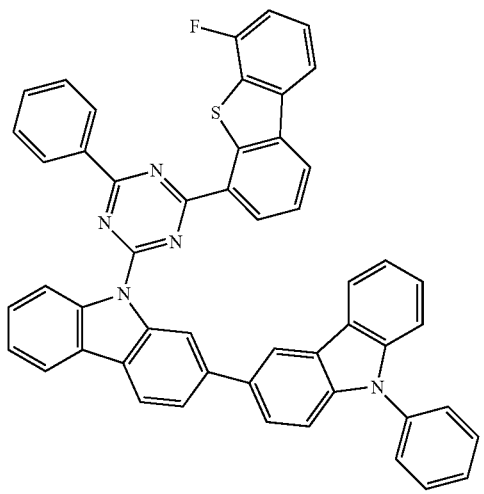
66
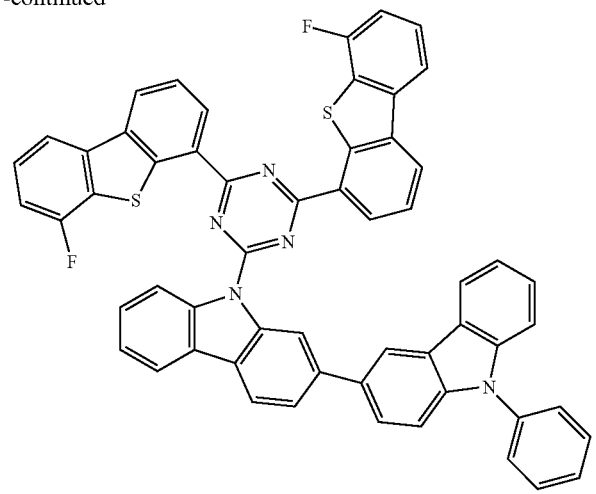
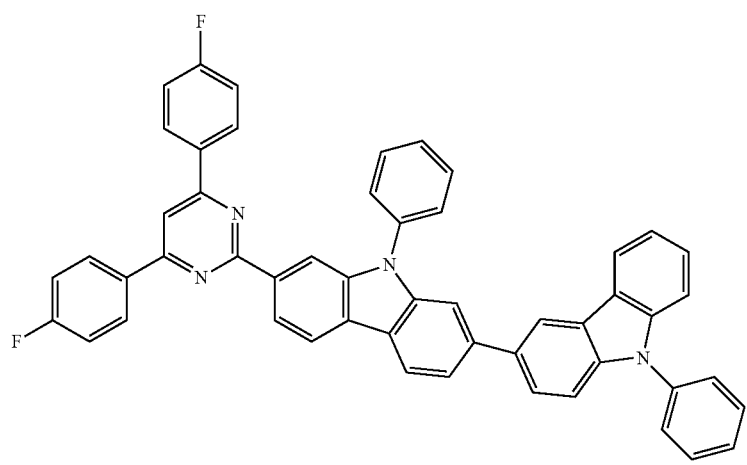
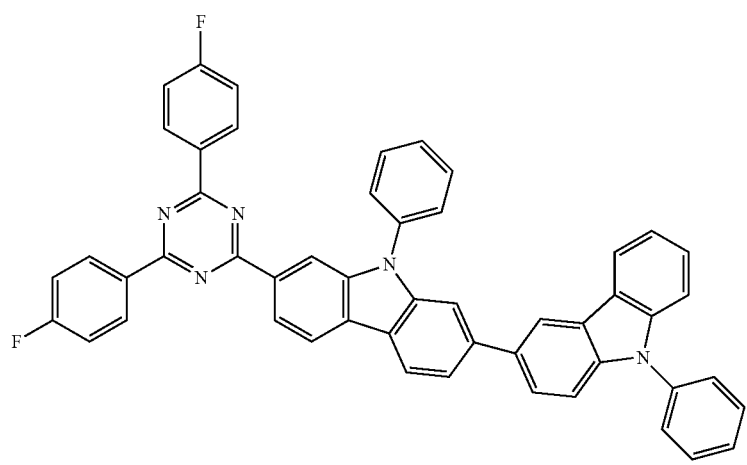

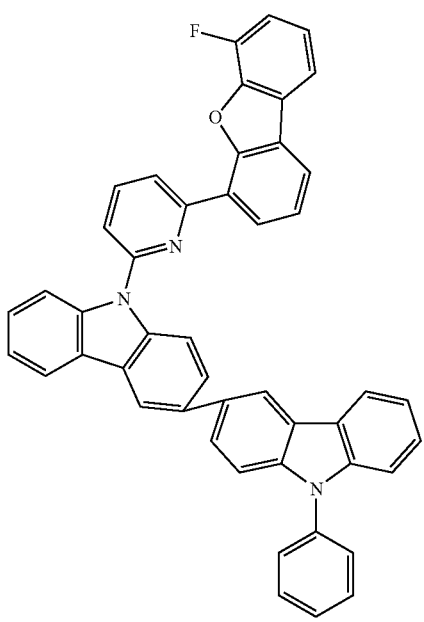
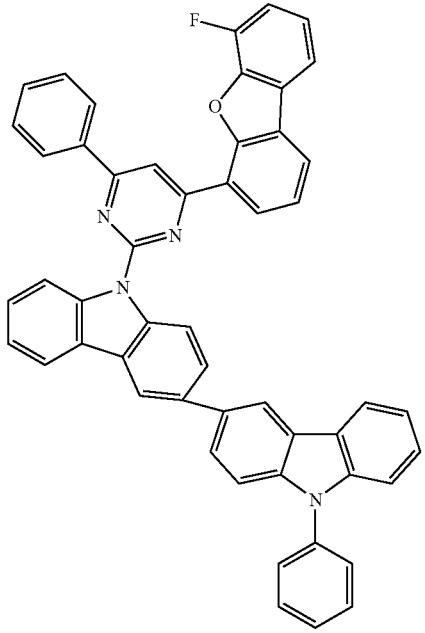
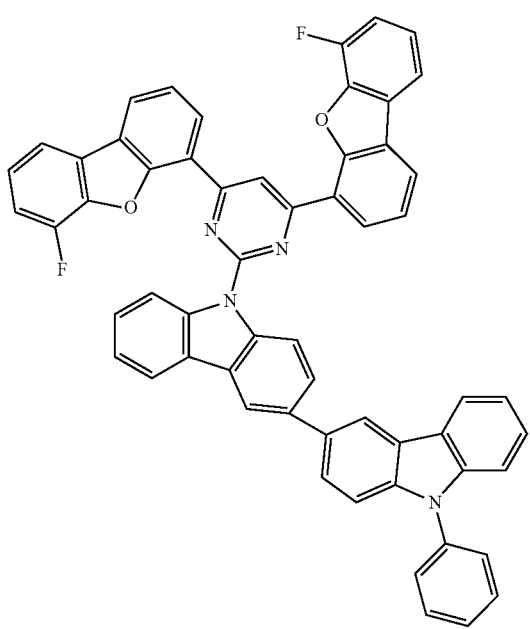
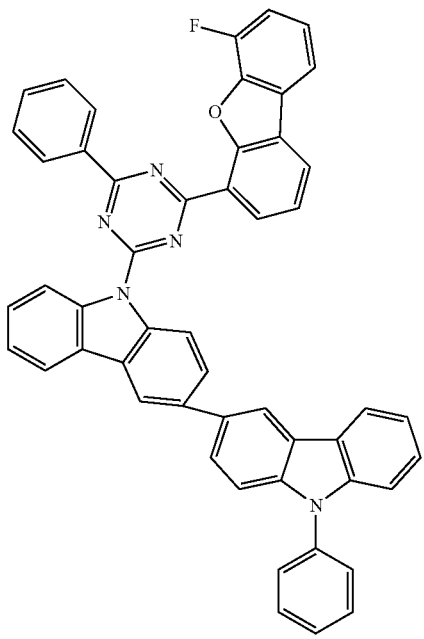

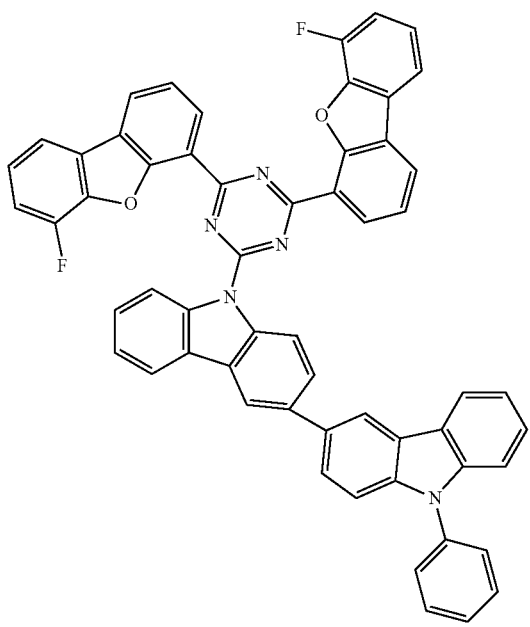
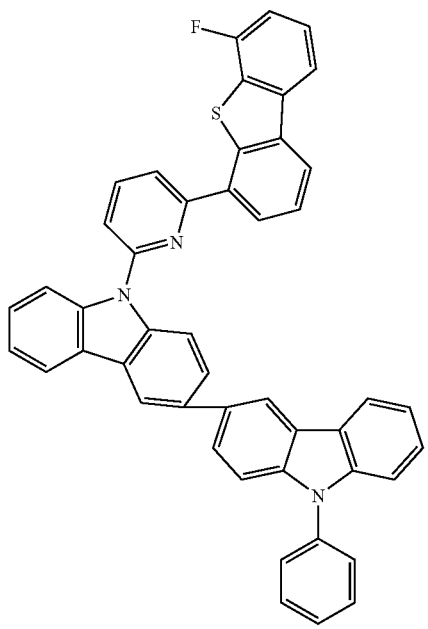
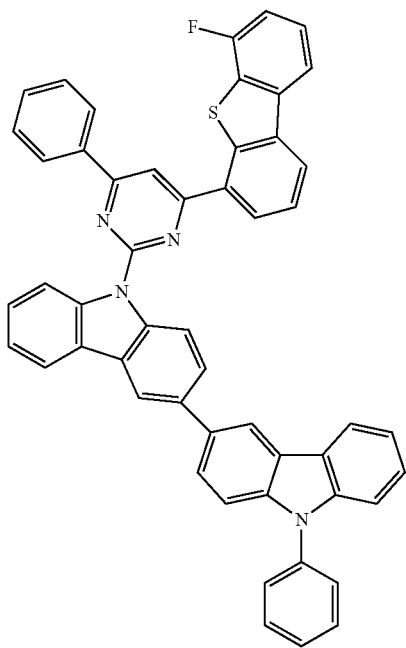
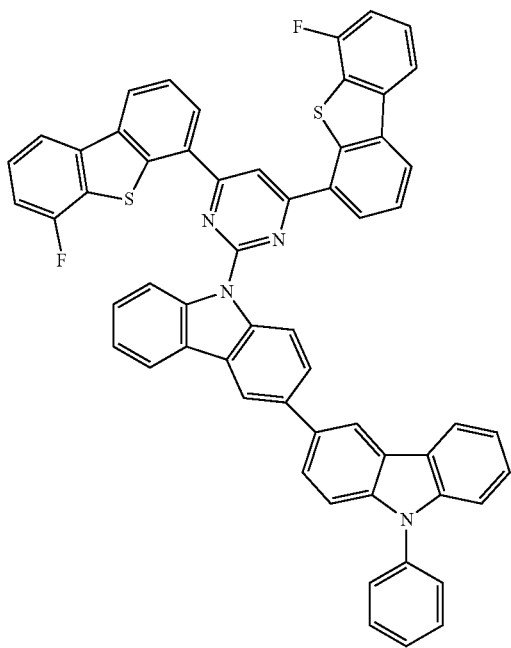

-continued
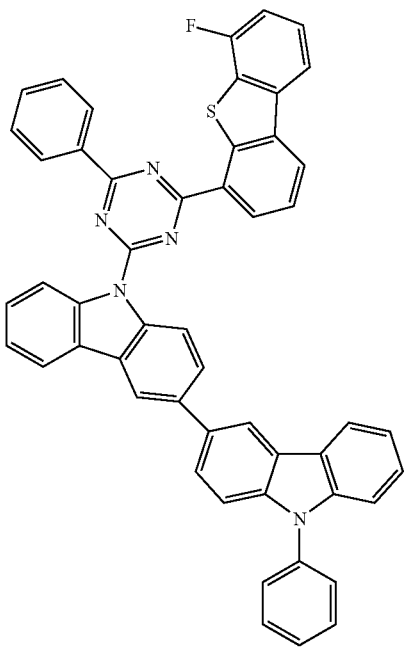
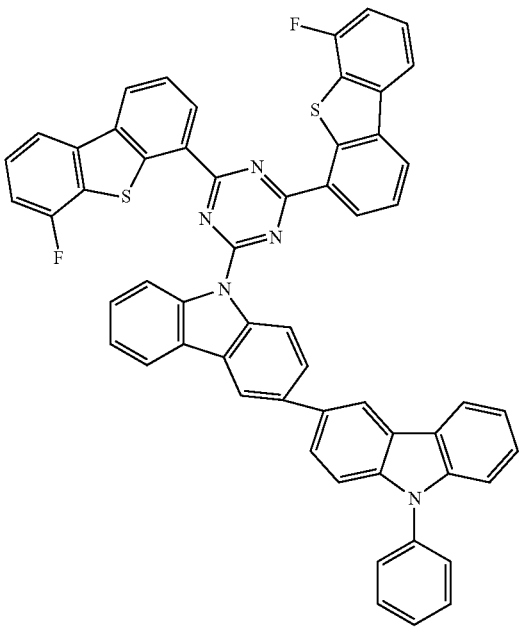
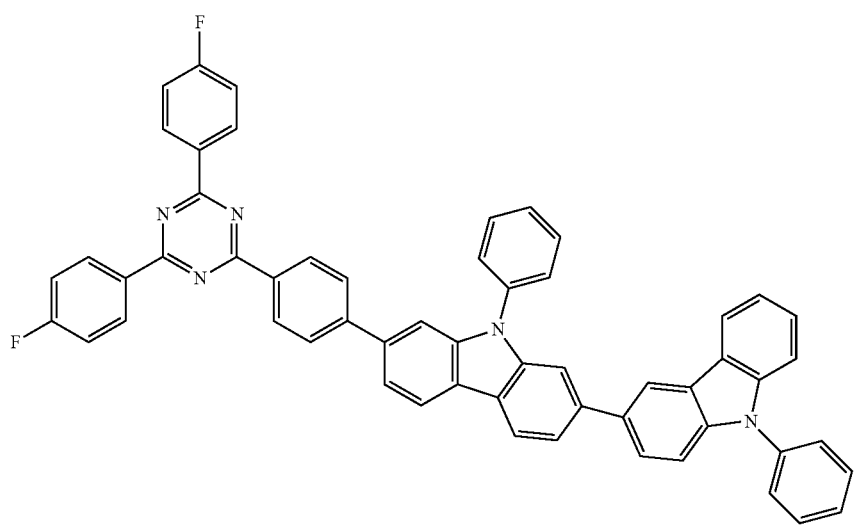
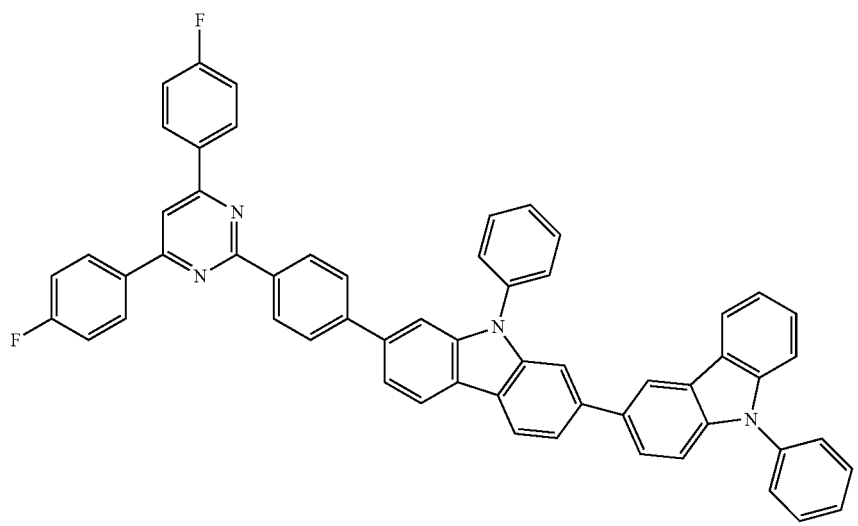

-continued
73
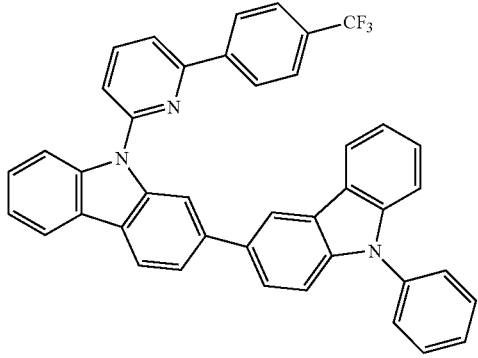
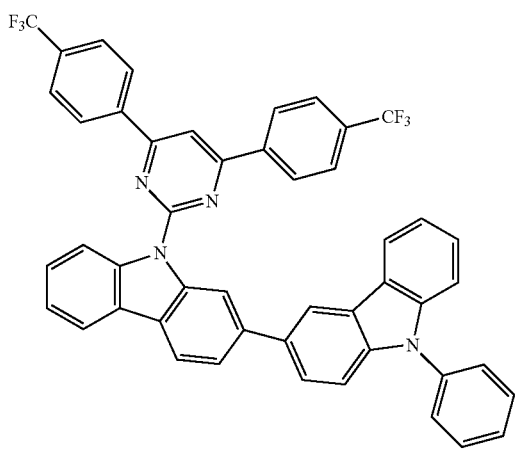
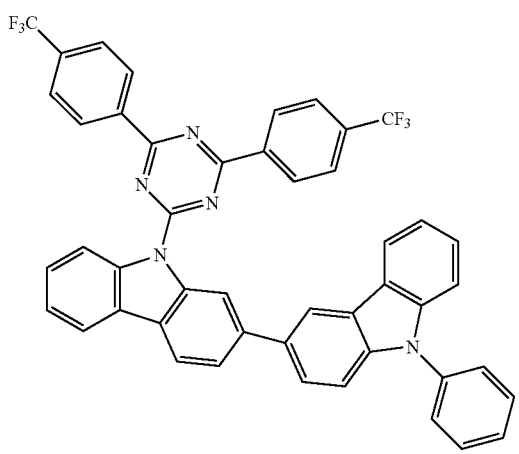
74
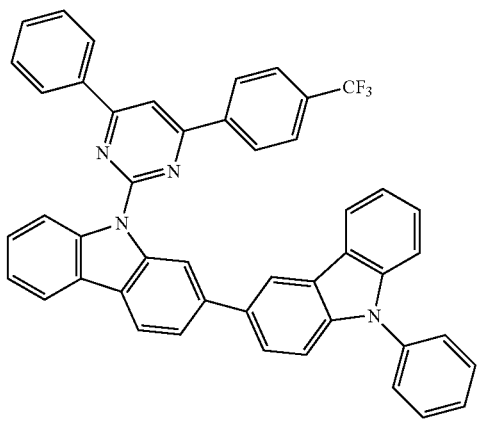
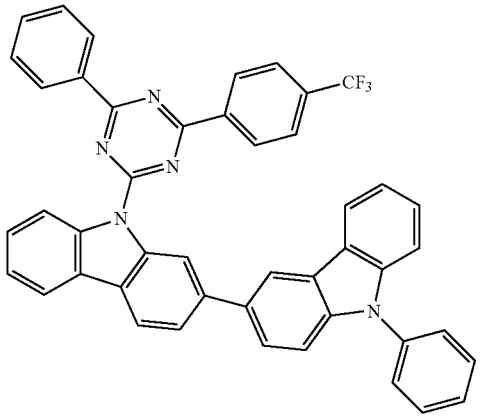
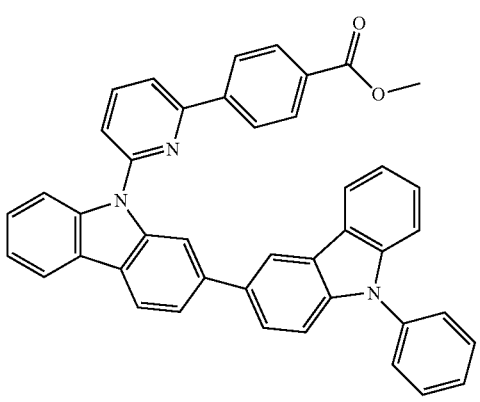

75
76
-continued
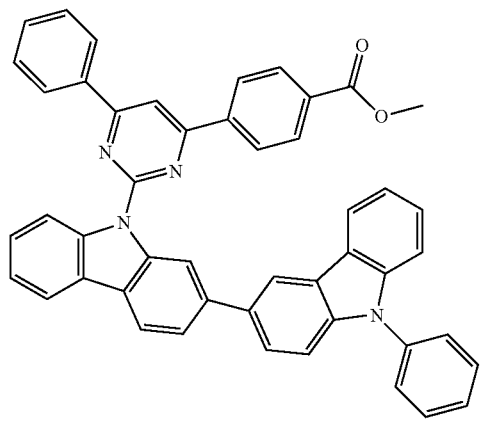
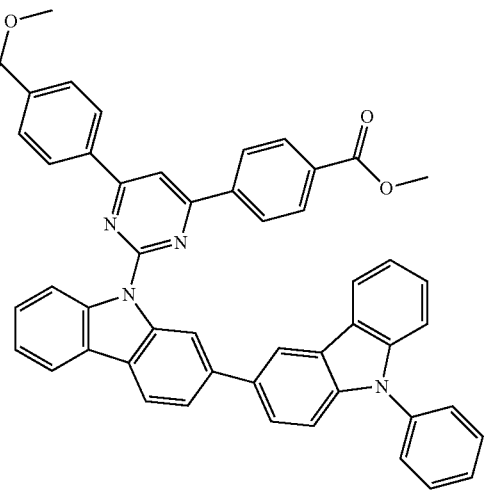
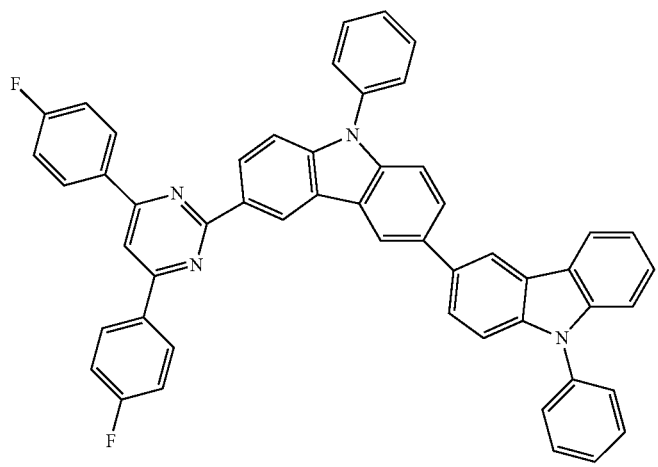
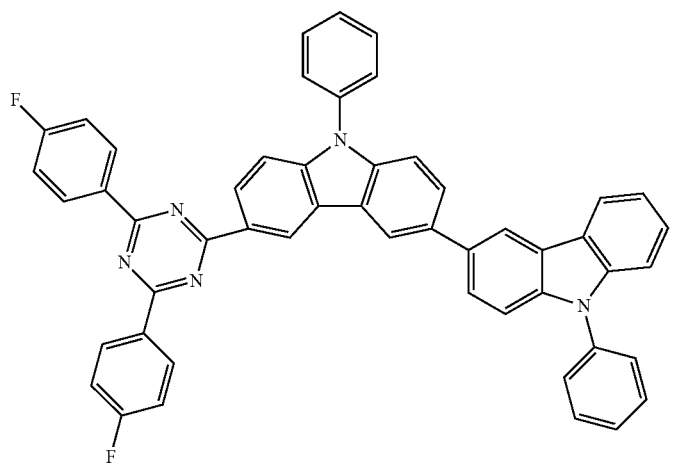

-continued
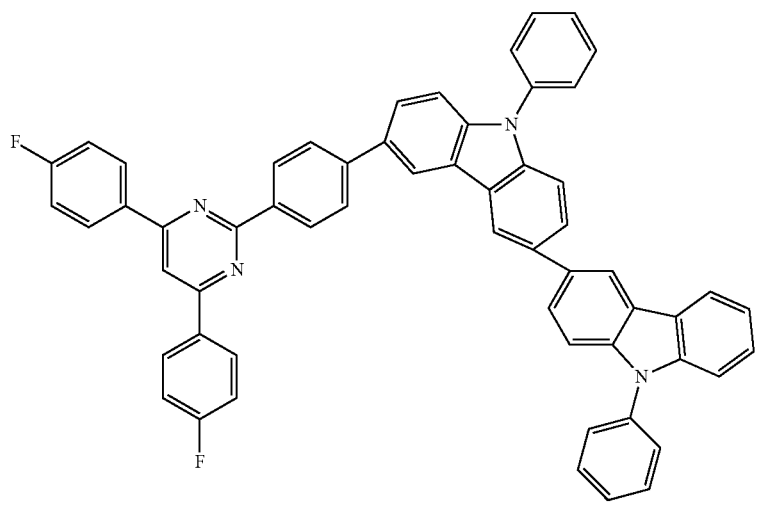
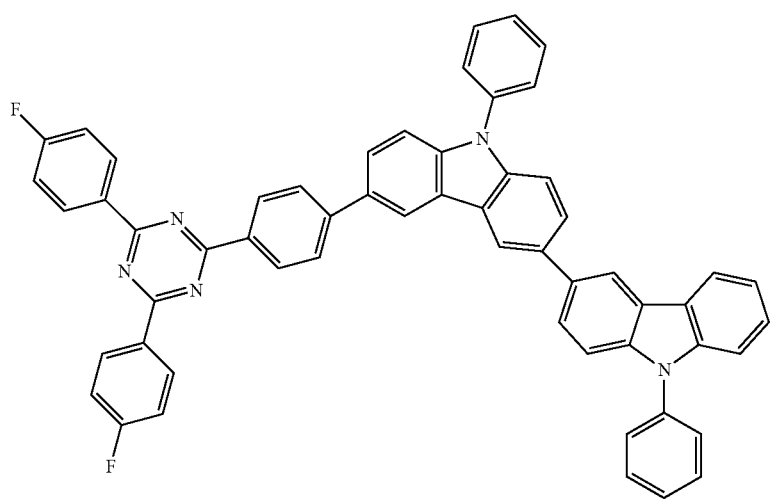
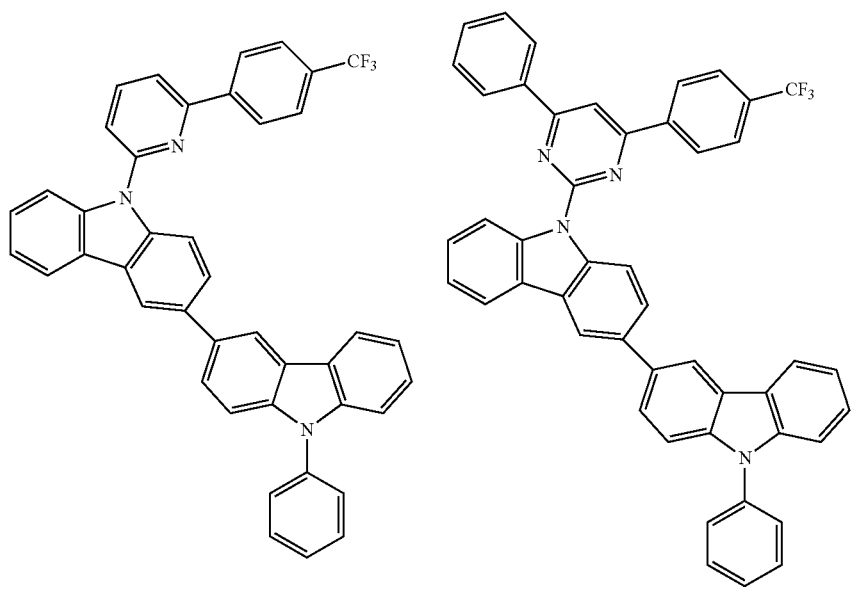

-continued
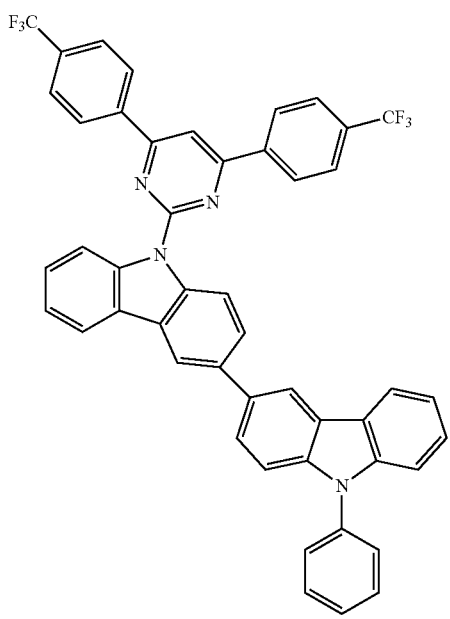
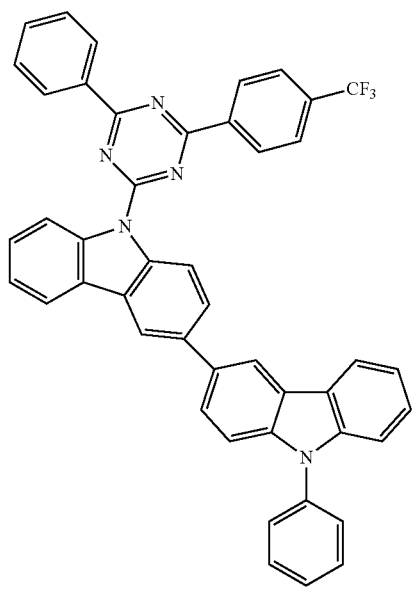
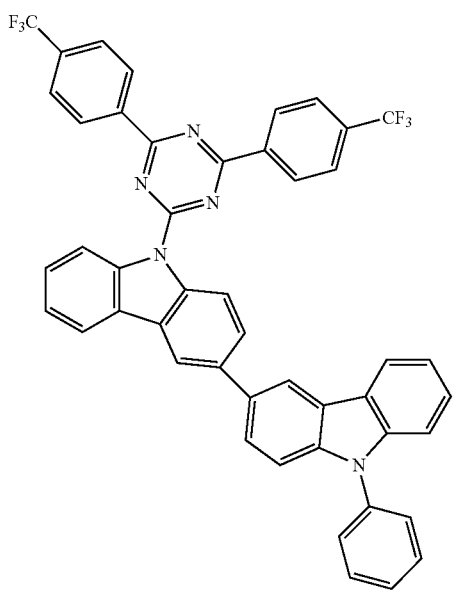
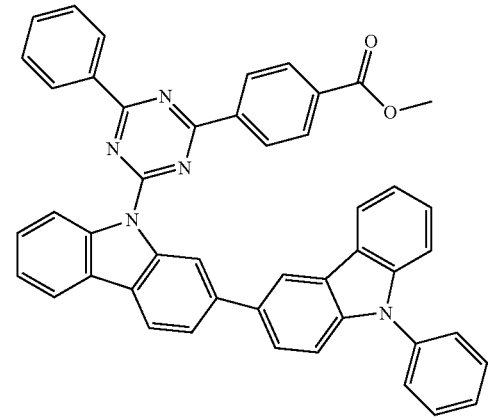
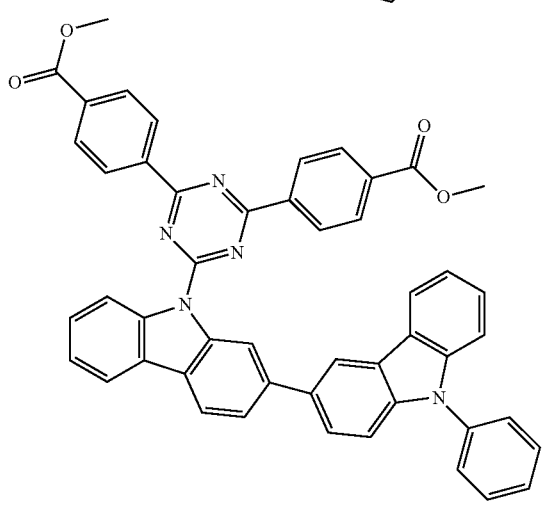
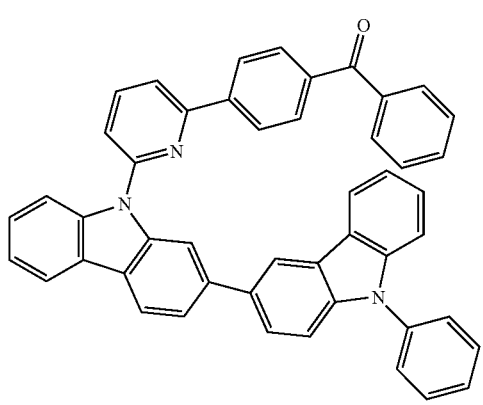

81
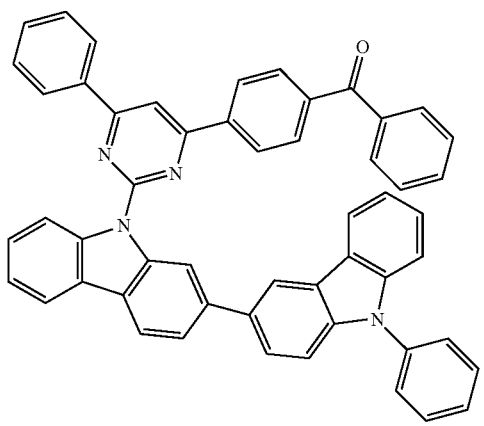
82 -continued
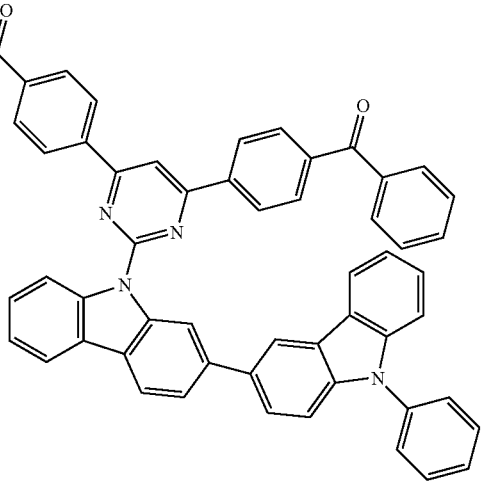
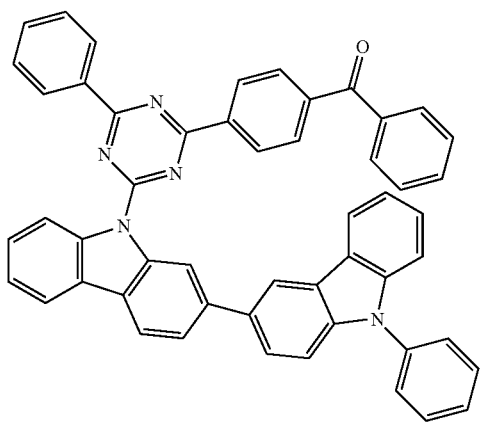
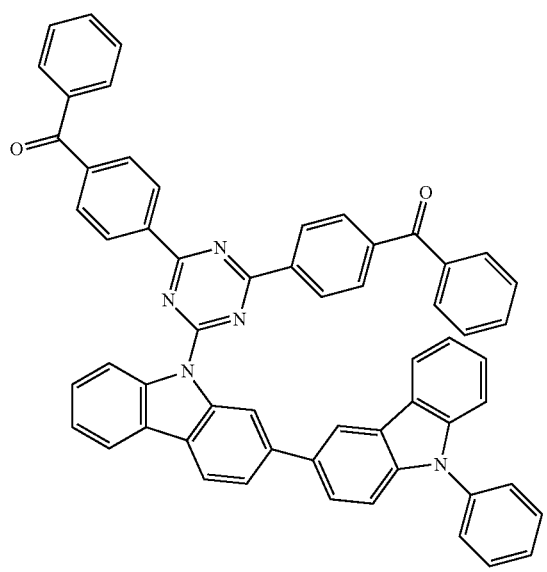
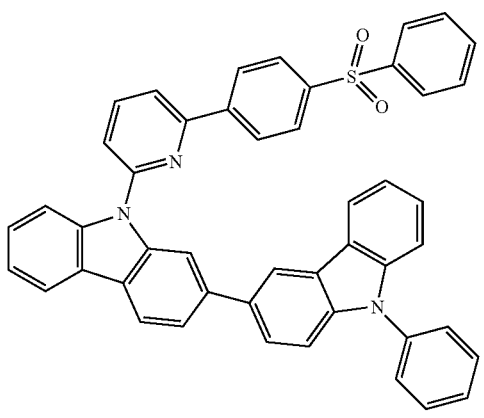
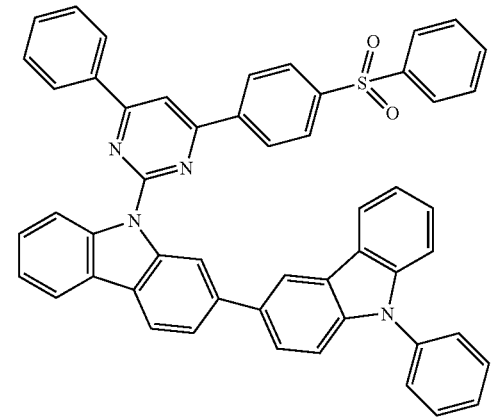

-continued
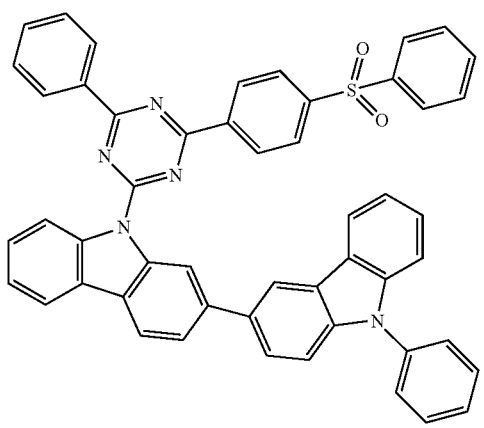
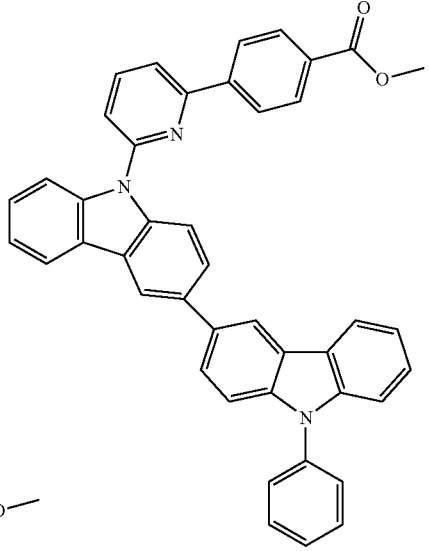
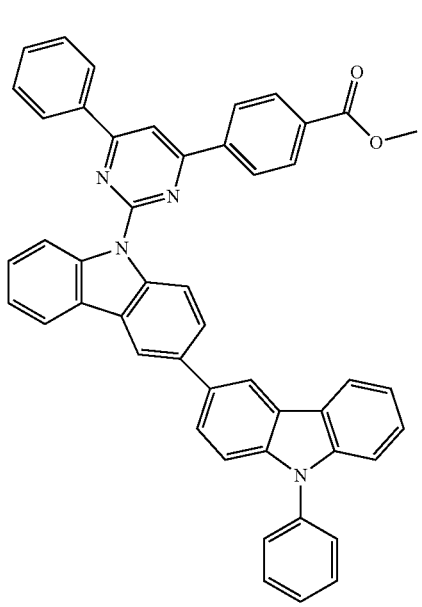
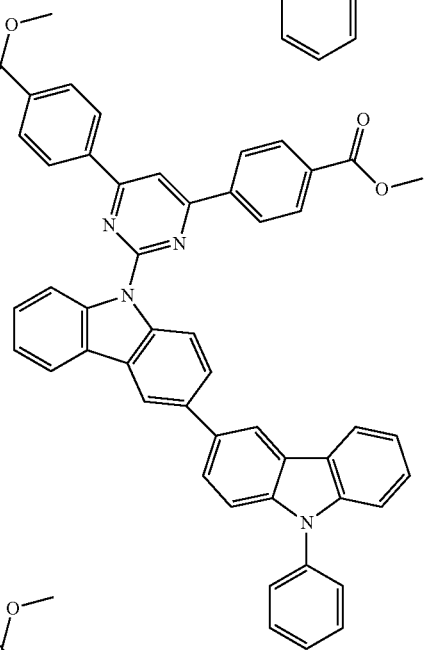
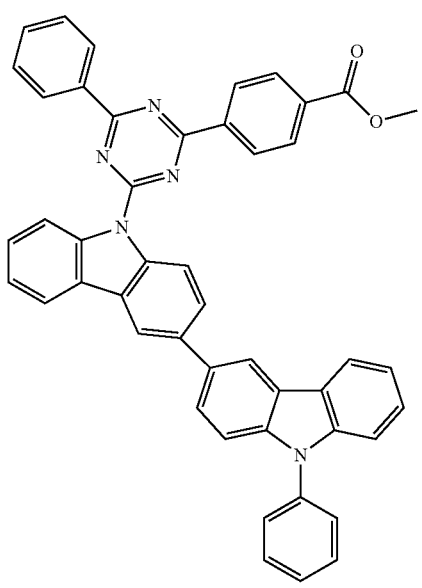
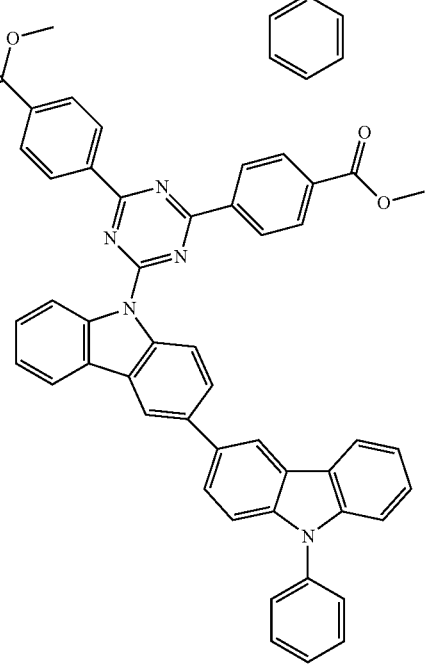

85
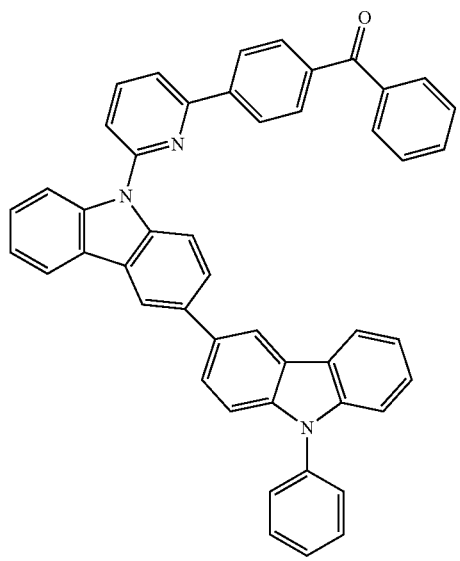
86
-continued
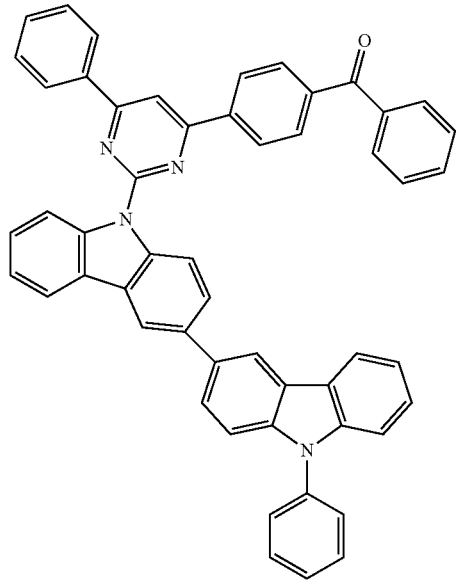
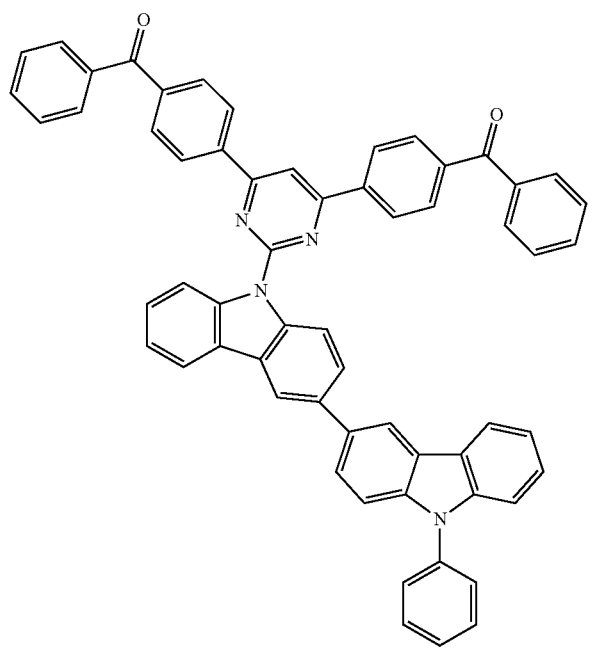
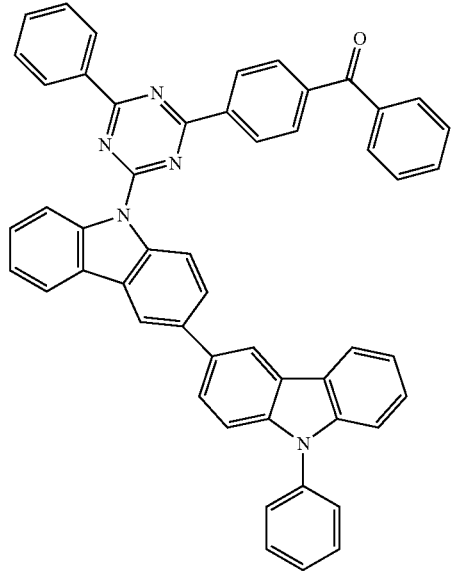

-continued
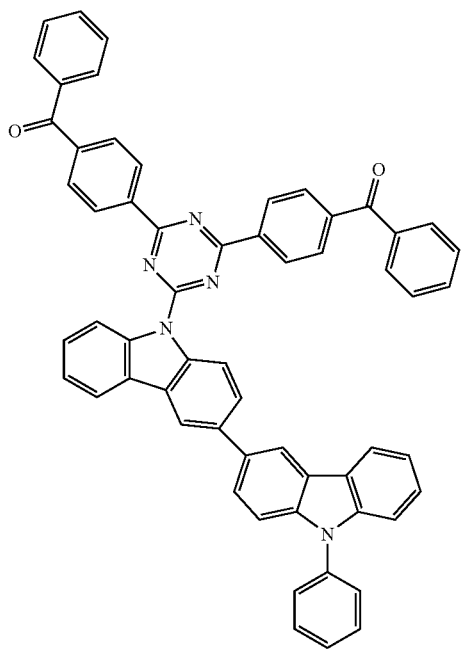
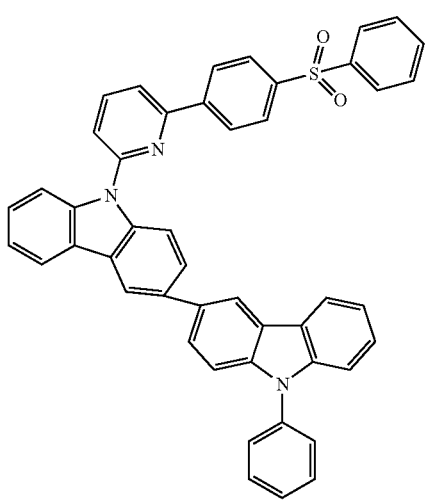
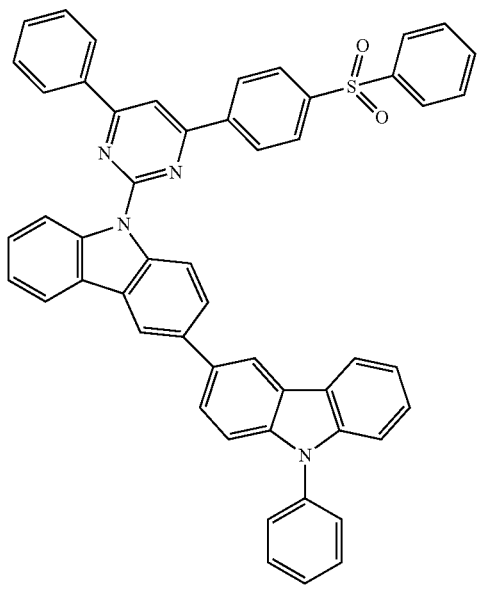
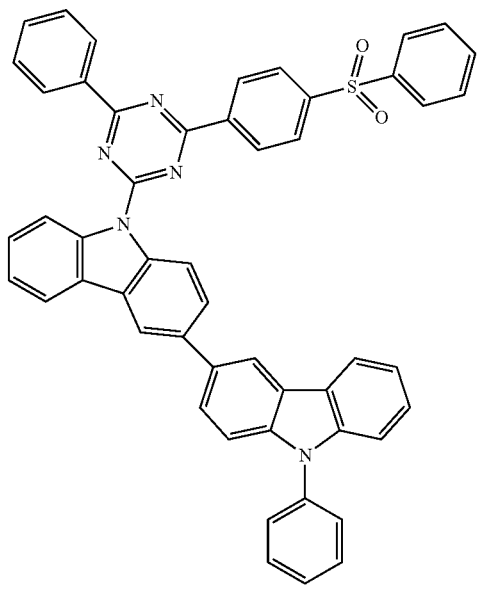
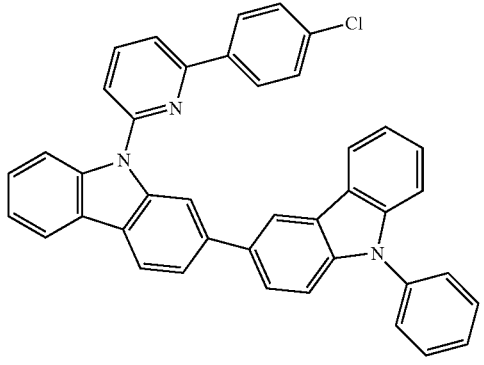
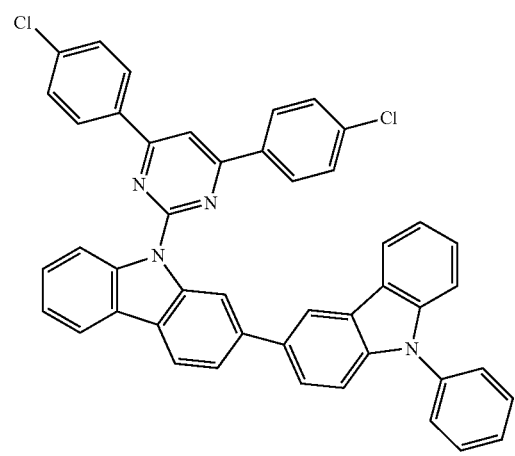

-continued
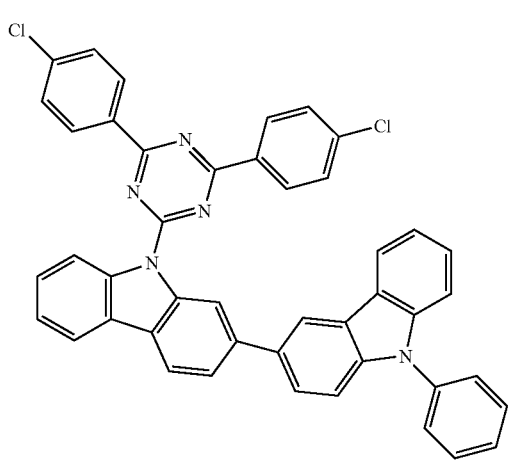
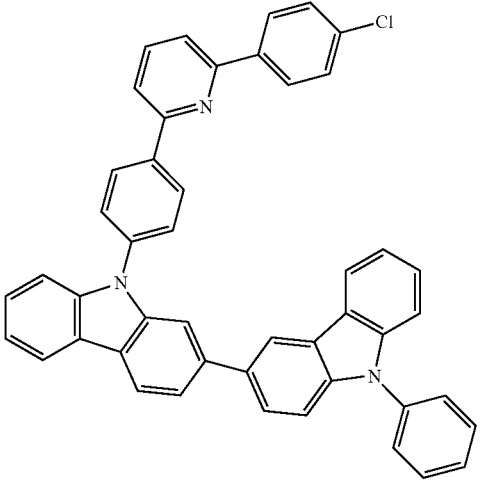
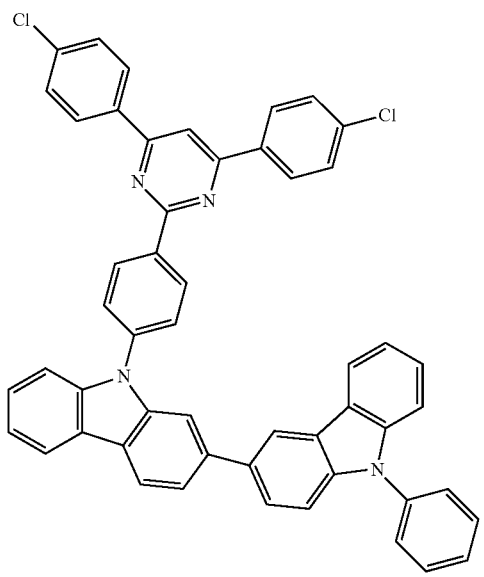
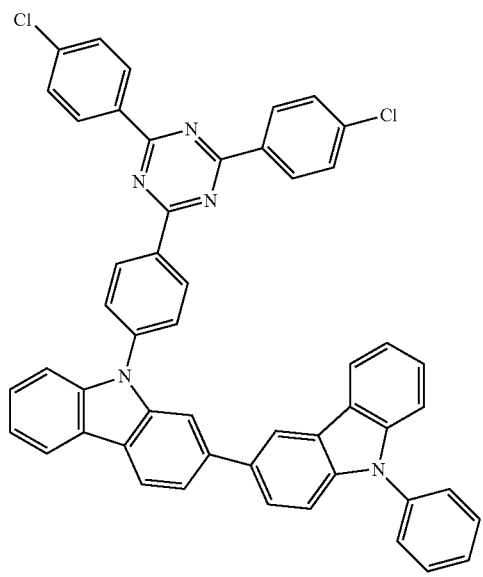
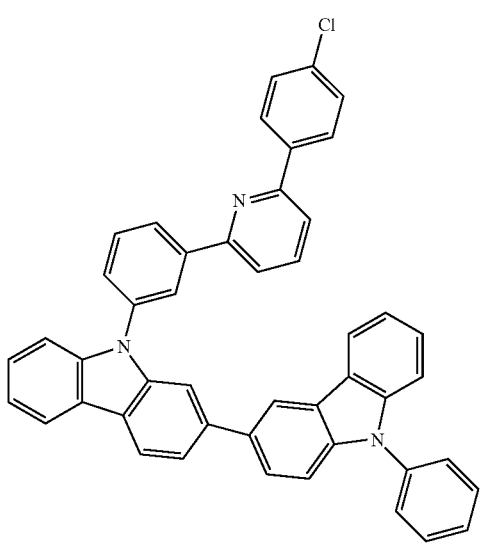
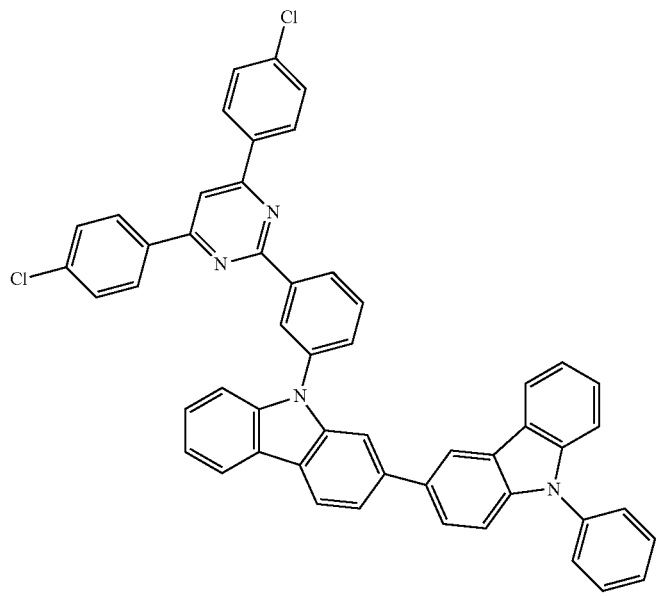

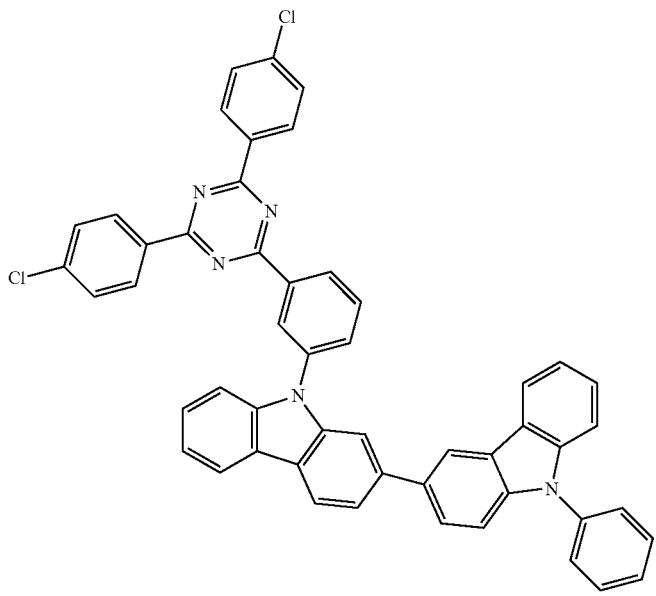
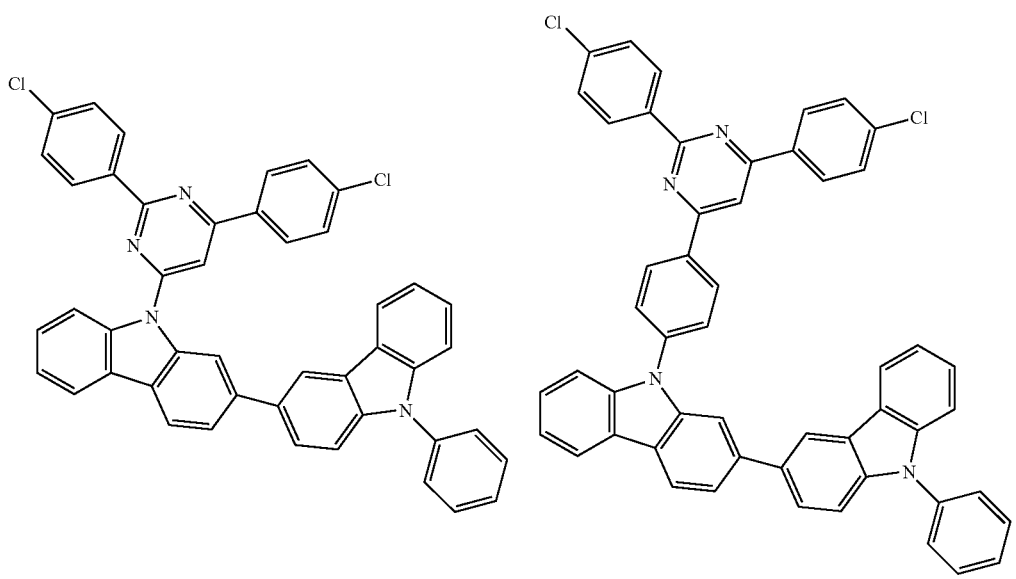

93 94
-continued
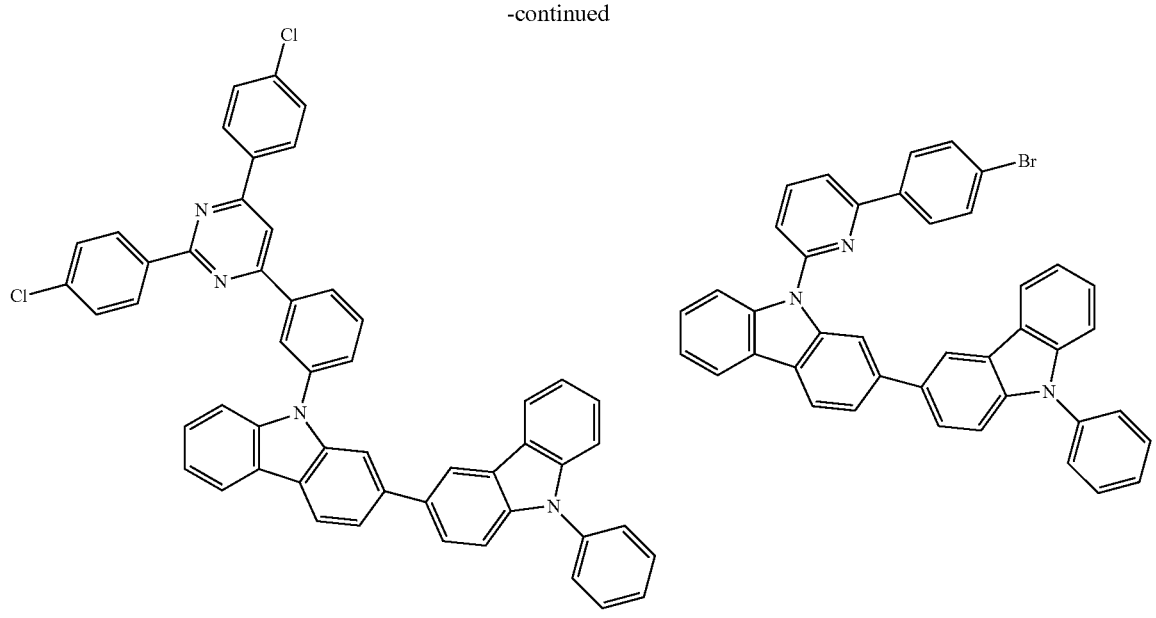
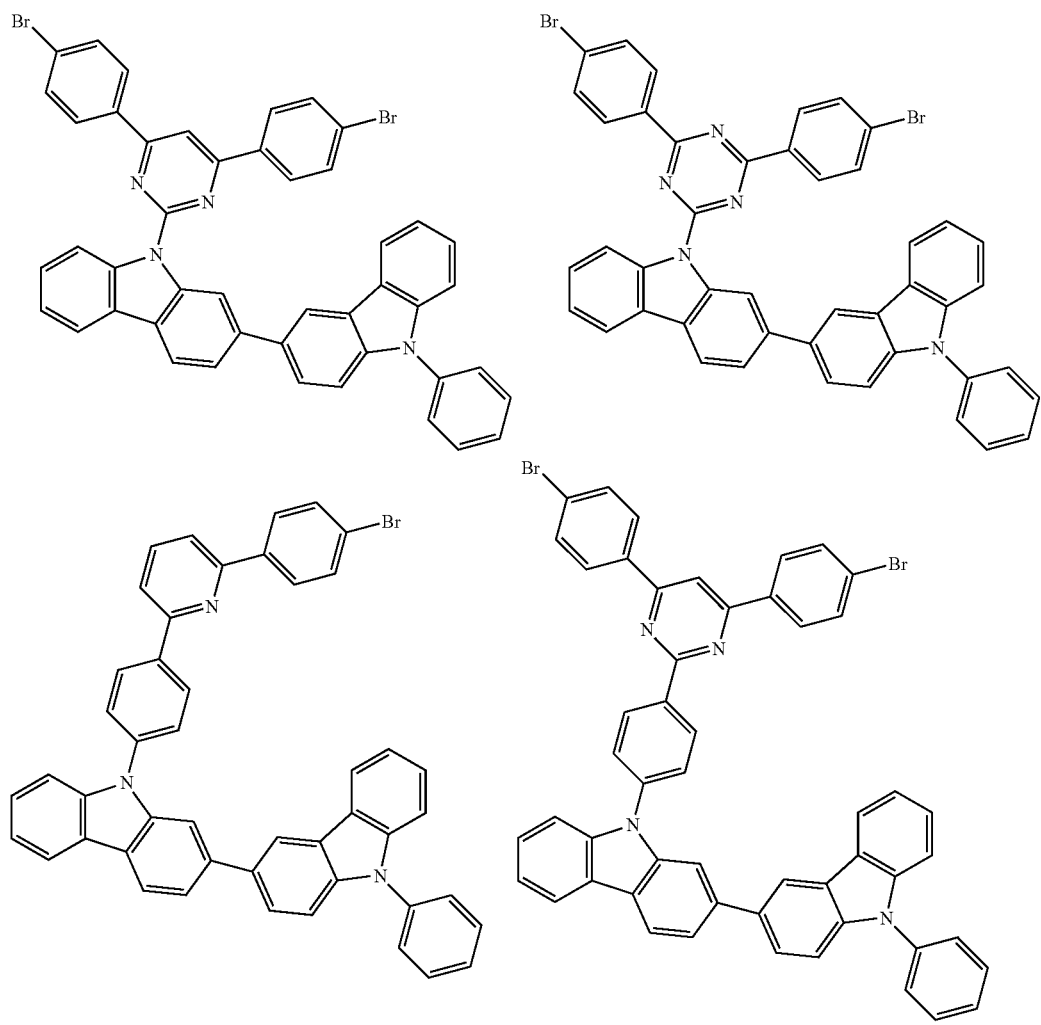

-continued
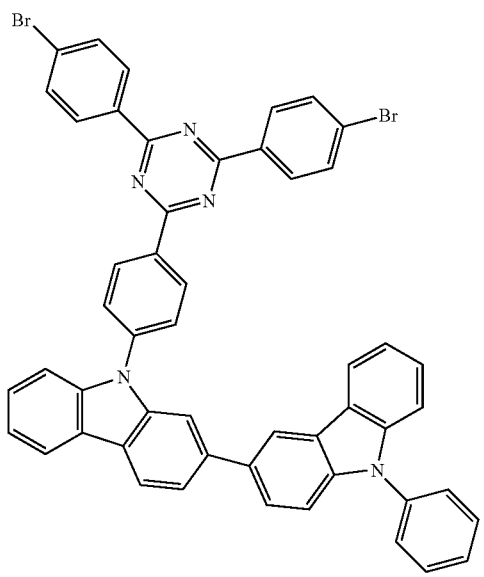
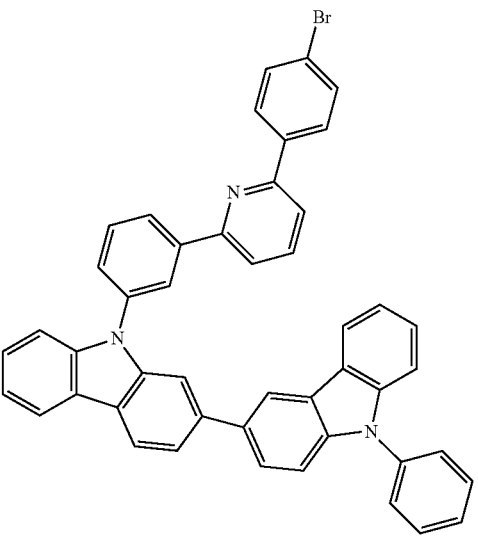
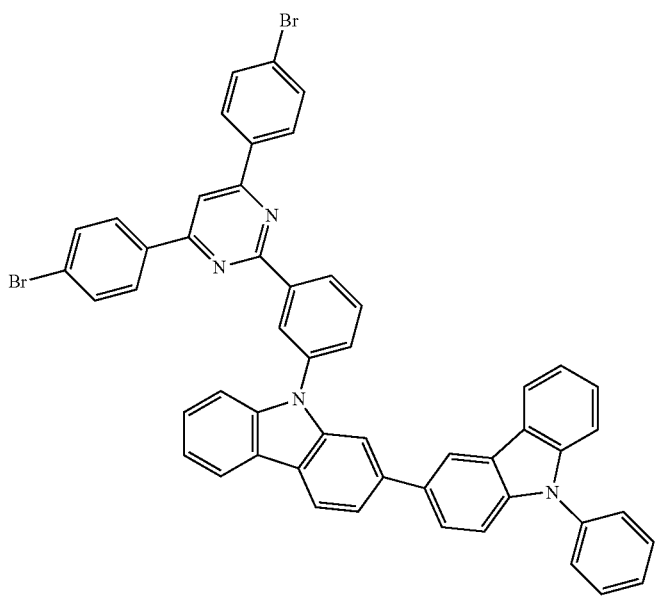

-continued
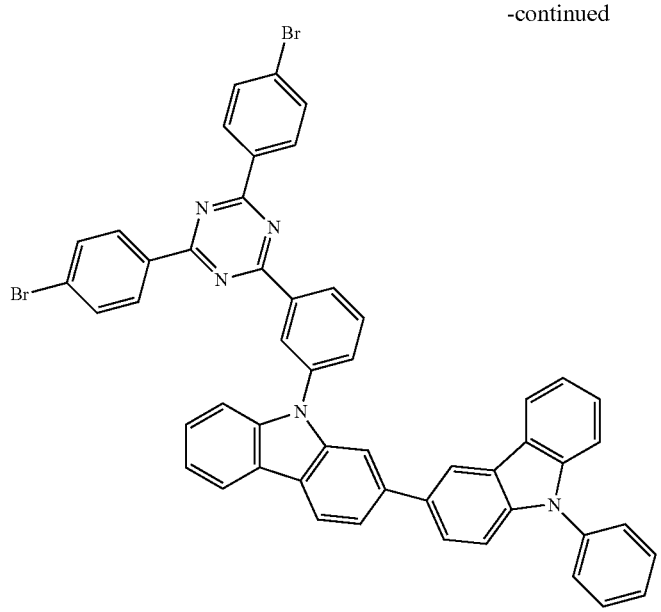
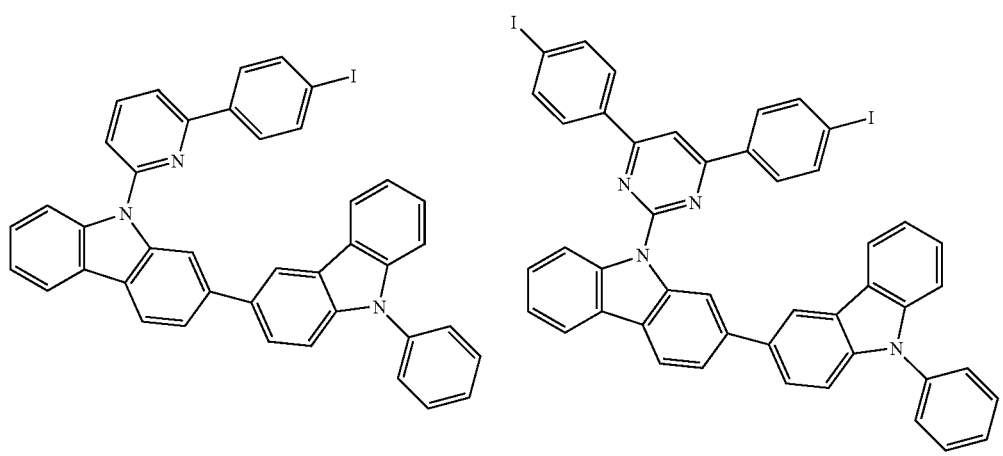
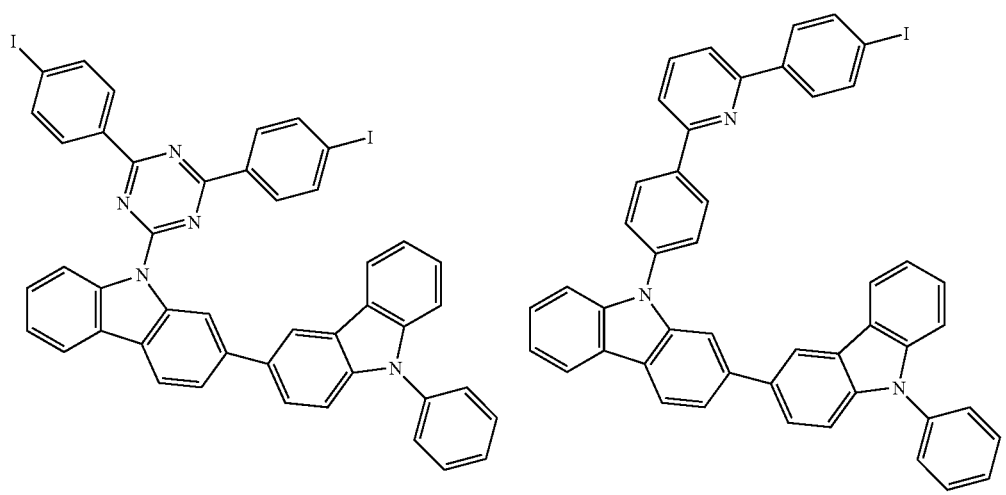

-continued
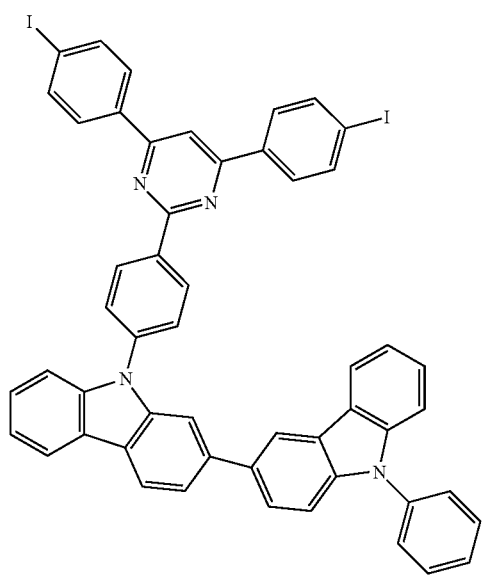
99
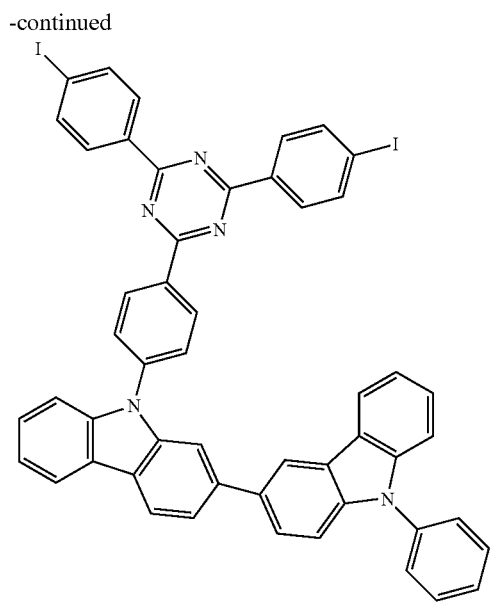
100
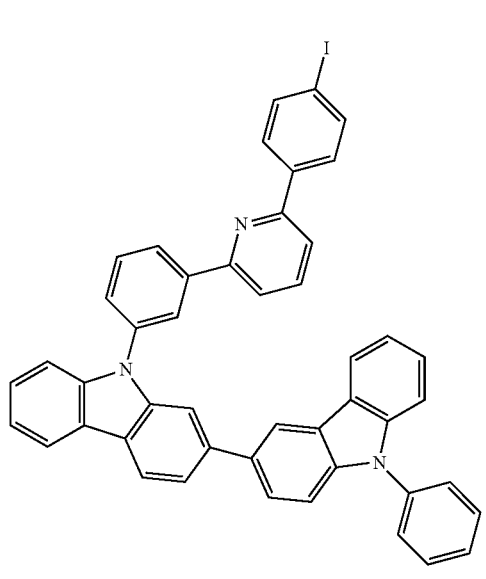
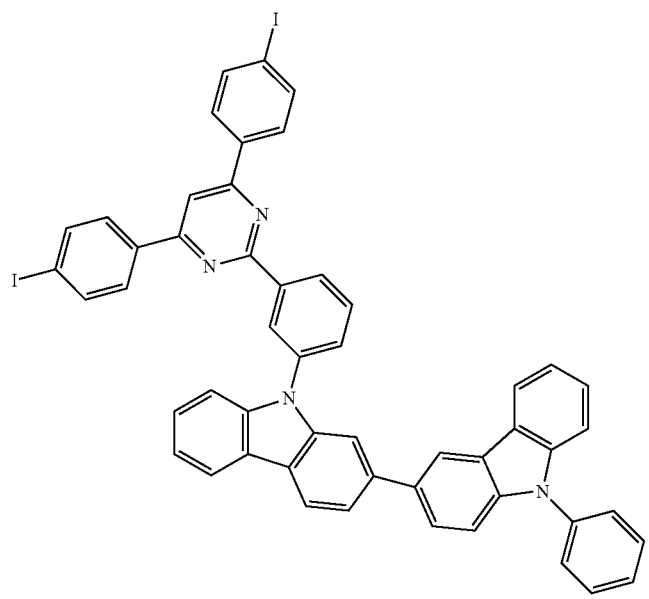

-continued
101
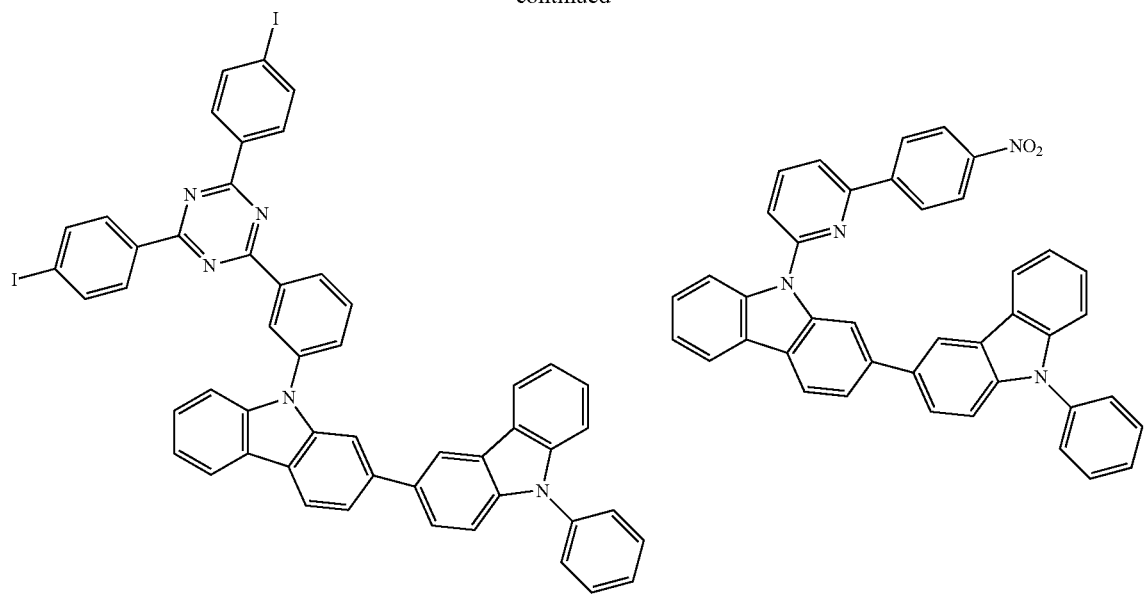
102
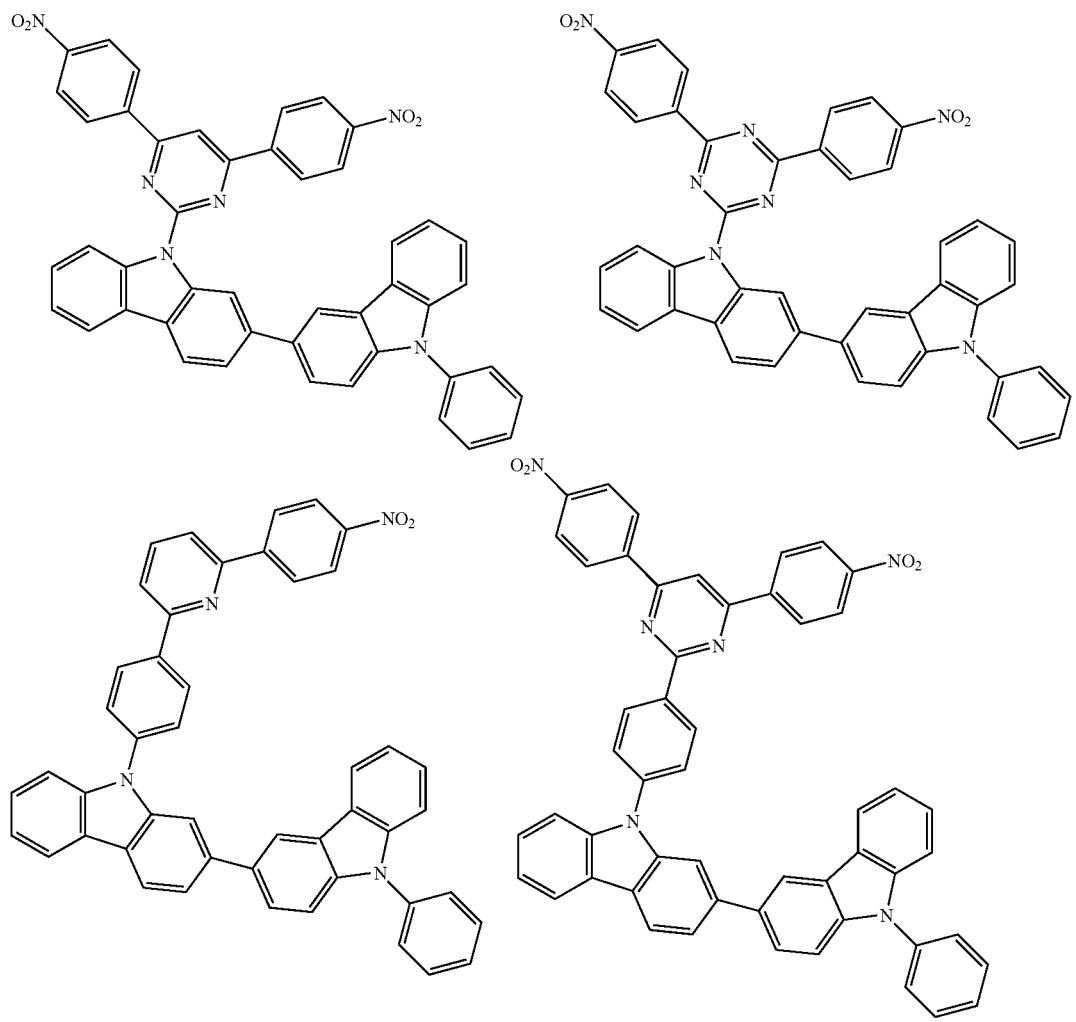

103
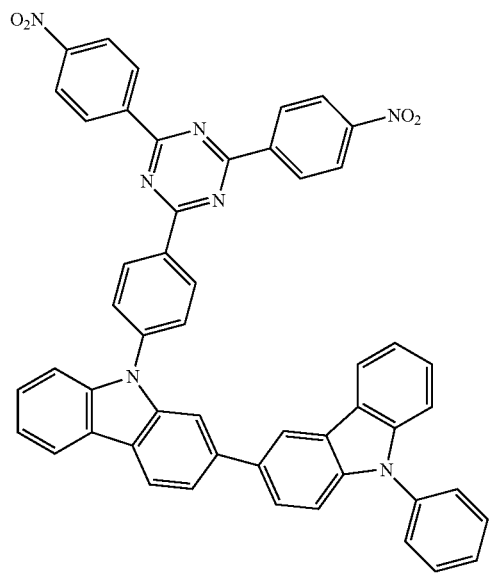
104
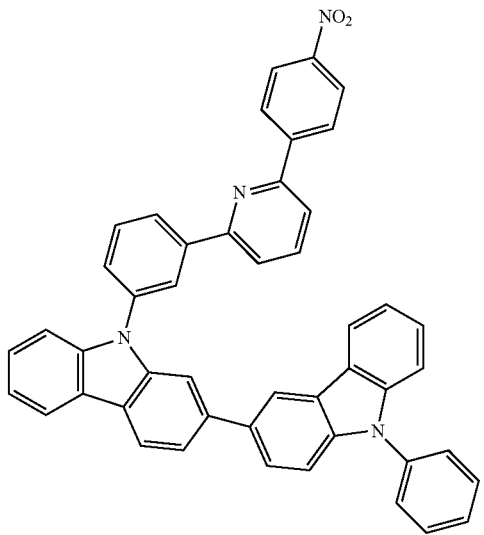
-continued
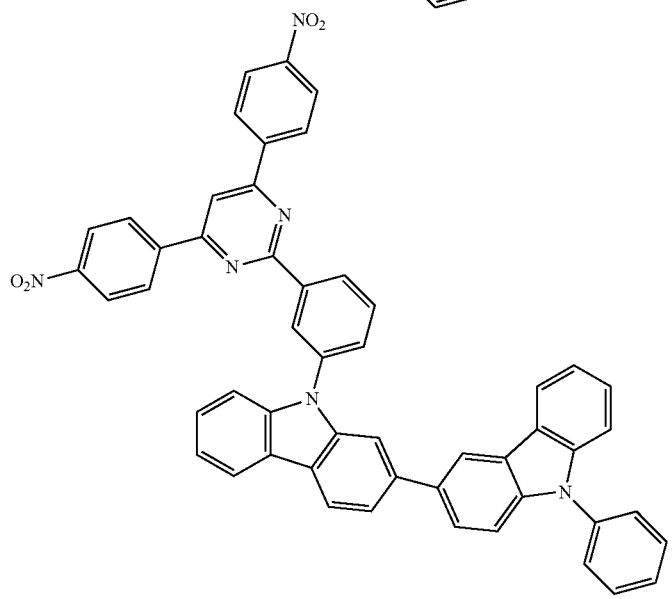
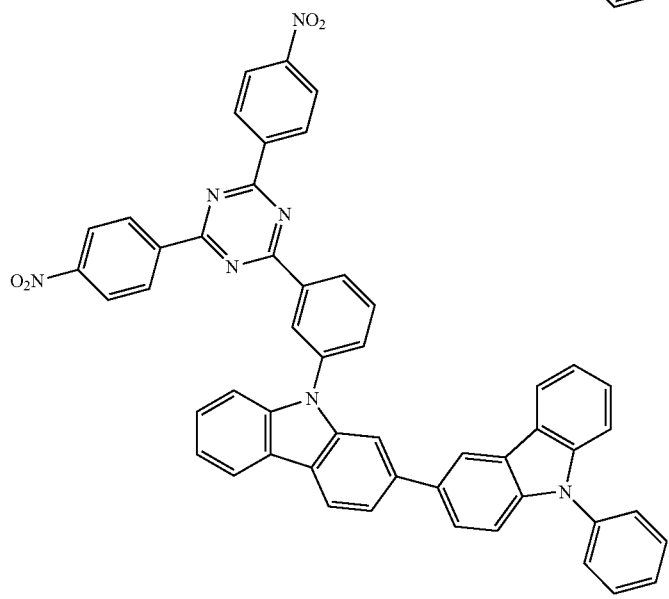

Organic EL Device

The embodiments of the organic EL device of the invention are described below.

The organic EL device of the invention comprises organic thin film layers between a cathode and an anode. The organic thin film layers includes a light emitting layer. By using the material for organic EL device of the invention in at least one layer of the organic thin film layers, the lifetime of the organic EL device is prolonged.

The material for organic EL device of the invention may be used in an organic thin film layer, such as a hole transporting layer, a light emitting layer, an electron transporting layer, a space layer, and a blocking layer, although not limited thereto. The material for organic EL device of the invention is preferably used in a light emitting layer and particularly preferably in a light emitting layer as a host material. The light emitting layer preferably further comprises a fluorescent emitting material or a phosphorescent emitting material, particularly preferably a phosphorescent emitting material. The material for organic EL device of the invention is useful as a material for a blocking layer.

The organic EL device of the invention may be any of a single color emitting device of fluorescent or phosphorescent type, a white-emitting device of fluorescent-phosphorescent hybrid type, an emitting device of a simple type having a single emission unit, and an emitting device of a tandem type having two or more emission units, with the phosphorescent device being preferred. The "emission unit" referred to herein is the smallest unit for emitting light by the recombination of injected holes and injected electrons, which comprises one or more organic layers wherein at least one layer is a light emitting layer.

Representative device structures of the simple-type organic EL device are shown below.

(1) Anode/Emission Unit/Cathode

The emission unit may be a laminate comprising two or more layers selected from a phosphorescent light emitting layer and a fluorescent light emitting layer. A space layer may be disposed between the light emitting layers to prevent the diffusion of excitons generated in the phosphorescent light emitting layer into the fluorescent light emitting layer. Representative layered structures of the emission unit are shown below.

(a) hole transporting layer/light emitting layer (/electron transporting layer);
(b) hole transporting layer/first phosphorescent light emitting layer/second phosphorescent light emitting layer (/electron transporting layer);
(c) hole transporting layer/phosphorescent light emitting layer/space layer/fluorescent light emitting layer (/electron transporting layer);
(d) hole transporting layer/first phosphorescent light emitting layer/second phosphorescent light emitting layer/space layer/fluorescent light emitting layer (/electron transporting layer);
(e) hole transporting layer/first phosphorescent light emitting layer/space layer/second phosphorescent light emitting layer/space layer/fluorescent light emitting layer (/electron transporting layer);
(f) hole transporting layer/phosphorescent light emitting layer/space layer/first fluorescent light emitting layer/second fluorescent light emitting layer (/electron transporting layer);
(g) hole transporting layer/electron blocking layer/light emitting layer (/electron transporting layer);
(h) hole transporting layer/light emitting layer/hole blocking layer (/electron transporting layer); and
(i) hole transporting layer/fluorescent light emitting layer/triplet blocking layer (/electron transporting layer).

The emission color of the phosphorescent light emitting layer and that of the fluorescent light emitting layer may be different. For example, the layered structure of the laminated light emitting layer (d) may be hole transporting layer/first phosphorescent light emitting layer (red emission)/second phosphorescent light emitting layer (green emission)/space layer/fluorescent light emitting layer (blue emission)/electron transporting layer.

An electron blocking layer may be disposed between the light emitting layer and the hole transporting layer or between the light emitting layer and the space layer, if necessary. Also, a hole blocking layer may be disposed between the light emitting layer and the electron transporting layer, if necessary. With such a electron blocking layer or a hole blocking layer, electrons and holes are confined in the light emitting layer to increase the degree of charge recombination in the light emitting layer, thereby improving the lifetime.

Representative device structure of the tandem-type organic EL device is shown below.

(2) Anode/First Emission Unit/Intermediate Layer/Second Emission Unit/Cathode

The layered structure of the first emission unit and the second emission unit may be selected from those described above with respect to the emission unit.

Generally, the intermediate layer is also called an intermediate electrode, an intermediate conductive layer, a charge generation layer, an electron withdrawing layer, a connecting layer, or an intermediate insulating layer. The intermediate layer may be formed by known materials so as to supply electrons to the first emission unit and holes to the second emission unit.

A schematic structure of an example of the organic EL device of the invention is shown in FIG. 1 wherein the organic EL device 1 is constructed by a substrate 2, an anode 3, a cathode 4, and an emission unit 10 (organic thin film layer) disposed between the anode 3 and the cathode 4. The emission unit 10 includes a light emitting layer 5 which comprises at least one phosphorescent emitting layer containing a phosphorescent host material and a phosphorescent dopant material. A hole injecting/transporting layer 6, etc. may be disposed between the light emitting layer 5 and the anode 3, and an electron injecting/transporting layer 7, etc. may be disposed between the light emitting layer 5 and the cathode 4. An electron blocking layer may be disposed on the anode 3 side of the light emitting layer 5, and a hole blocking layer may be disposed on the cathode 4 side of the light emitting layer 5. With these blocking layers, electrons and holes are confined in the light emitting layer 5 to increase the degree of exciton generation in the light emitting layer 5.

In the present invention, a host is referred to as a fluorescent host when combinedly used with a fluorescent dopant and as a phosphorescent host when combinedly used with a phosphorescent dopant. Therefore, the fluorescent host and the phosphorescent host are not distinguished from each other merely by the difference in their molecular structures. Namely, in the present invention, the term "phosphorescent host" means a material for constituting a phosphorescent emitting layer containing a phosphorescent dopant and does not mean a material that cannot be utilized as a material for a fluorescent emitting layer. The same applies to the fluorescent host.

Substrate

The organic EL device of the invention is formed on a light-transmissive substrate. The light-transmissive substrate serves as a support for the organic EL device and preferably a flat substrate having a transmittance of 50% or more to 400 to 700 nm visible light. Examples of the substrate include a glass plate and a polymer plate. The glass plate may include a plate made of soda-lime glass, barium-strontium-containing glass, lead glass, aluminosilicate glass, borosilicate glass, barium borosilicate glass, or quartz. The polymer plate may include a plate made of polycarbonate, acryl, polyethylene terephthalate, polyether sulfide, or polysulfone.

Anode

The anode of the organic EL device injects holes to the hole transporting layer or the light emitting layer, and an anode having a work function of 4.5 eV or more is effective. Examples of the material for anode include indium tin oxide alloy (ITO), tin oxide (NESA), indium zinc oxide alloy, gold, silver, platinum, and cupper. The anode is formed by making the electrode material into a thin film by a method, such as a vapor deposition method or a sputtering method. When getting the light emitted from the light emitting layer through the anode, the transmittance of anode to visible light is preferably 10% or more. The sheet resistance of anode is preferably several hundreds $\Omega/\square$ or less. The film thickness of anode depends upon the kind of material and generally 10 nm to 1 μm, preferably 10 to 200 nm.

Cathode

The cathode injects electrons to the electron injecting layer, the electron transporting layer or the light emitting layer, and formed preferably by a material having a small work function. Examples of the material for cathode include, but not limited to, indium, aluminum, magnesium, magnesium-indium alloy, magnesium-aluminum alloy, aluminum-lithium alloy, aluminum-scandium-lithium alloy, and magnesium-silver alloy. Like the anode, the cathode is formed by making the material into a thin film by a method, such as the vapor deposition method and the sputtering method. The emitted light may be taken through the cathode, if necessary.

Light Emitting Layer

The light emitting layer is an organic layer having a light emitting function and contains a host material and a dopant material when a doping system is employed. The major function of the host material is to promote the recombination of electrons and holes and confine excitons in the light emitting layer. The dopant material causes the excitons generated by recombination to emit light efficiently.

In case of a phosphorescent device, the major function of the host material is to confine the excitons generated on the dopant in the light emitting layer.

To control the carrier balance in the light emitting layer, the light emitting layer may be made into a double host (host/co-host) layer, for example, by combinedly using an electron transporting host and a hole transporting host. In a preferred embodiment, the light emitting layer comprises a first host material and a second host material, wherein the first host material is the material for organic EL device of the invention.

The light emitting layer may be made into a double dopant layer, in which two or more kinds of dopant materials having high quantum yield are combinedly used and each dopant material emits light with its own color. For example, to obtain a yellow emission, a light emitting layer formed by co-depositing a host, a red-emitting dopant and a green-emitting dopant is used.

In a laminate of two or more light emitting layers, electrons and holes are accumulated in the interface between the light emitting layers, and therefore, the recombination region is localized in the interface between the light emitting layers, to improve the quantum efficiency.

The easiness of hole injection to the light emitting layer and the easiness of electron injection to the light emitting layer may be different from each other. Also, the hole transporting ability and the electron transporting ability each being expressed by mobility of holes and electrons in the light emitting layer may be different from each other.

The light emitting layer is formed, for example, by a known method, such as a vapor deposition method, a spin coating method, and LB (Langmuir Blodgett) method. The light emitting layer can be formed also by making a solution of a binder, such as resin, and the material for the light emitting layer in a solvent into a thin film by a method such as spin coating.

The light emitting layer is preferably a molecular deposit film. The molecular deposit film is a thin film formed by depositing a vaporized material or a film formed by solidifying a material in the state of solution or liquid. The molecular deposit film can be distinguished from a thin film formed by LB method (molecular build-up film) by the differences in the assembly structures and higher order structures and the functional difference due to the structural differences.

The dopant material is selected from known fluorescent dopants and phosphorescent dopants.

Examples of the fluorescent dopant include fluoranthene derivative, pyrene derivative, arylacetylene derivative, fluorene derivative, boron complex, perylene derivative, oxadiazole derivative, anthracene derivative, and chrysene derivative, with fluoranthene derivative, pyrene derivative, and boron complex being preferred.

The phosphorescent dopant (phosphorescent emitting material) used in the light emitting layer is a compound which emits light by releasing the energy of excited triplet state and preferably a organometallic complex comprising at least one metal selected from Ir, Pt, Os, Au, Cu, Re, and Ru and a ligand, although not particularly limited thereto as long as emitting light by releasing the energy of excited triplet state. The ligand is preferably ortho-metallated. In view of obtaining a high phosphorescent quantum yield and further improving the external quantum efficiency of organic EL device, a metal complex comprising a metal selected from Ir, Os, and Pt is preferred, with a metal complex, particularly an ortho-metallated complex, such as an iridium complex, an osmium complex, and a platinum complex, being more preferred, an iridium complex and a platinum complex being still more preferred, and an ortho-metallated iridium complex being particularly preferred.

The content of the phosphorescent dopant in the light emitting layer is not particularly limited and selected according to the use of the device, and preferably 0.1 to 70% by mass, and more preferably 1 to 30% by mass. If being 0.1% by mass or more, the amount of light emission is sufficient. If being 70% by mass or less, the concentration quenching can be avoided.

Preferred examples of the organometallic complex for the phosphorescent dopant are shown below.
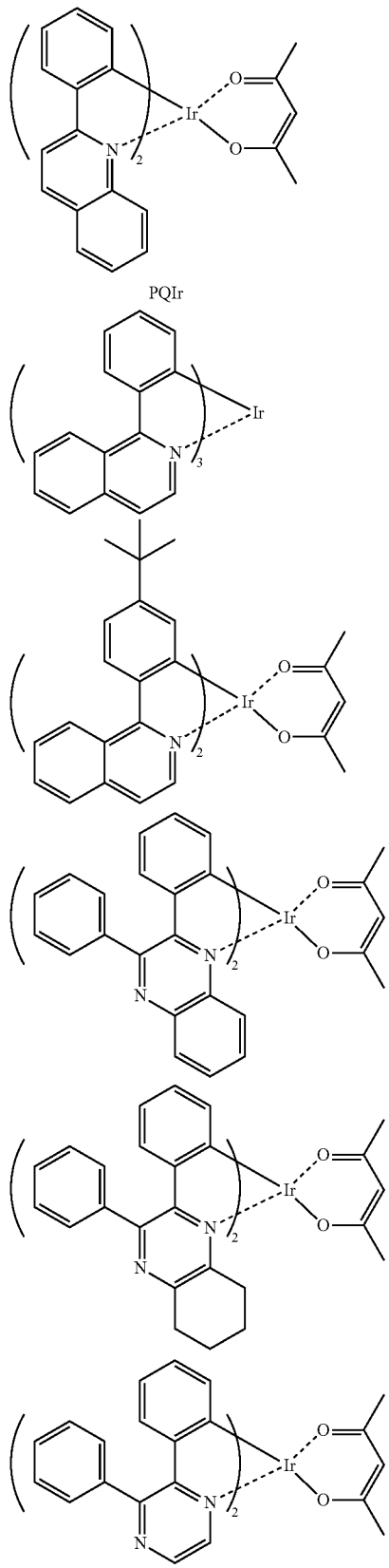
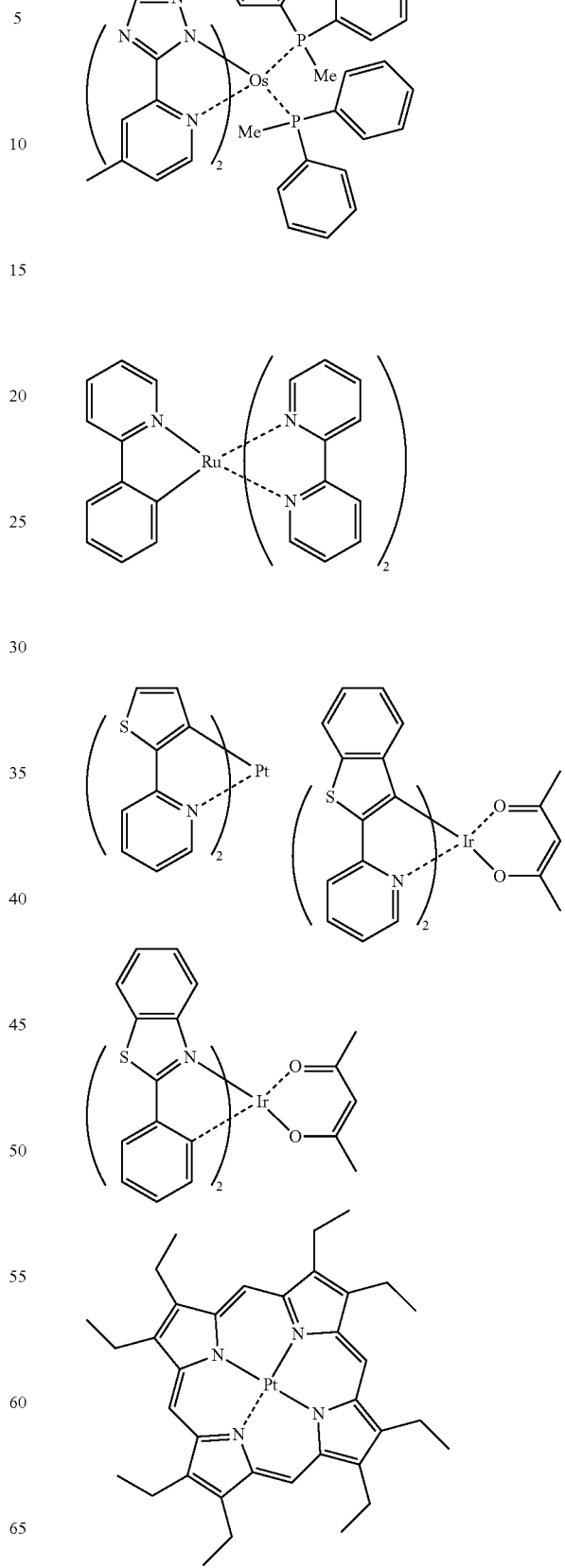

111
-continued
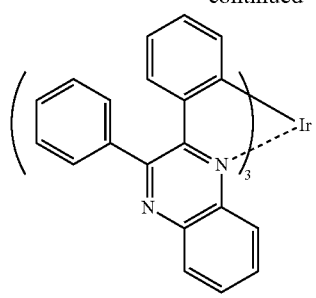
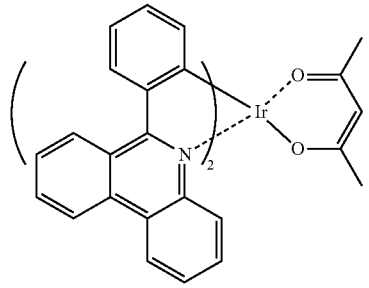
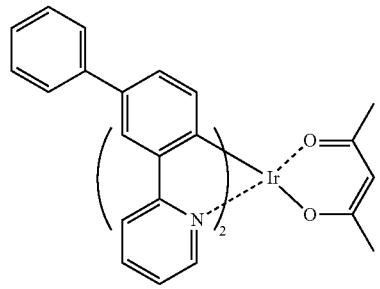
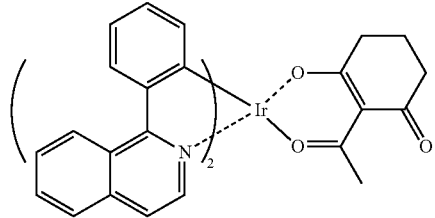
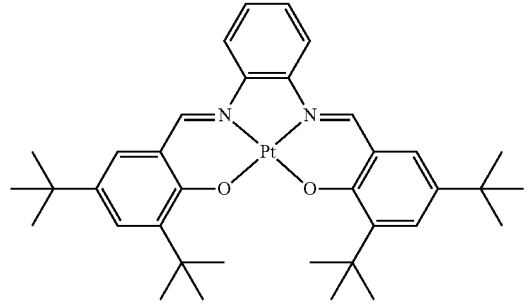
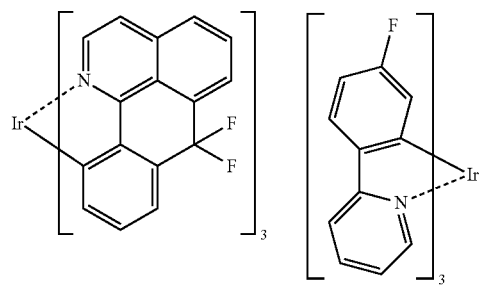
112
-continued
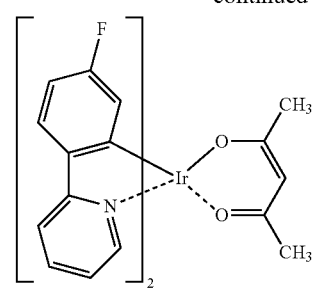
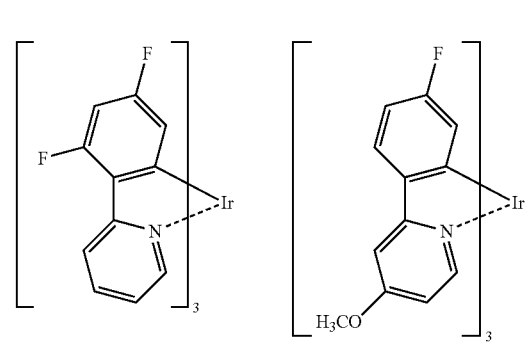
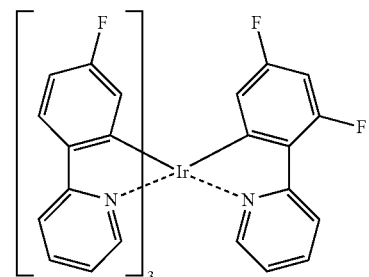
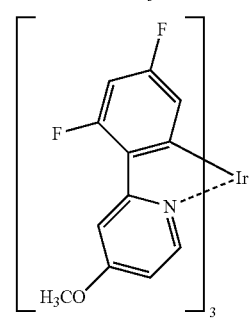
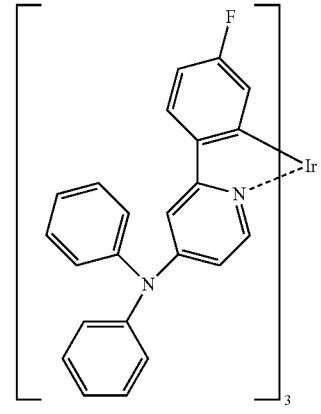

-continued
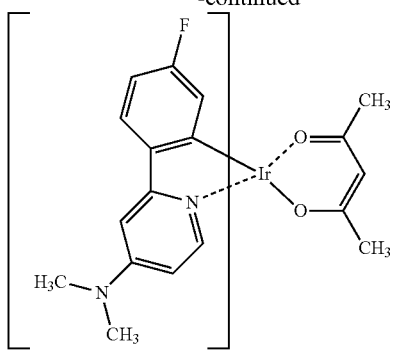
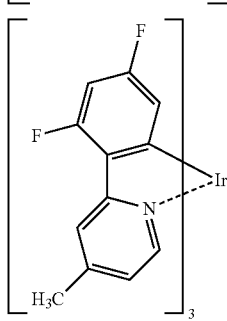
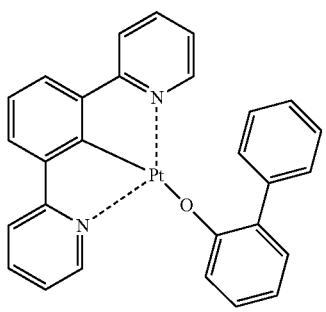
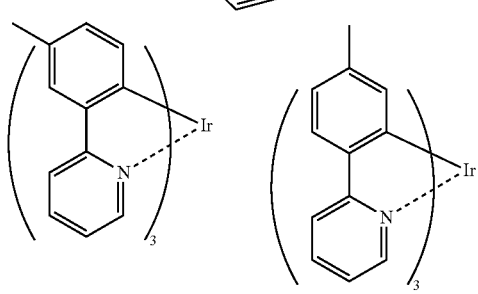
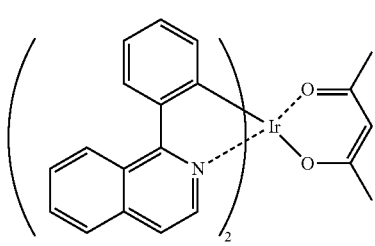
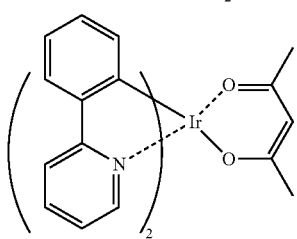
-continued
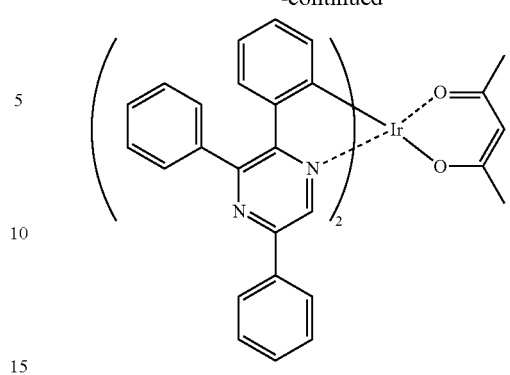
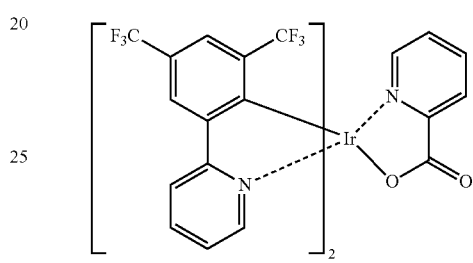
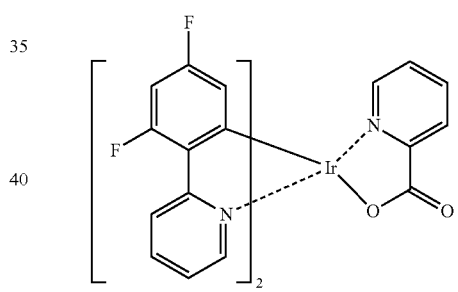
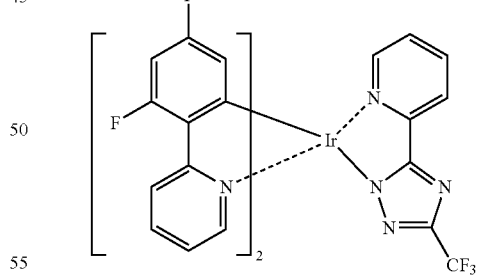
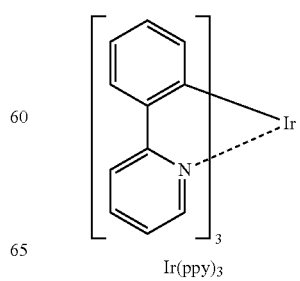
Ir(ppy)$_3$

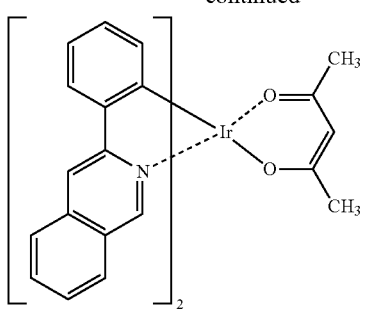
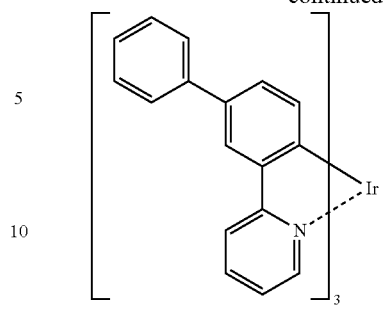
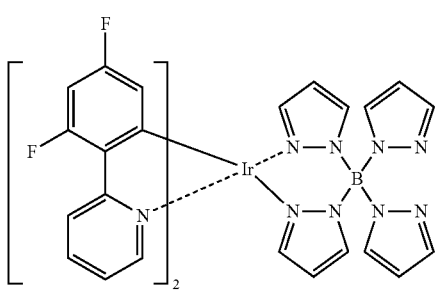
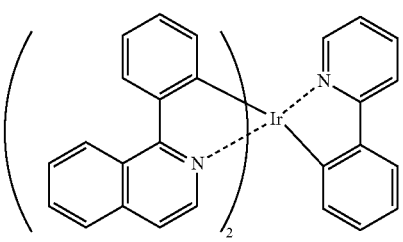
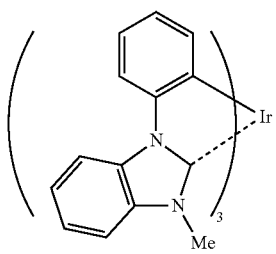
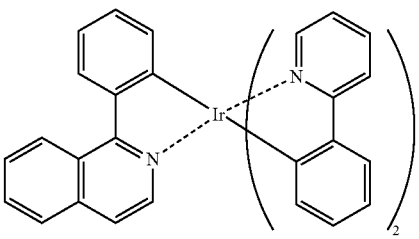
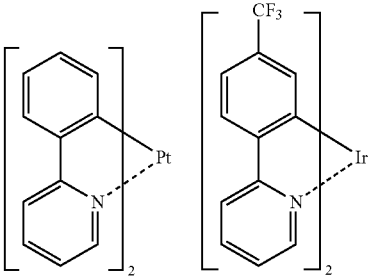
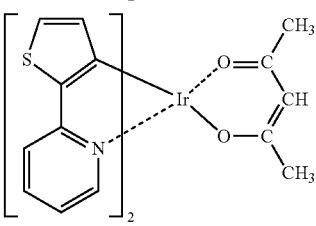
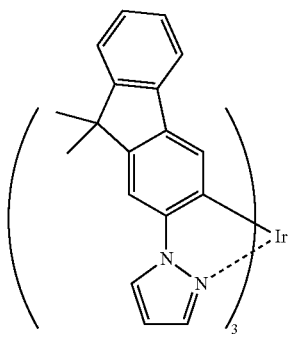
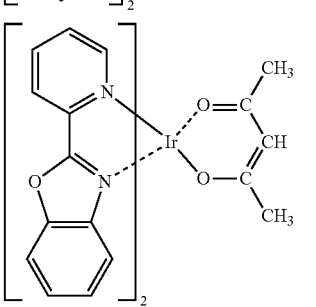

-continued

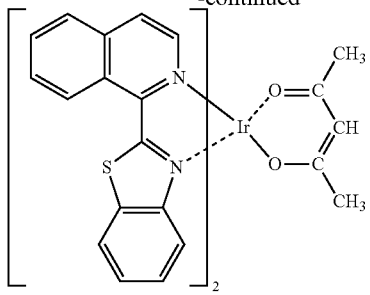

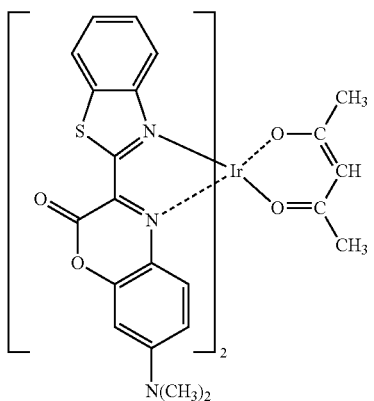

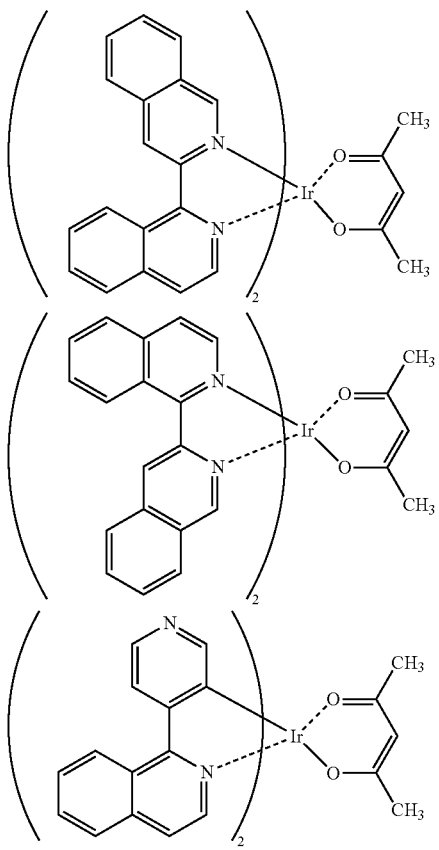

-continued

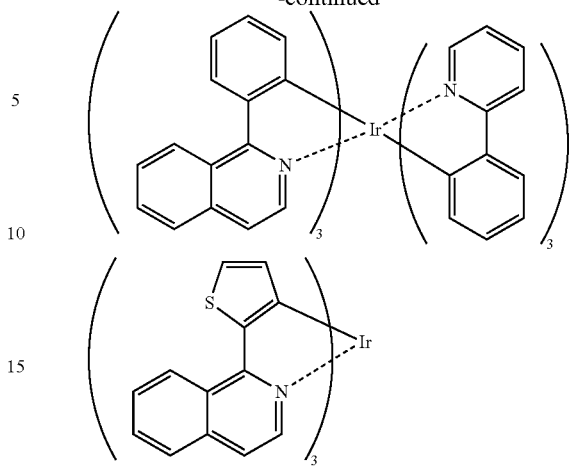

The phosphorescent host is a compound which confines the triplet energy of the phosphorescent dopant efficiently in the light emitting layer to cause the phosphorescent dopant to emit light efficiently. The material for organic EL device of the invention is useful as a phosphorescent host. The light emitting layer may comprise one or more kinds of the material for organic EL device of the invention.

When the material for organic EL device of the invention is used in the light emitting layer as a host material, the emission wavelength of the phosphorescent dopant used is not particularly limited. In a preferred embodiment, at least one of the phosphorescent dopants used in the light emitting layer has the peak of emission wavelength of preferably 490 nm or longer and 700 nm or shorter and more preferably 490 nm or longer and 650 nm or shorter. The emission color of the light emitting layer is preferably red, yellow and green. An organic EL device with a long lifetime can be obtained by a light emitting layer comprising the compound of the invention as the host material which is doped with a phosphorescent dopant material emitting light with a wavelength within the above ranges.

In the organic EL device of the invention, in addition to the material for organic EL device of the invention, another compound may be used as the phosphorescent host according to the use of the device.

The material for organic EL device of the invention and another compound may be combinedly used in the same light emitting layer as the phosphorescent host material. If two or more light emitting layers are formed, the material for organic EL device of the invention can be used in one of the light emitting layers as the phosphorescent host material and a compound other than the material for organic EL device of the invention can be used in another light emitting layer as the phosphorescent host material. The material for organic EL device of the invention may be used in an organic layer other than the light emitting layer. In this case, a compound other than the material for organic EL device of the invention may be used as a phosphorescent host of the light emitting layer.

Examples of the preferred phosphorescent host other than the material for organic EL device of the invention include a carbazole derivative, a triazole derivative, a oxazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, an aromatic methylidene compound, a porphyrin compound, an anthraquinodimethane derivative, an anthrone derivative, a diphenylquinone derivative, a thiopyran dioxide derivative, a carbodiimide derivative, a fluorenylidenemethane derivative, a distyrylpyrazine derivative, a tetracarboxylic anhydride of fused ring such as naphthalene and perylene, a phthalocyanine derivative, a metal complex of 8-quinolinol derivative, metal phthalocyanine, metal complexes having a ligand such as benzoxazole and benzothiazole, an electroconductive oligomer, such as a polysilane compound, a poly(N-vinylcarbazole) derivative, an aniline copolymer, thiophene oligomer, and a polythiophene, and a polymer such as a polythiophene derivative, a polyphenylene derivative, a polyphenylenevinylene derivative, and a polyfluorene derivative. These phosphorescent hosts may be used alone or in combination of two or more. Specific examples thereof are shown below.

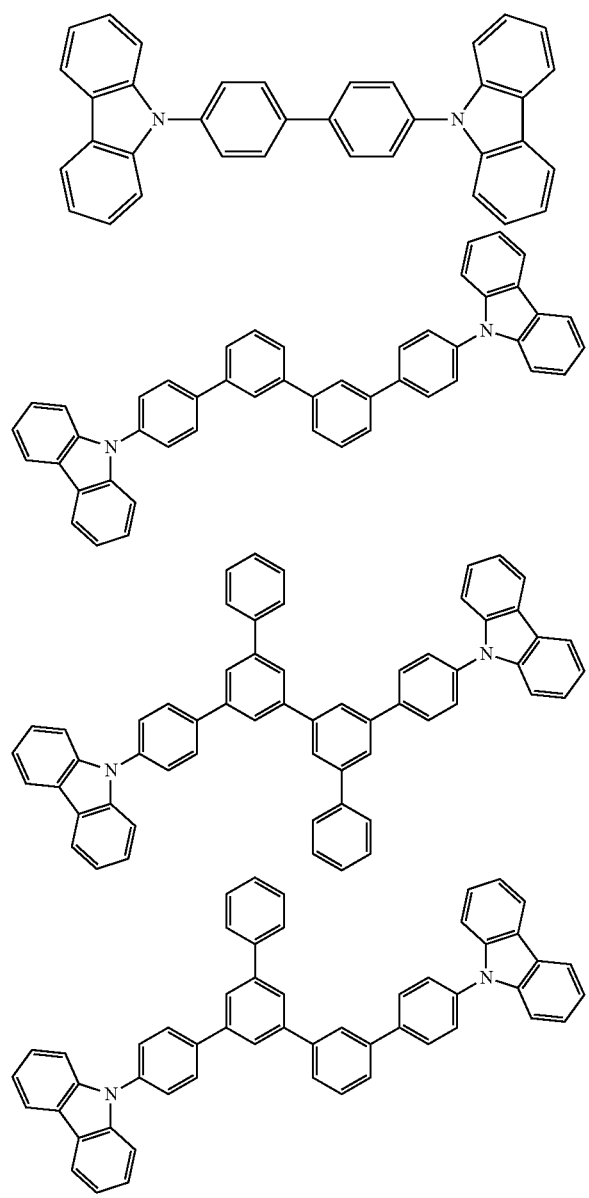

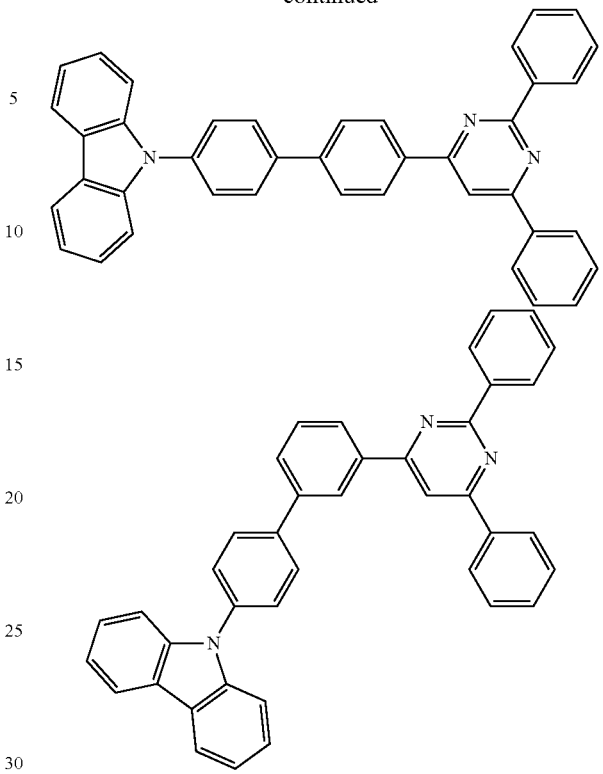

In an embodiment of the invention, the light emitting layer may comprise a first host material and a second host material, wherein the first host material is the material for organic EL device of the invention and the second host material is a compound other than the material for organic EL device of the invention. In the present invention, the terms "first host material" and "second host material" are used merely for structurally distinguishing the two or more host materials in the light emitting layer and are not determined according to the content of each host material in the light emitting layer.

The second host material is not particularly limited and may be selected from the compounds mentioned above with respect to the suitable phosphorescent host other than the material for organic EL device of the invention. A carbazole derivative, an arylamine derivative, a fluorenone derivative, an aromatic tertiary amine, and the preceding compounds having no electron-withdrawing group are preferred as the second host material.

The thickness of the light emitting layer is preferably 5 to 50 nm, more preferably 7 to 50 nm, and still more preferably 10 to 50 nm. If being 5 nm or more, the light emitting layer is easily formed. If being 50 nm or less, the increase in driving voltage is avoided.

Electron-donating Dopant

The organic EL device of the present invention preferably comprises an electron-donating dopant at an interfacial region between the cathode and the emitting unit. With such a construction, the organic EL device has an improved luminance and an elongated lifetime. The electron-donating dopant comprises a metal having a work function of 3.8 eV or less and examples thereof include at least one selected from alkali metal, alkali metal complex, alkali metal compound, alkaline earth metal, alkaline earth metal complex, alkaline earth metal compound, rare earth metal, rare earth metal complex, and rare earth metal compound.

Examples of the alkali metal include Na (work function: 2.36 eV), K (work function: 2.28 eV), Rb (work function: 2.16 eV), and Cs (work function: 1.95 eV), with those having a work function of 2.9 eV or less being particularly preferred. Of the above, preferred are K, Rb, and Cs, more preferred are Rb and Cs, and most preferred is Cs. Examples of the alkaline earth metal include Ca (work function: 2.9 eV), Sr (work function: 2.0 to 2.5 eV), and Ba (work function: 2.52 eV), with those having a work function of 2.9 eV or less being particularly preferred. Examples of the rare earth metal include Sc, Y, Ce, Tb, and Yb, with those having a work function of 2.9 eV or less being particularly preferred.

Examples of the alkali metal compound include alkali oxide, such as $Li_2O$, $Cs_2O$, $K_2O$, and alkali halide, such as LiF, NaF, CsF, and KF, with LiF, $Li_2O$, and NaF being preferred. Examples of the alkaline earth metal compound include BaO, SrO, CaO, and mixture thereof, such as $Ba_xSr_{1-x}O$ (0<x<1) and $Ba_xCA^1_{-x}O$ (0<x<1), with BaO, SrO, and CaO being preferred. Examples of the rare earth metal compound include $YbF_3$, $ScF_3$, $ScO_3$, $Y_2O_3$, $Ce_2O_3$, $GdF_3$, and $TbF_3$, with $YbF_3$, $ScF_3$, and $TbF_3$ being preferred.

Examples of the alkali metal complex, alkaline earth metal complex, and rare earth metal are not particularly limited as long as containing at least one metal ion selected from alkali metal ions, alkaline earth metal ions, rare earth metal ions, respectively. The ligand is preferably, but not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfulborane, bipyridyl, phenanthroline, phthalocyanine, porphyrin, cyclopentadiene, β-diketones, azomethines, and derivative thereof.

The electron-donating dopant is added to the interfacial region preferably into a form of layer or island. The electron-donating dopant is added preferably by co-depositing the electron-donating dopant with the organic compound (light emitting material, electron injecting material) for forming the interfacial region by a resistance heating deposition method, thereby dispersing the electron-donating dopant into the organic material. The disperse concentration expressed by the molar ratio of the organic material and the electron-donating dopant is 100:1 to 1:100 and preferably 5:1 to 1:5.

When the electron-donating dopant is formed into a form of layer, a light emitting material or an electron injecting material is made into a layer which serves as an organic layer in the interface, and then, the electron-donating dopant alone is deposited by a resistance heating deposition method into a layer having a thickness preferably 0.1 to 15 nm. When the electron-donating dopant is formed into a form of island, a light emitting material or an electron injecting material is made into a form of island which serves as an organic layer in the interface, and then, the electron-donating dopant alone is deposited by a resistance heating deposition method into a form of island having a thickness preferably 0.05 to 1 nm.

The molar ratio of the main component and the electron-donating dopant in the organic electroluminescence device of the invention is preferably 5:1 to 1:5 and more preferably 2:1 to 1:2.

Electron Transporting Layer

The electron transporting layer is an organic layer disposed between the light emitting layer and the cathode and transports electrons from the cathode to the light emitting layer. If two or more electron transporting layers are provided, the organic layer closer to the cathode may be called an electron injecting layer in some cases. The electron injecting layer injects electrons from the cathode to the organic layer unit efficiently.

An aromatic heterocyclic compound having one or more heteroatoms in a molecule thereof is preferably used as an electron transporting material used in the electron transporting layer, and a nitrogen-containing ring derivative is particularly preferred. In addition, the nitrogen-containing ring derivative is preferably an aromatic ring compound having a nitrogen-containing, 6- or 5-membered ring, or a fused aromatic ring compound having a nitrogen-containing, 6- or 5-membered ring.

The nitrogen-containing ring derivative is preferably, for example, a metal chelate complex of a nitrogen-containing ring represented by formula (A):

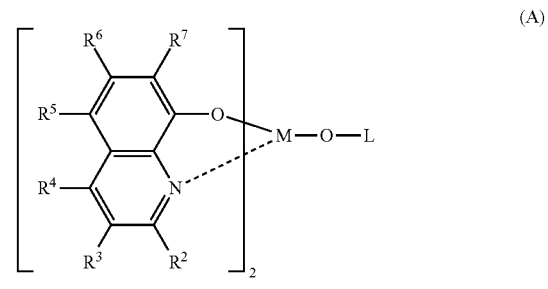

wherein each of $R^2$ to $R^7$ independently represents a hydrogen atom, a halogen atom, a hydroxyl group, an amino group, a hydrocarbon group having 1 to 40 carbon atoms, an alkoxy group having 1 to 40 carbon atoms, an aryloxy group having 6 to 50 carbon atoms, an alkoxycarbonyl group, or an aromatic heterocyclic group having 5 to 50 ring carbon atoms, each being optionally substituted.

The halogen atom may include fluorine, chlorine, bromine, and iodine.

The substituted amino group may include an alkylamino group, an arylamino group, and an aralkylamino group.

The alkylamino group and the aralkylamino group are represented by $-NQ^1Q^2$. Each of $Q^1$ and $Q^2$ independently represents an alkyl group having 1 to 20 carbon atoms or an aralkyl group having 1 to 20 carbon atoms. One of $Q^1$ and $Q^2$ may be a hydrogen atom.

The arylamino group is represented by $-NAr^1Ar^2$, wherein each of $Ar^1$ and $Ar^2$ independently represents a non-fused aromatic hydrocarbon groups or a fused aromatic hydrocarbon groups, each having 6 to 50 carbon atoms. One of $Ar^1$ and $Ar^2$ may be a hydrogen atom.

Examples of the hydrocarbon group having 1 to 40 carbon atoms include an alkyl group, an alkenyl group, a cycloalkyl group, an aryl group, and an aralkyl group.

The alkoxycarbonyl group is represented by $-COOY'$, wherein $Y'$ is an alkyl group having 1 to 20 carbon atoms.

M is aluminum (Al), gallium (Ga), or indium (In), with In being preferred.

L is a group represented by formula (A') or (A"):

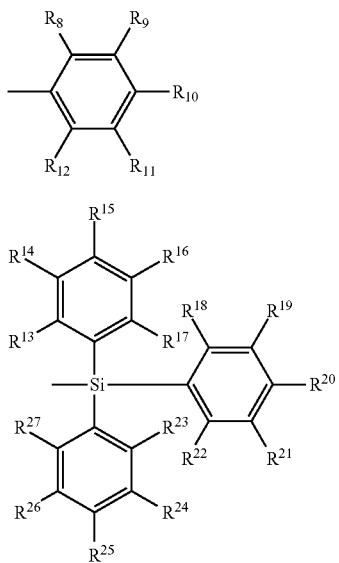

(A')

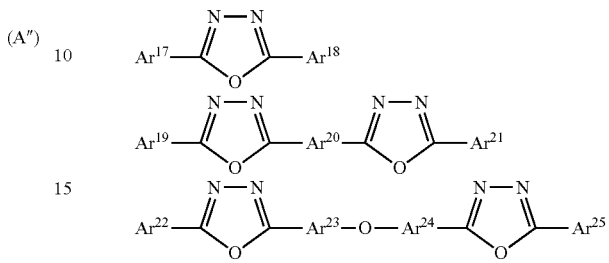

(A")

wherein each $R^8$ to $R^{12}$ independently represents a hydrogen atom or a substituted or unsubstituted hydrocarbon group having 1 to 40 carbon atoms. The adjacent two groups may form a ring structure. Each of $R^{13}$ to $R^{27}$ independently represents a hydrogen atom or a substituted or unsubstituted hydrocarbon group having 1 to 40 carbon atoms. The adjacent two groups may form a ring structure.

Examples of the hydrocarbon group having 1 to 40 carbon atoms for $R^8$ to $R^{12}$ and $R^{13}$ to $R^{27}$ in formulae (A') and (A") are the same as those described above with respect to $R^2$ to $R^7$ of formula (A). Examples of the divalent group formed by the adjacent two groups of $R^8$ to $R^{12}$ and $R^{13}$ to $R^{27}$ which completes the ring structure include tetramethylene group, pentamethylene group, hexamethylene group, diphenylmethane-2,2'-diyl group, diphenylethane-3,3'-diyl group, and diphenylpropane-4,4'-diyl group.

The electron transporting compound for the electron transporting layer is preferably a metal complex including 8-hydroxyquinoline or its derivative, an oxadiazole derivative, and a nitrogen-containing heterocyclic derivative. Examples of the metal complex including 8-hydroxyquinoline or its derivative include a metal chelate oxinoid including a chelated oxine (generally, 8-quinolinol or 8-hydroxyquinoline), for example, tris(8-quinolinol)aluminum. Examples of the oxadiazole derivative are shown below:

wherein each of $Ar^{17}$, $Ar^{18}$, $Ar^{19}$, $Ar^{21}$, $Ar^{22}$, and $Ar^{25}$ is a substituted or unsubstituted aromatic hydrocarbon group or a substituted or unsubstituted fused aromatic hydrocarbon group each having 6 to 50 carbon atoms, and $Ar^{17}$ and $Ar^{18}$, $Ar^{19}$ and $Ar^{21}$, and $Ar^{22}$ and $Ar^{25}$ may be the same or different. Examples of the aromatic hydrocarbon group and the fused aromatic hydrocarbon group include phenyl group, naphthyl group, a biphenyl group, anthranyl group, perylenyl group, and pyrenyl group. The optional substituent may be an alkyl group having 1 to 10 carbon atoms, an alkoxyl group having 1 to 10 carbon atoms or a cyano group.

Each of $Ar^{20}$, $Ar^{23}$, and $Ar^{24}$ is a substituted or unsubstituted bivalent aromatic hydrocarbon group or a substituted or unsubstituted bivalent fused aromatic hydrocarbon group each having 6 to 50 carbon atoms, and $Ar^{23}$ and $Ar^{24}$ may be the same or different. Examples of the bivalent aromatic hydrocarbon group or the bivalent fused aromatic hydrocarbon group include phenylene group, naphthylene group, biphenylene group, anthranylene group, perylenylene group, and pyrenylene group. The optional substituent may be an alkyl group having 1 to 10 carbon atoms, an alkoxyl group having 1 to 10 carbon atoms or a cyano group.

Electron transporting compounds which have a good thin film-forming property are preferably used. Examples of the electron transporting compound are shown below.

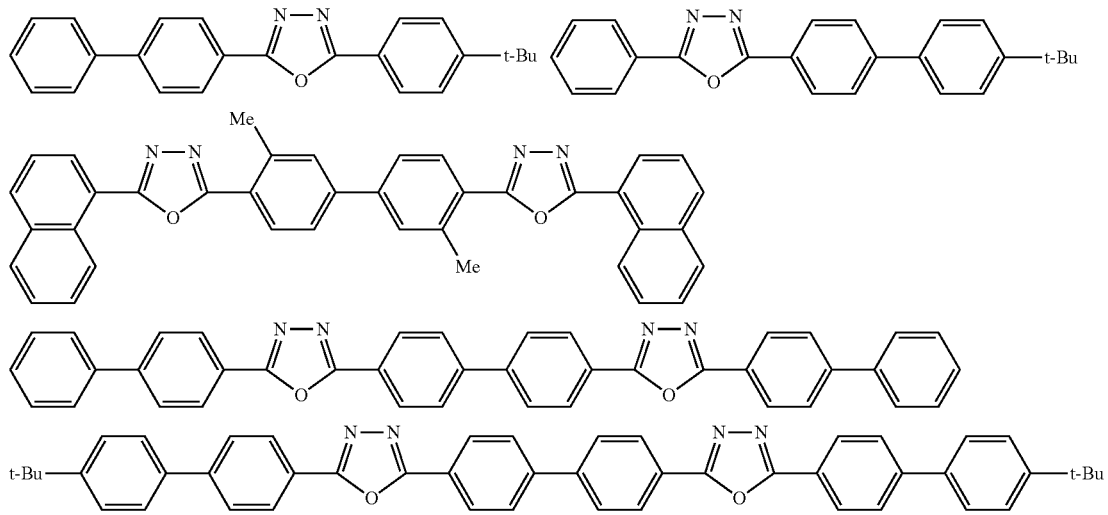

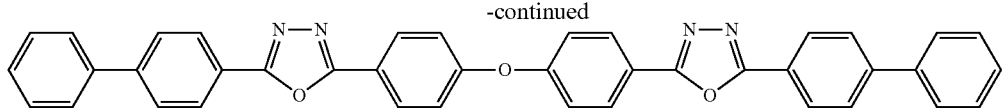

Examples of the nitrogen-containing heterocyclic derivative for use as the electron transporting compound include a nitrogen-containing heterocyclic derivative having the following formulae but exclusive of metal complex, for example, a compound having a 5- or 6-membered ring which has the skeleton represented by formula (B) or having the structure represented by formula (C):

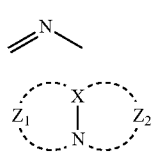

(B)

(C)

wherein X is a carbon atom or a nitrogen atom and each of $Z_1$ and $Z_2$ independently represents a group of atoms for completing the nitrogen-containing heteroring.

The nitrogen-containing heterocyclic derivative is more preferably an organic compound which has a nitrogen-containing aromatic polycyclic ring comprising a 5-membered ring or a 6-membered ring. If two or more nitrogen atoms are included, the nitrogen-containing aromatic polycyclic compound preferably has a skeleton of a combination of (B) and (C) or a combination of (B) and (D):

(D)

The nitrogen-containing group of the nitrogen-containing aromatic polycyclic compound is selected, for example, from the nitrogen-containing heterocyclic groups shown below:

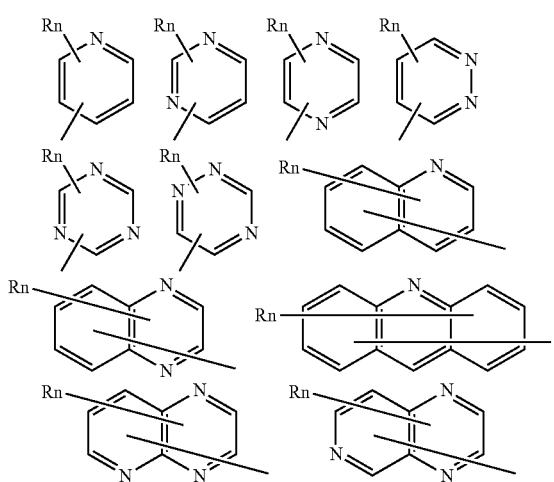

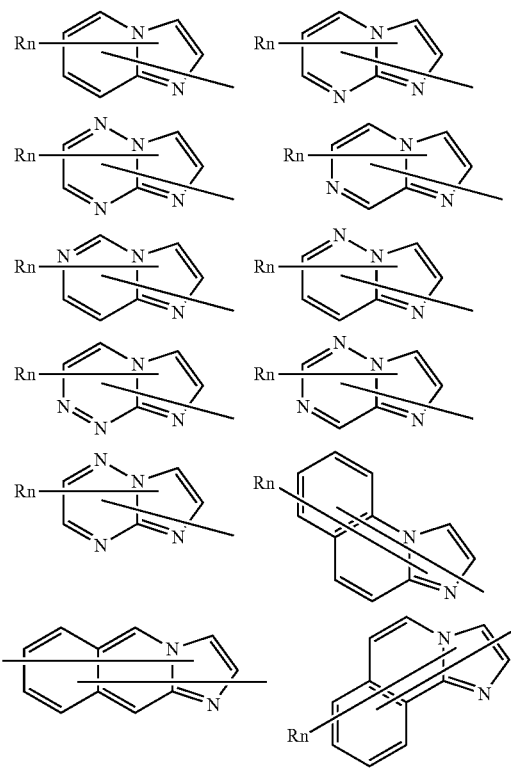

wherein R is an aromatic hydrocarbon group or a fused aromatic hydrocarbon group each having 6 to 40 carbon atoms, an aromatic heterocyclic group or a fused aromatic heterocyclic group each having 3 to 40 carbon atoms, an alkyl group having 1 to 20 carbon atoms, or an alkoxy group having 1 to 20 carbon atoms; and n is an integer of 0 to 5. If n is an integer of 2 or more, R groups may be the same or different.

More preferred is a nitrogen-containing heterocyclic derivative represented by formula (D1):

$$HAr-L^1-Ar^1-Ar^2 \qquad (D1)$$

wherein HAr is a substitute or unsubstituted nitrogen-containing heterocyclic group having 3 to 40 carbon atoms; $L^1$ is a single bond, a substituted or unsubstituted aromatic hydrocarbon group or fused aromatic hydrocarbon group each having 6 to 40 carbon atoms, or a substituted or unsubstituted aromatic heterocyclic group or fused aromatic heterocyclic group each having 3 to 40 carbon atoms; $Ar^1$ is a substitute or unsubstituted divalent aromatic hydrocarbon group having 6 to 40 carbon atoms; and Are is a substitute or unsubstituted aromatic hydrocarbon group or fused aromatic hydrocarbon group each having 6 to 40 carbon atoms or a substituted or unsubstituted aromatic heterocyclic group or fused aromatic heterocyclic group each having 3 to 40 carbon atoms.

HAr is selected, for example, from the following groups:
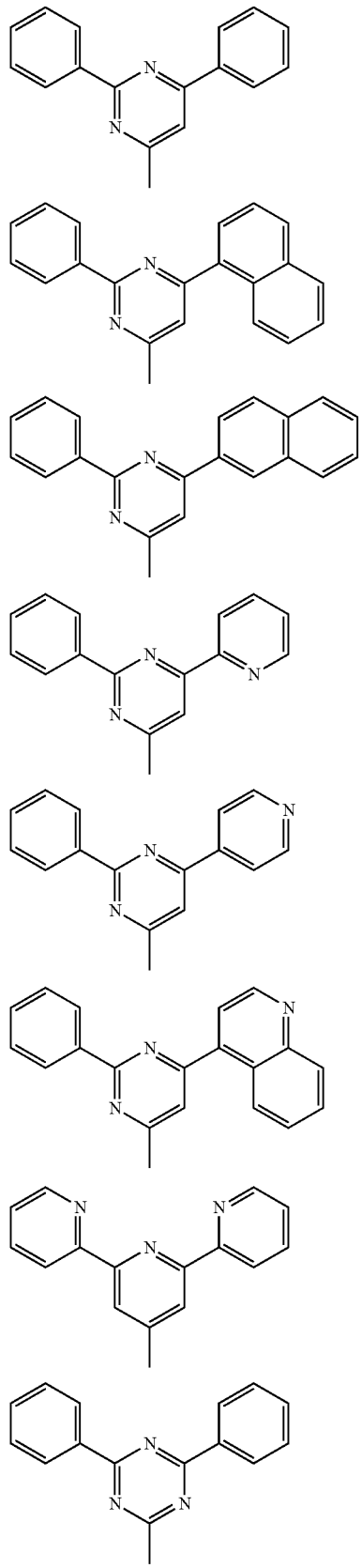
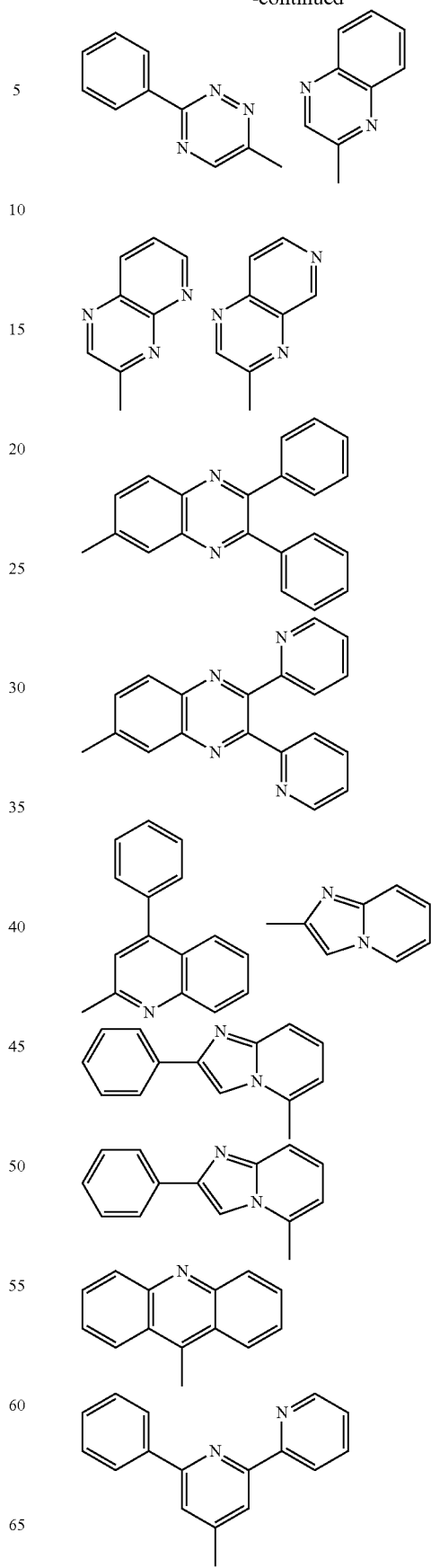

L¹ in formula (D1) is selected, for example, from the following groups:

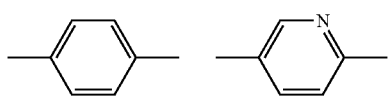

Ar¹ in formula (D1) is selected, for example, from the following arylanthranyl group represented by formula (D2) or (D3):

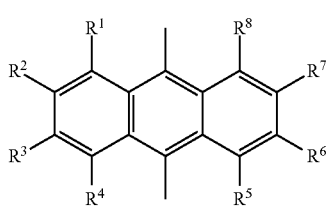
(D2)

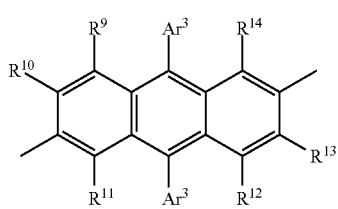
(D3)

wherein $R^1$ to $R^{14}$ are each independently a hydrogen atom, a halogen atom, an alkyl group having 1 to 20 carbon atoms, an alkoxy group having 1 to 20 carbon atoms, an aryloxy group having 6 to 40 carbon atoms, a substituted or unsubstituted aromatic hydrocarbon group or fused aromatic hydrocarbon group each having 6 to 40 carbon atoms, or a substituted or unsubstituted aromatic heterocyclic group or fused aromatic heterocyclic group each having 3 to 40 carbon atoms; and $Ar^3$ is a substituted or unsubstituted aromatic hydrocarbon group or fused aromatic hydrocarbon group each having 6 to 40 carbon atoms or a substituted or unsubstituted aromatic heterocyclic group or fused aromatic heterocyclic group each having 3 to 40 carbon atoms.

$Ar^2$ of formula (D1) is selected, for example, from the following groups:

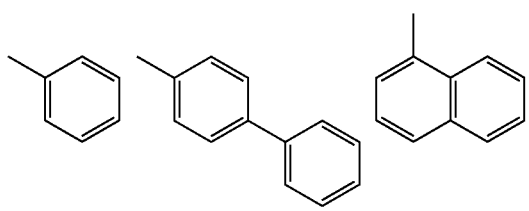

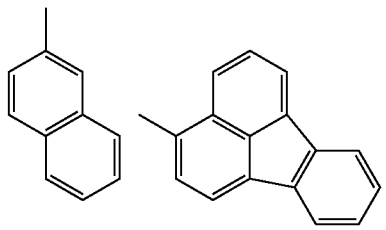

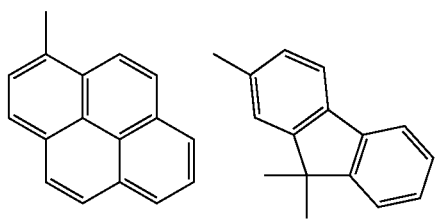

In addition, the following compound is preferably used as the nitrogen-containing aromatic polycyclic compound for use as the electron transporting compound:

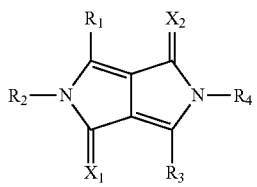
(D4)

wherein $R_1$ to $R_4$ each independently represent a hydrogen atom, a substituted or unsubstituted aliphatic group having 1 to 20 carbon atoms, a substituted or unsubstituted alicyclic group having 3 to 20 carbon atoms, a substituted or unsubstituted aromatic ring group having 6 to 50 carbon atoms, or a substituted or unsubstituted heterocyclic group having 3 to 50 carbon atoms; and $X_1$ and X2 each independently represent an oxygen atom, a sulfur atom, or dicyanomethylene group.

Further, the following compound is also suitable as the electron transporting compound:

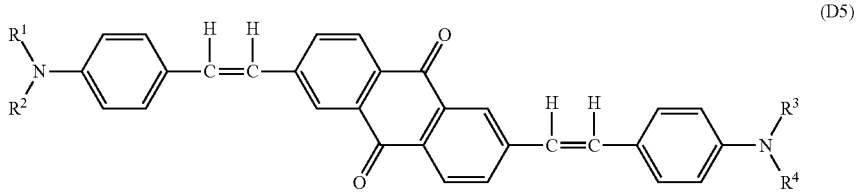

wherein $R^1$, $R^2$, $R^3$, and $R^4$ may be the same or different and each represents an aromatic hydrocarbon group or a fused aromatic hydrocarbon group each represented by formula (D6):

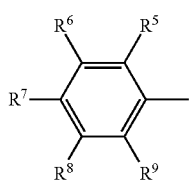

wherein $R^5$, $R^6$, $R^7$, $R^8$, and $R^9$ may be the same or different and each represents a hydrogen atom, a saturated or unsaturated alkoxyl group having 1 to 20 carbon atoms, a saturated or unsaturated alkyl group having 1 to 20 carbon atoms, an amino group, or an alkylamino group having 1 to 20 carbon atoms. At least one of $R^5$, $R^6$, $R^7$, $R^8$, and $R^9$ represents a group other than a hydrogen atom.

Further, a polymer having the nitrogen-containing heterocyclic group or the nitrogen-containing heterocyclic derivative is also usable as the electron transporting compound.

The electron transporting layer in the organic EL device of the invention preferably comprises at least one compound selected from the nitrogen-containing heterocyclic derivatives represented by formulae (E) to (G):

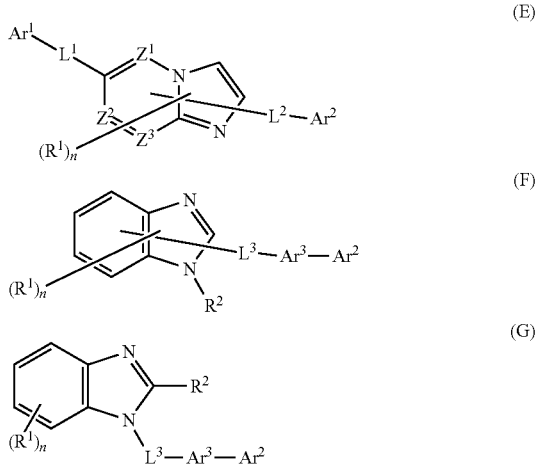

wherein $Z^1$, $Z^2$, and $Z^3$ each independently represent a nitrogen atom or a carbon atom;

$R^1$ and $R^2$ each independently represent a substituted or unsubstituted aryl group having 6 to 50 ring carbon atoms, a substituted or unsubstituted heteroaryl group having 5 to 50 ring atoms, a substituted or unsubstituted alkyl group having 1 to 20 carbon atoms, a substituted or unsubstituted haloalkyl group having 1 to 20 carbon atoms, or a substituted or unsubstituted alkoxyl group having 1 to 20 carbon atoms;

n is an integer of 0 to 5, when n is an integer of 2 or more, $R^1$ groups may be the same or different, and the adjacent two $R^1$ groups may bond to each other to form a substituted or unsubstituted hydrocarbon ring;

$Ar^1$ represents a substituted or unsubstituted aryl group having 6 to 50 ring carbon atoms or a substituted or unsubstituted heteroaryl group having 5 to 50 ring atoms;

$Ar^2$ represents a hydrogen atom, a substituted or unsubstituted alkyl group having 1 to 20 carbon atoms, a substituted or unsubstituted haloalkyl group having 1 to 20 carbon atoms, a substituted or unsubstituted alkoxyl group having 1 to 20 carbon atoms, a substituted or unsubstituted aryl group having 6 to 50 ring carbon atoms, or a substituted or unsubstituted heteroaryl group having 5 to 50 ring atoms;

provided that one of $Ar^1$ and $Ar^2$ is a substituted or unsubstituted condensed aromatic hydrocarbon ring group having 10 to 50 ring carbon atoms or a substituted or unsubstituted condensed aromatic heterocyclic group having 9 to 50 ring atoms;

$Ar^3$ represents a substituted or unsubstituted arylene group having 6 to 50 ring carbon atoms or a substituted or unsubstituted heteroarylene group having 5 to 50 ring atoms; and $L^1$, $L^2$, and $L^3$ each independently represent a single bond, a substituted or unsubstituted arylene group having 6 to 50 ring carbon atoms or a substituted or unsubstituted divalent condensed aromatic heterocyclic group having 9 to 50 ring atoms.

Examples of the aryl group having 6 to 50 ring carbon atoms include phenyl group, naphthyl group, anthryl group, phenanthryl group, naphthacenyl group, chrysenyl group, pyrenyl group, a biphenyl group, terphenyl group, tolyl group, fluoranthenyl group, and fluorenyl group.

Examples of the heteroaryl group having 5 to 50 ring atoms include pyrrolyl group, furyl group, thiophenyl group, silolyl group, pyridyl group, quinolyl group, isoquinolyl group, benzofuryl group, imidazolyl group, pyrimidyl group, carbazolyl group, selenophenyl group, oxadiazolyl group, triazolyl group, pyrazinyl group, pyridazinyl group, triazinyl group, quinoxalinyl group, acridinyl group, imidazo[1,2-a]pyridinyl group, and imidazo[1,2-a]pyrimidinyl.

Examples of the alkyl group having 1 to 20 carbon atoms include methyl group, ethyl group, propyl group, butyl group, pentyl group, and hexyl group.

Examples of the haloalkyl group having 1 to 20 carbon atoms include the groups obtained by replacing one or more hydrogen atoms of the alkyl group mentioned above with at least one halogen atom selected from fluorine, chlorine, iodine, and bromine.

Examples of the alkyl moiety of the alkoxyl group having 1 to 20 carbon atoms include the alkyl group mentioned above.

Examples of the arylene groups include the groups obtained by removing one hydrogen atom from the aryl group mentioned above.

Examples of the divalent condensed aromatic heterocyclic group having 9 to 50 ring atoms include the groups obtained by removing one hydrogen atom from the condensed aromatic heterocyclic group mentioned above as the heteroaryl group.

The thickness of the electron transporting layer is preferably, but not particularly limited to, 1 to 100 nm.

Preferred examples of the material for a electron injecting layer optionally formed adjacent to the electron transporting layer include, in addition to the nitrogen-containing ring derivative, an inorganic compound, such as an insulating material and a semiconductor. The electron injecting layer containing the insulating material or the semiconductor effectively prevents the leak of electric current to enhance the electron injecting properties.

The insulating material is preferably at least one metal compound selected from the group consisting of alkali metal chalcogenides, alkaline earth metal chalcogenides, alkali metal halides and alkaline earth metal halides. The alkali metal chalcogenide, etc. mentioned above are preferred because the electron injecting properties of the electron injecting layer are further enhanced. Examples of preferred alkali metal chalcogenide include $Li_2O$, $K_2O$, $Na_2S$, $Na_2Se$ and $Na_2O$, and examples of preferred alkaline earth metal chalcogenide include CaO, BaO, SrO, BeO, BaS and CaSe. Examples of preferred alkali metal halide include LiF, NaF, KF, LiCl, KCl and NaCl. Examples of the alkaline earth metal halide include fluorides, such as $CaF_2$, $BaF_2$, $SrF_2$, $MgF_2$ and $BeF_2$, and halides other than fluorides.

Examples of the semiconductor include oxides, nitrides or oxynitrides of at least one element selected from the group consisting of Ba, Ca, Sr, Yb, Al, Ga, In, Li, Na, Cd, Mg, Si, Ta, Sb and Zn. The semiconductor may be used alone or in combination of two or more. The inorganic compound included in the electron injecting layer preferably forms a microcrystalline or amorphous insulating thin film. If the electron injecting layer is formed from such an insulating thin film, the pixel defects, such as dark spots, can be decreased because a more uniform thin film is formed. Examples of such inorganic compound include the alkali metal chalcogenide, the alkaline earth metal chalcogenide, the alkali metal halide and the alkaline earth metal halide.

When using the insulating material or the semiconductor, the thickness of its layer is preferably about 0.1 to 15 nm. The electron injecting layer in the invention may contain the electron-donating dopant mentioned above.

Hole Transporting Layer

The hole injecting/transporting layer is an organic layer formed between the light emitting layer and the anode and has a function of transporting holes from the anode to the light emitting layer. When the hole transporting layer is formed by two or more layers, the layer closer to the anode may be defined as the hole injecting layer in some cases. The hole injecting layer has a function of efficiently injecting holes from the anode to the organic layer unit.

Another preferred material for the hole transporting layer may include an aromatic amine compound, for example, an aromatic amine derivative represented by formula (H):

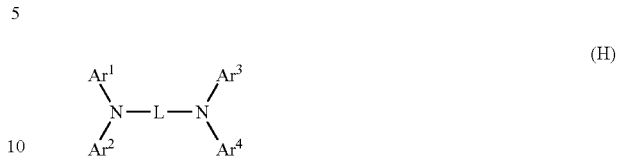

wherein each of $Ar^1$ to $Ar^4$ represents a substituted or unsubstituted aromatic hydrocarbon group or fused aromatic hydrocarbon group having 6 to 50 ring carbon atoms, a substituted or unsubstituted aromatic heteroaryl group or fused aromatic heteroaryl group having 5 to 50 ring atoms, or a group wherein the aromatic hydrocarbon group or fused aromatic hydrocarbon group is bonded to the aromatic heteroaryl group or fused aromatic heteroaryl group.

L represents a substituted or unsubstituted aromatic hydrocarbon group or fused aromatic hydrocarbon group having 6 to 50 ring carbon atoms or a substituted or unsubstituted aromatic heteroaryl group or fused aromatic heteroaryl group having 5 to 50 ring atoms.

Examples of the compound represented by formula (I) are shown below.

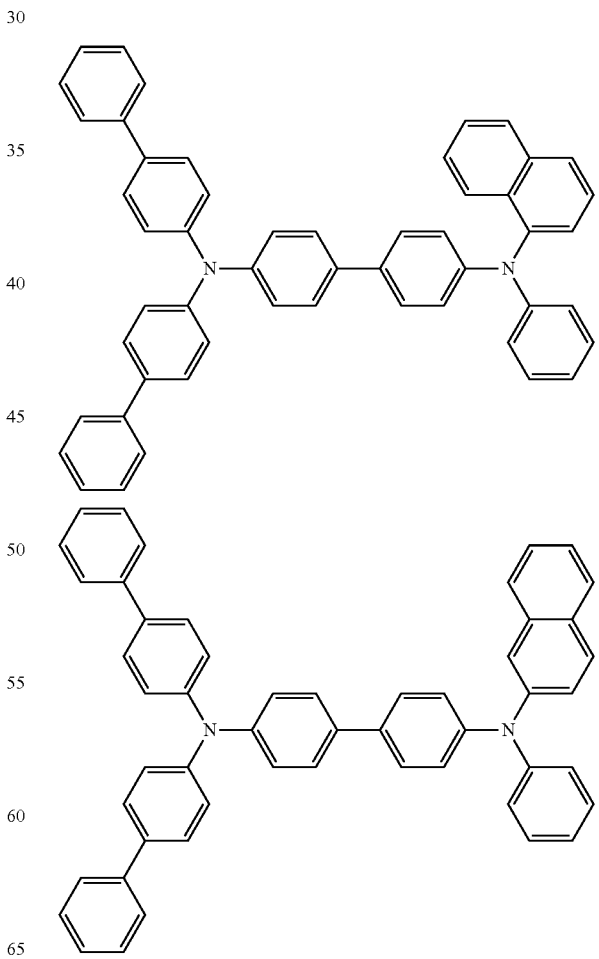

135
-continued
136
-continued
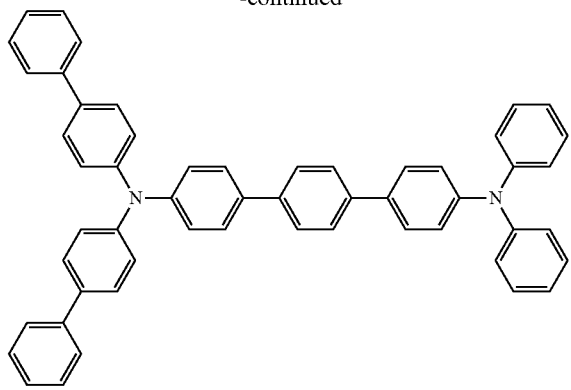
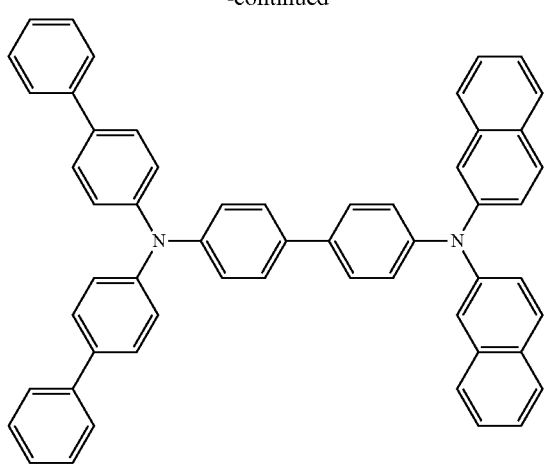
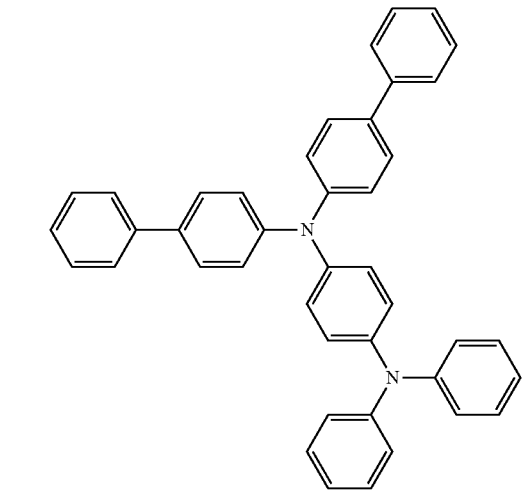
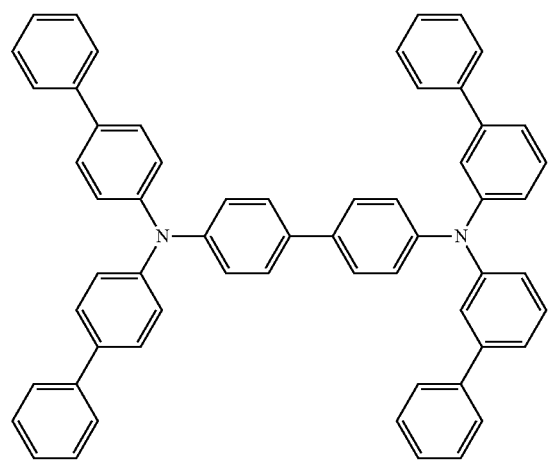
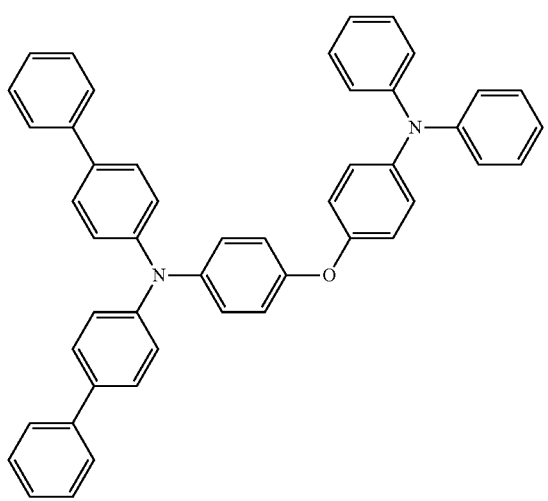

137
-continued
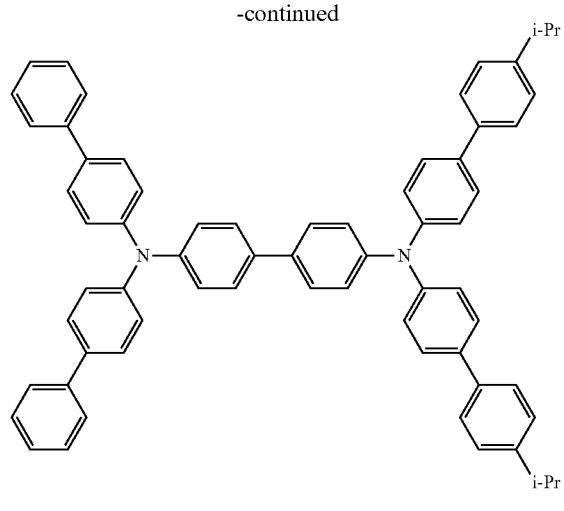
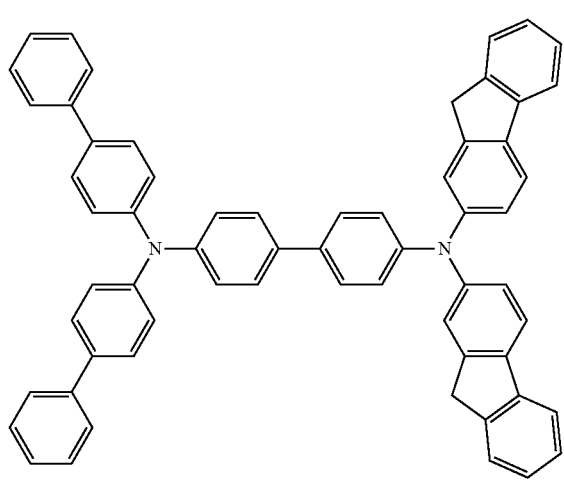
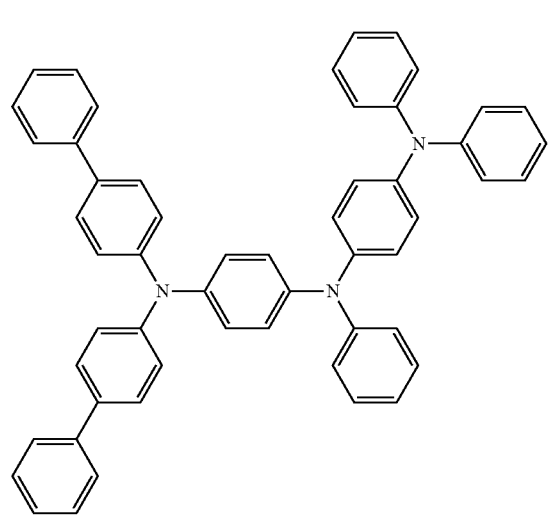
138
-continued
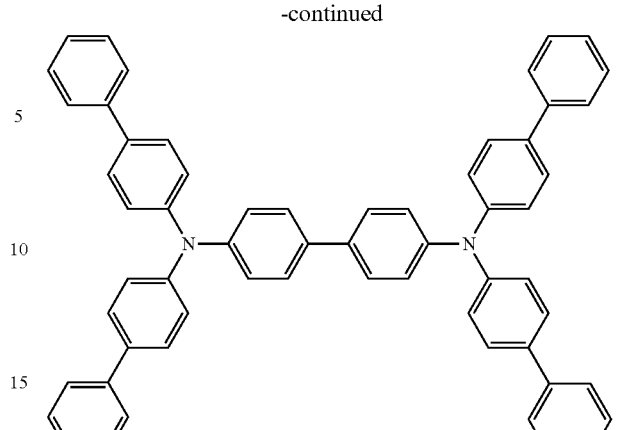
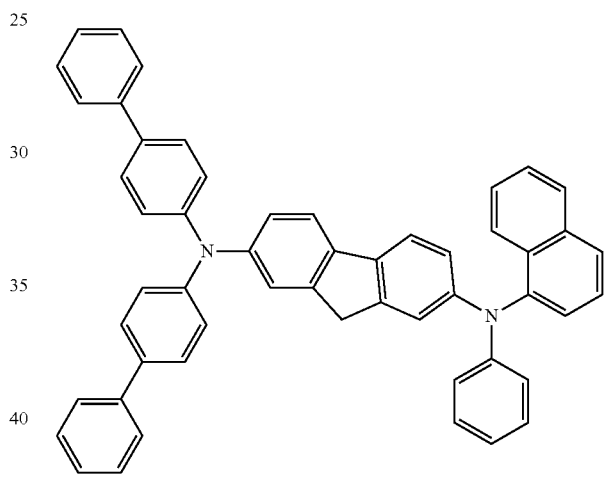
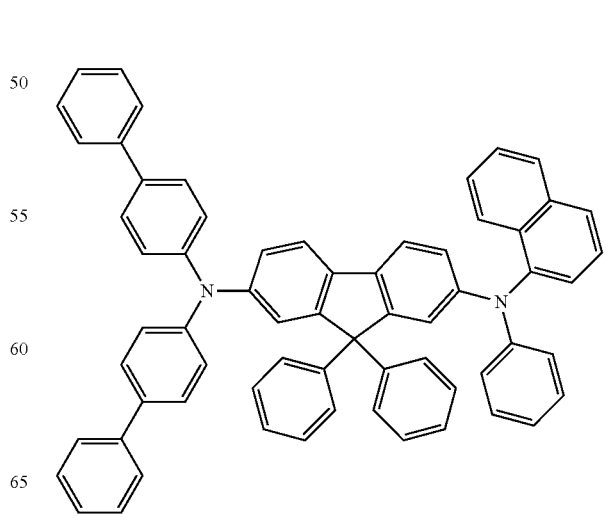

139
-continued
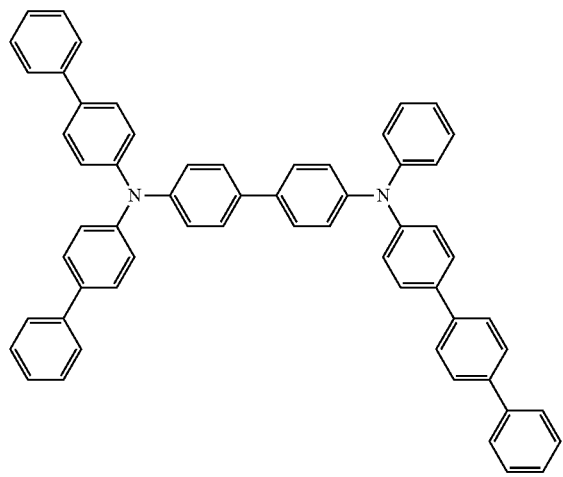
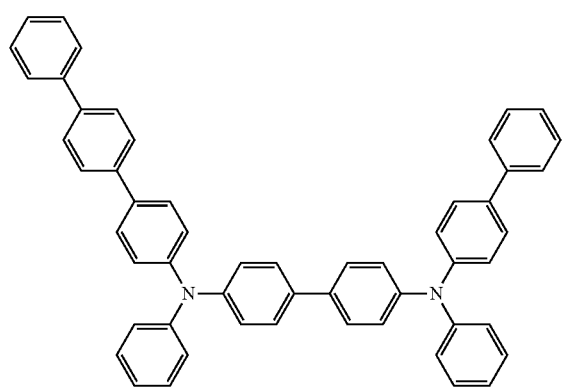
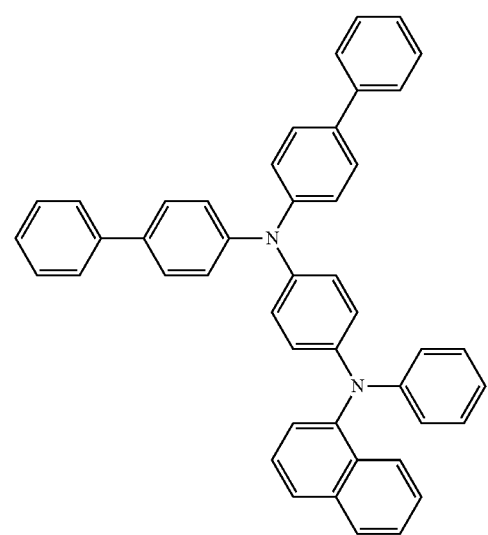
140
-continued
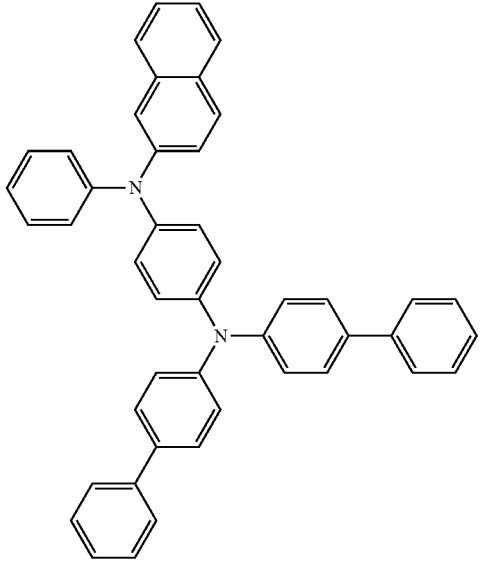
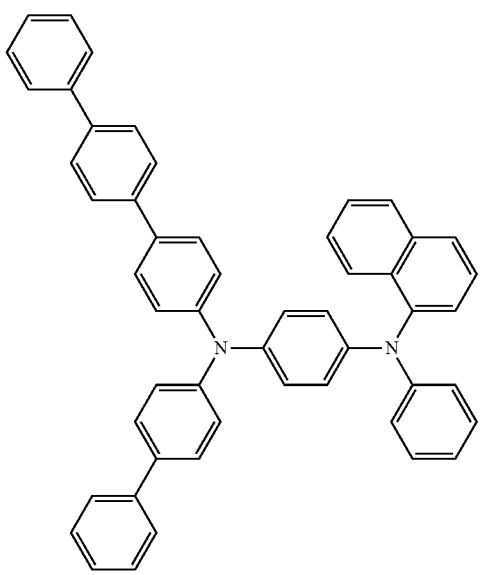
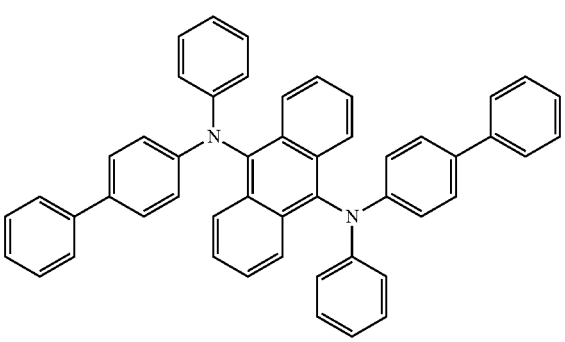

141
-continued
142
-continued
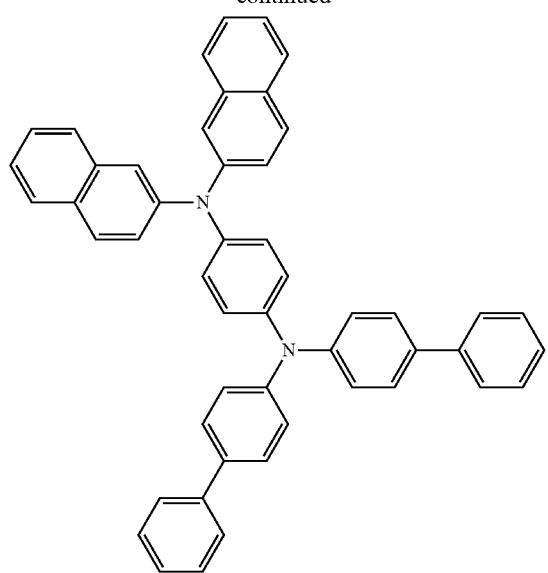
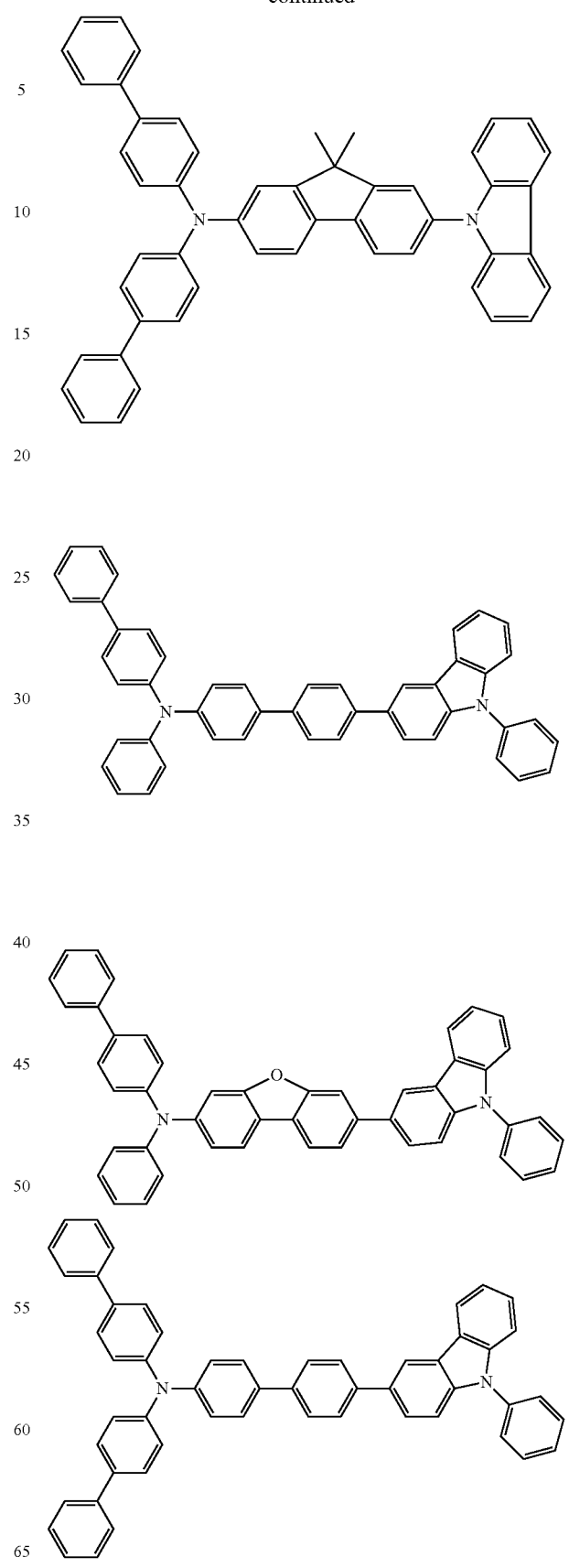

-continued
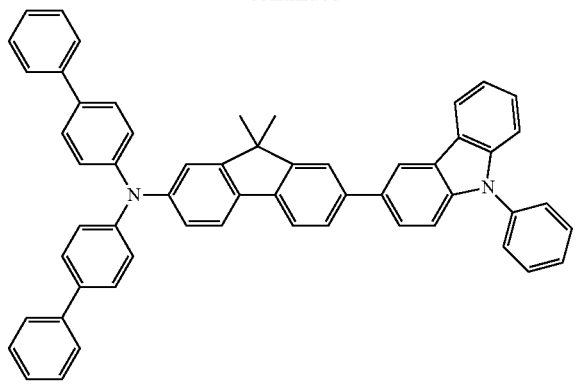
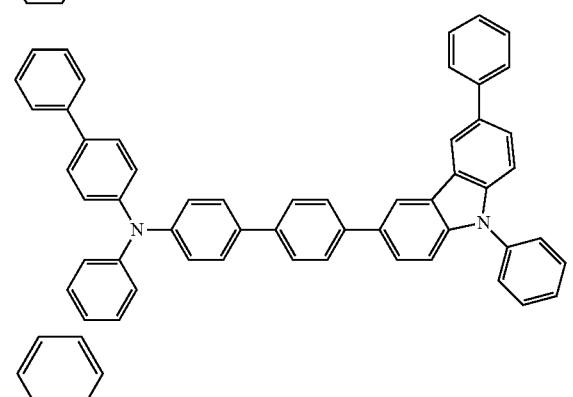
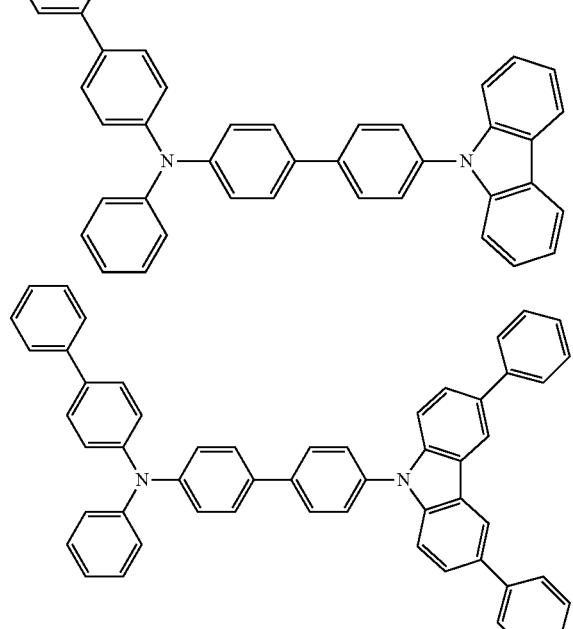
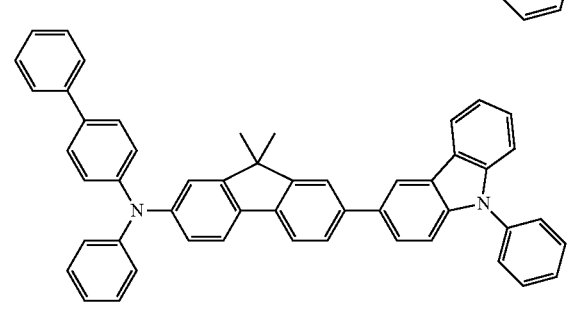
An aromatic amine represented by formula (J) is also preferably used to form the hole transporting layer:
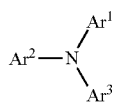
(J)
wherein $Ar^1$ to $Ar^3$ are the same as defined with respect to $Ar^1$ to $Ar^4$ of formula (H). Examples of the compound represented by formula (J) are shown below, although not limited thereto.
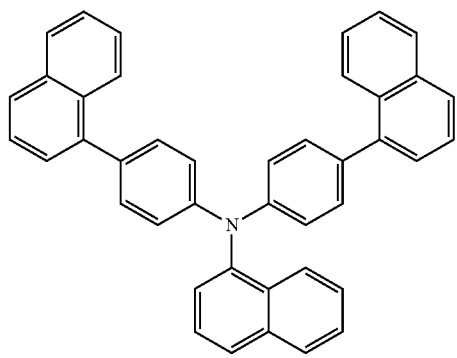
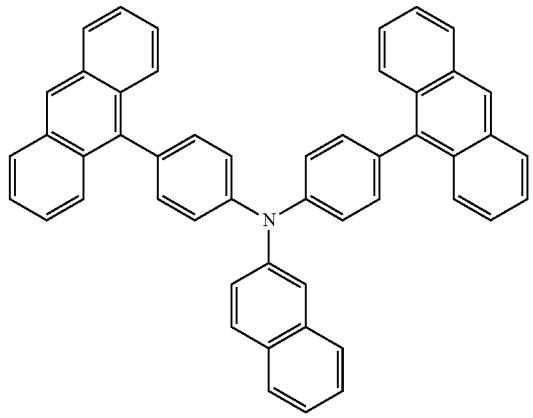
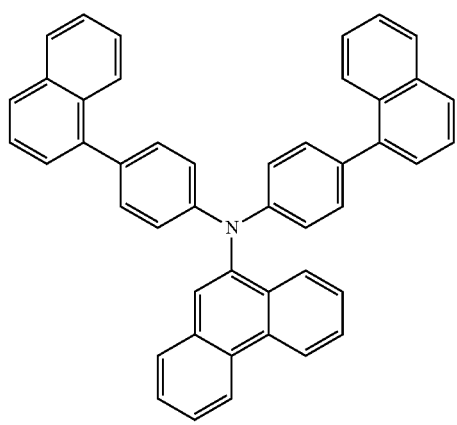

145
-continued
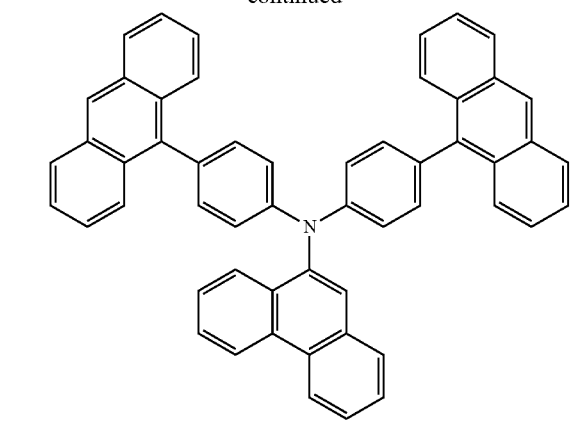
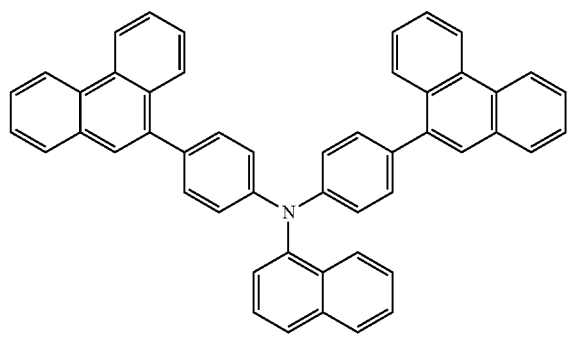
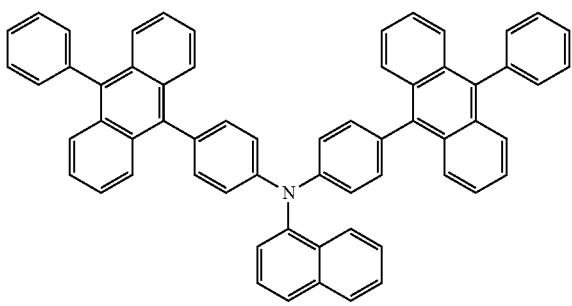
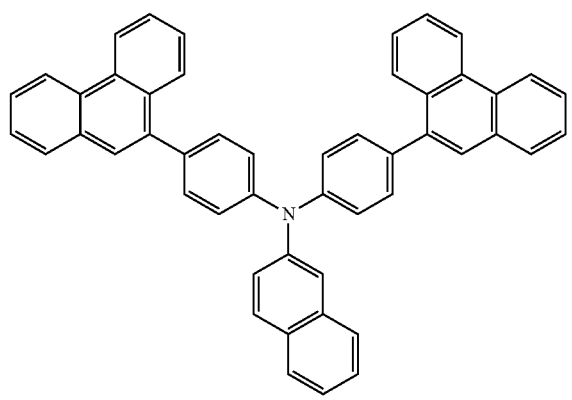
146
-continued
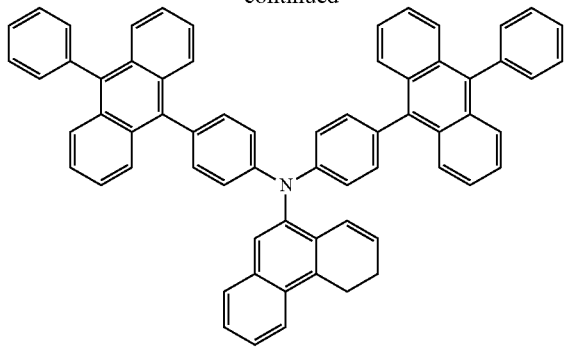
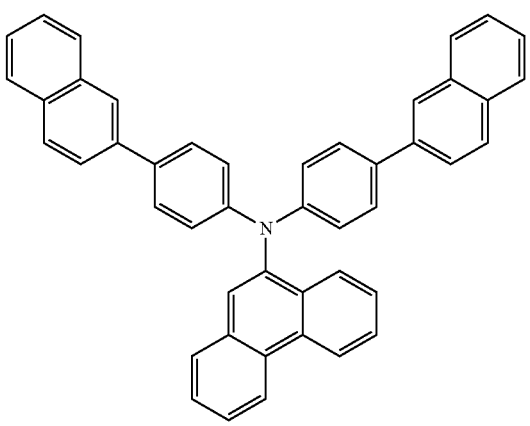
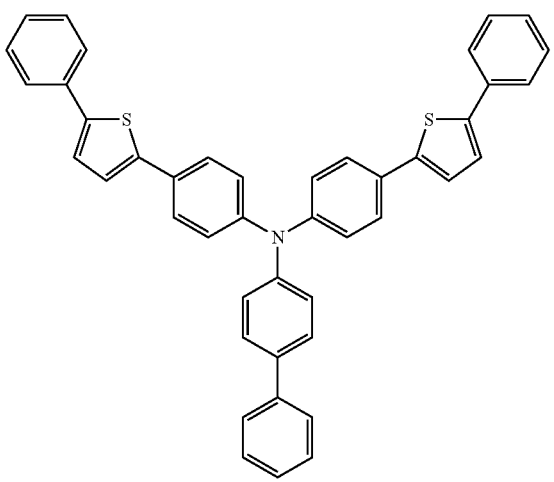
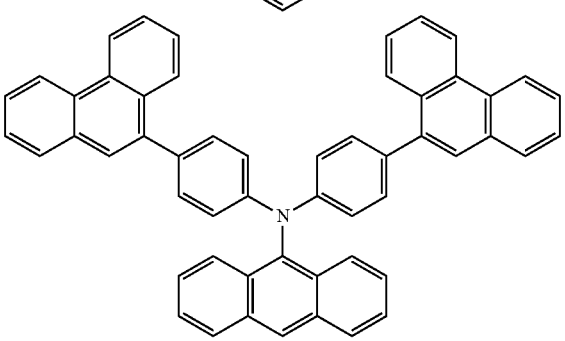

147
-continued

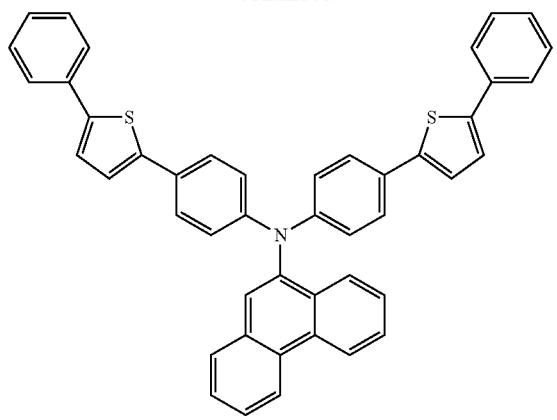

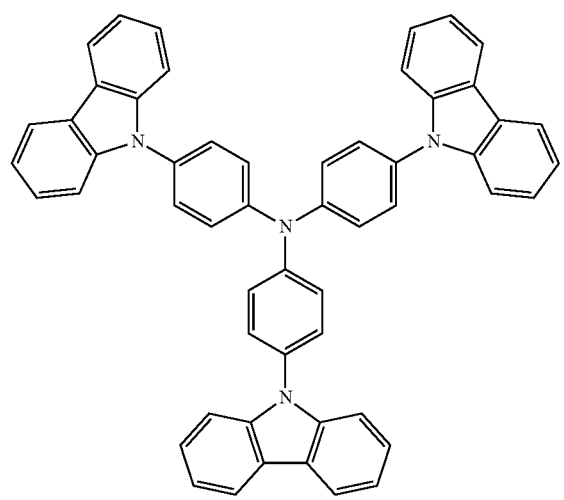

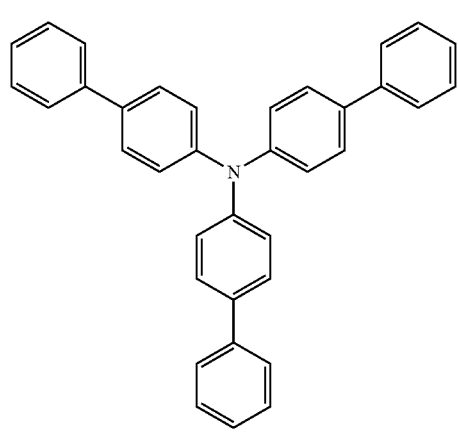

148
-continued

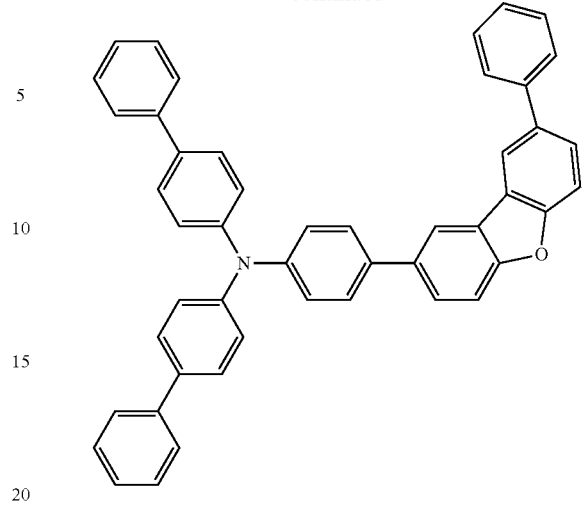

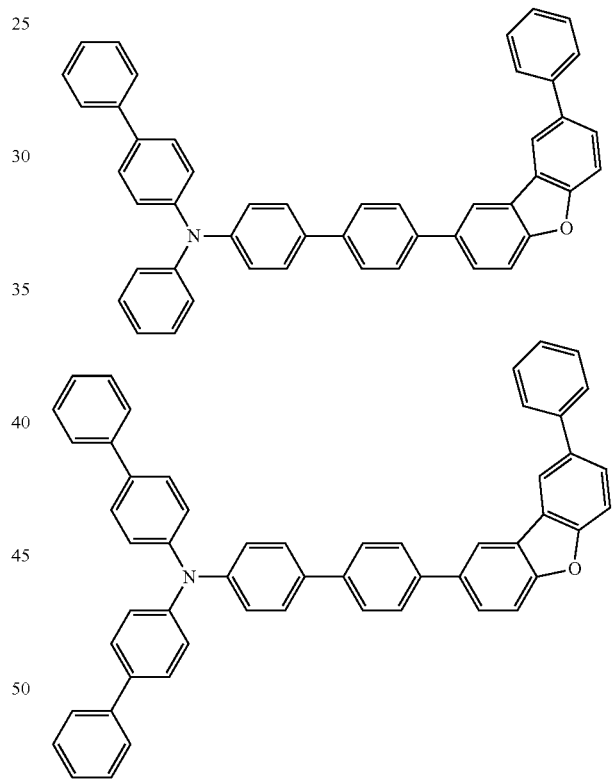

The hole transporting layer may be made into two-layered structure of a first hole transporting layer (anode side) and a second hole transporting layer (cathode side).

The thickness of the hole transporting layer is preferably 10 to 200 nm, although not particularly limited thereto.

The organic EL device of the invention may have a layer comprising an acceptor material which is attached to the anode side of each of the hole transporting layer and the first hole transporting layer. With such a layer, it is expected that the driving voltage is lowered and the production cost is reduced.

The acceptor material is preferably a compound represented by formula (K):

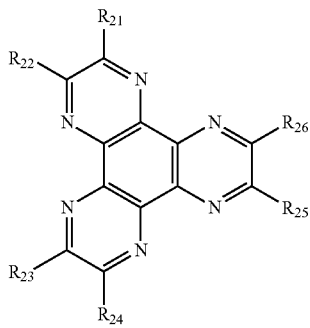

(K)

wherein $R_{21}$ to $R_{26}$ may be the same or different and each independently represent a cyano group, —$CONH_2$, a carboxyl group, or —$COOR_{27}$ wherein $R_{27}$ represents an alkyl group having 1 to 20 carbon atoms or a cycloalkyl group having 3 to 20 carbon atoms. One or more of a pair of $R_{21}$ and $R_{22}$, a pair of $R_{23}$ and $R_{24}$, and a pair of $R_{25}$ and $R_{26}$ may bond to each other to form a group represented by —CO—O—CO—.

Examples of $R_{27}$ include methyl group, ethyl group, n-propyl group, isopropyl group, n-butyl group, isobutyl group, t-butyl group, cyclopentyl group, and cyclohexyl group.

The thickness of the layer comprising the acceptor material is preferably 5 to 20 nm, although not particularly limited thereto.

N/P Doping

The carrier injecting properties of the hole transporting layer and the electron transporting layer can be controlled by, as described in JP 3695714B, the doping (n) with a donor material or the doping (p) with an acceptor material.

A typical example of the n-doping is an electron transporting material doped with a metal, such as Li and Cs, and a typical example of the p-doping is a hole transporting material doped with an acceptor material, such as $F_4TCNQ$ (2,3,5,6-Tetrafluoro-7,7,8,8-tetracyanoquinodimethane).

Space Layer

For example, in an organic EL device wherein a fluorescent light emitting layer and a phosphorescent light emitting layer are laminated, a space layer is disposed between the fluorescent light emitting layer and the phosphorescent light emitting layer to prevent the diffusion of excitons generated in the phosphorescent light emitting layer to the fluorescent light emitting layer or to control the carrier balance. The space layer may be disposed between two or more phosphorescent light emitting layers.

Since the space layer is disposed between the light emitting layers, a material combining the electron transporting ability and the hole transporting ability is preferably used for forming the space layer. To prevent the diffusion of triplet energy in the adjacent phosphorescent light emitting layer, the triplet energy of the material for the space layer is preferably 2.6 eV or more. The materials described with respect to the hole transporting layer are usable as the material for the space layer.

Blocking Layer

The organic EL device of the invention preferably has a blocking layer, such as an electron blocking layer, a hole blocking layer, and a triplet blocking layer, which is disposed adjacent to the light emitting layer. The electron blocking layer is a layer which prevents the diffusion of electrons from the light emitting layer to the hole transporting layer. The hole blocking layer is a layer which prevents the diffusion of holes from the light emitting layer to the electron transporting layer.

The triplet blocking layer prevents the diffusion of triplet excitons generated in the light emitting layer to adjacent layers and has a function of confining the triplet excitons in the light emitting layer, thereby preventing the deactivation of energy on molecules other than the emitting dopant of triplet excitons, for example, on molecules in the electron transporting layer.

If a phosphorescent device having a triplet blocking layer satisfies the following energy relationship:

$$E^T_d < E^T_{TB}$$

wherein $E^T_d$ is the triplet energy of the phosphorescent dopant in the light emitting layer and $E^T_{TB}$ is the triplet energy of the compound forming the triplet blocking layer, the triplet excitons of phosphorescent dopant are confined (not diffuse to other molecules). Therefore, the energy deactivation process other than the emission on the phosphorescent dopant may be prevented to cause the emission with high efficiency. However, even in case of satisfying the relationship of $E^T_d < E^T_{TB}$, the triplet excitons may move into other molecules if the energy difference ($\Delta E^T = E^T_{TB} - E^T_d$) is small, because the energy difference $\Delta E^T$ may be overcome by the absorption of ambient heat energy when driving a device at around room temperature as generally employed in practical drive of device. As compared with the fluorescent emission, the phosphorescent emission is relatively likely to be affected by the diffusion of excitons due to the heat absorption because the lifetime of triplet excitons is longer. Therefore, as for the energy difference $\Delta E^T$, the larger as compared with the heat energy of room temperature, the better. The energy difference $\Delta E^T$ is more preferably 0.1 eV or more and particularly preferably 0.2 eV or more. In fluorescent devices, the material for organic EL device of the invention is usable as the material for triplet blocking layer of the TTF device described in WO 2010/134350A1.

The electron mobility of the material for the triplet blocking layer is preferably $10^{-6}$ cm$^2$/Vs or more at an electric field strength in a range of 0.04 to 0.5 MV/cm. There are several methods for measuring the electron mobility of organic material, for example, Time of Flight method. In the present invention, the electron mobility is determined by impedance spectroscopy.

The electron mobility of the electron injecting layer is preferably $10^{-6}$ cm$^2$/Vs or more at an electric field strength in a range of 0.04 to 0.5 MV/cm. Within the above range, the injection of electrons from the cathode to the electron transporting layer is promoted and the injection of electrons to the adjacent blocking layer and light emitting layer is also promoted, thereby enabling to drive a device at lower voltage.

EXAMPLES

The present invention will be described in more detail with reference to the examples. However, it should be noted that the scope of the invention is not limited to the following examples.

Synthesis of Material for Organic El Device

Synthesis Example 1

Synthesis of Intermediate 1

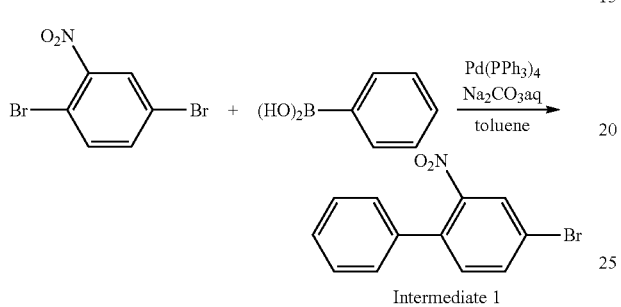

Intermediate 1

In argon stream, a mixture obtained by successively mixing 2-nitro-1,4-dibromobenzene (11.2 g, 40 mmol), phenylboronic acid (4.9 g, 40 mmol), tetrakis(triphenylphosphine)palladium (1.39 g, 1.2 mmol), toluene (120 mL), and a 2M aqueous solution of sodium carbonate (60 mL) was refluxed under heating for 8 h.

After cooling the reaction liquid to room temperature, the organic layer was separated and the organic solvent was removed from the organic layer by distillation under reduced pressure. The obtained residue was purified by a silica gel column chromatography to obtain intermediate 1 (6.6 g, yield: 59%). The identification of intermediate 1 was made by FD-MS (field desorption mass spectrometry) analysis.

Synthesis Example 2

Synthesis of intermediate 2

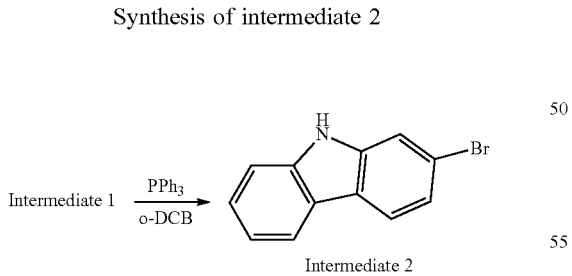

Intermediate 2

In argon stream, a mixture obtained by successively mixing intermediate 1 (6.6 g, 23.7 mmol), triphenylphosphine (15.6 g, 59.3 mmol), and o-dichlorobenzene (24 mL) was heated at 180° C. for 8 h.

After cooling the reaction liquid to room temperature, the reaction product was purified by a silica gel column chromatography to obtain intermediate 2 (4 g, yield: 68%). The identification of intermediate 2 was made by FD-MS analysis.

Synthesis Example 3

Synthesis of Intermediate 3

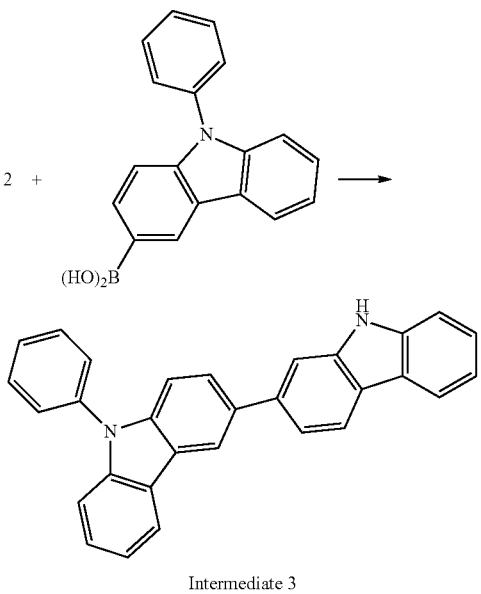

Intermediate 3

The procedure of Synthesis of intermediate 1 was repeated except for using intermediate 2 in place of 2-nitro-1,4-dibromobenzene and using 9-phenyl-9H-carbazole-3-ylboronic acid in place of phenylboronic acid. The obtained compound was identified as intermediate 3 by FD-MS analysis.

Synthesis Example 4

Synthesis of intermediate 4

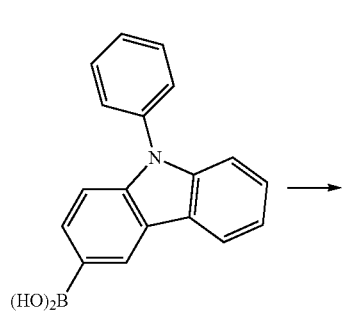

153

-continued

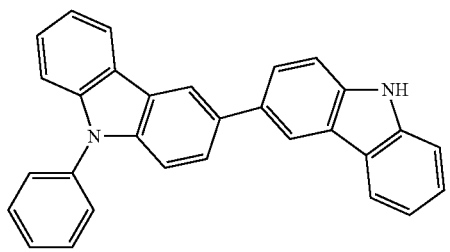

Intermediate 4

The procedure of Synthesis of intermediate 1 was repeated except for using 3-bromocarbazole in place of 2-nitro-1,4-dibromobenzene and using 9-phenyl-9H-carbazole-3-ylboronic acid in place of phenylboronic acid. The obtained compound was identified as intermediate 4 by FD-MS analysis.

Synthesis Example 5

Synthesis of Intermediate 5

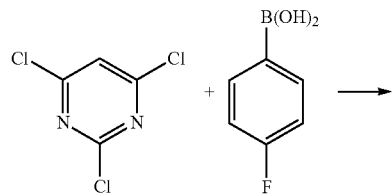

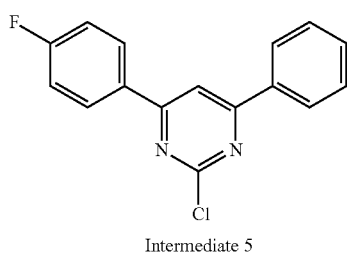

Intermediate 5

The procedure of Synthesis of intermediate 1 was repeated except for using 2,4,6-trichloropyrimidine in place of 2-nitro-1,4-dibromobenzene and using p-fluorophenylboronic acid in place of phenylboronic acid. The obtained compound was identified as intermediate 5 by FD-MS analysis.

154

Synthesis Example 6

Synthesis of Compound H1

$$\text{Intermediate 3 + Intermediate 5} \xrightarrow[\text{xylene}]{\substack{\text{Pd}_2(\text{dba})_3 \\ \text{P}(t\text{Bu})_3 \cdot \text{HBF}_4 \\ \text{NaOtBu}}}$$

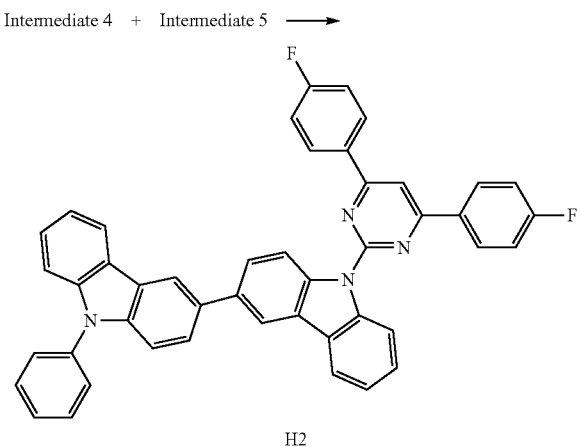

H1

In argon atmosphere, a mixture obtained by successively mixing intermediate 3 (4.1 g, 10 mmol), intermediate 5 (3.6 g, 12 mmol), tris(dibenzylideneacetone)dipalladium (0.183 g, 0.20 mmol), tri-t-butylphosphonium tetrafluoroborate (0.15 g, 0.52 mmol), sodium t-butoxide (1.9 g, 20 mmol), dry xylene (50 mL) was refluxed under heating for 8 h.

After cooling the reaction liquid to room temperature, the organic layer was separated and the organic solvent was removed from the organic layer by distillation under reduced pressure. The obtained residue was purified by a silica gel column chromatography to obtain 5.4 g of yellowish white solid (H1).

The result of FD-MS measurement of the obtained compound is shown below.

FDMS, calcd for $C_{47}H_{29}N_5$=674, found m/z=674 (M+)

Synthesis Example 7

Synthesis of Compound H2

Intermediate 4 + Intermediate 5 ⟶

H2

The procedure of Synthesis Example 1 was repeated except for using intermediate 4 in place of intermediate 3.

The result of FD-MS measurement of the obtained compound is shown below.

FDMS, calcd for $C_{47}H_{29}N_5$=674, found m/z=674 (M+)

Production of Organic EL Device and Evaluation of Emission Performance

Example 1

Production of Organic EL Device

A glass substrate of 25 mm×75 mm×1.1 mm thickness having an ITO transparent electrode (product of Geomatec Company) was cleaned by ultrasonic cleaning in isopropyl alcohol for 5 min and then UV ozone cleaning for 30 min.

The cleaned glass substrate was mounted to a substrate holder of a vacuum vapor deposition apparatus. The electron accepting compound C-1 (acceptor) shown below was vapor-deposited so as to cover the transparent electrode to form a compound C-1 film with a thickness of 5 nm. On the compound C-1 film, a first hole transporting material (aromatic amine derivative (compound X1) shown below) was vapor-deposited to form a first hole transporting layer with a thickness of 65 nm. Successively after forming the first hole transporting layer, a second hole transporting material (aromatic amine derivative (compound X2) shown below) was vapor-deposited to form a second hole transporting layer with a thickness of 10 nm.

On the second hole transporting layer, the compound H1 (host material) and Ir(bzq)$_3$ (phosphorescent emitting material) shown below were co-deposited to form a phosphorescent light emitting layer with a thickness of 25 nm. The concentration of Ir(bzq)$_3$ in the light emitting layer was 10.0% by mass. The co-deposited film works as a light emitting layer.

Successively after forming the light emitting layer, the compound ET shown below was vapor-deposited into a film with a thickness of 35 nm. The compound ET film works as an electron transporting layer.

Then, LiF was vapor-deposited into a film with a thickness of 1 nm at a film-forming speed of 0.1 Å/min to form an electron injecting electrode (cathode). On the LiF film, metallic Al was vapor-deposited to form a metallic cathode with a thickness of 80 nm, thereby obtaining an organic EL device.

The obtained organic EL device was measured for the device performance (80% lifetime) by driving the device at current density of 50 mA/cm$^2$. The 80% lifetime is the time taken until the luminance was reduced to 80% of the initial luminance when driving the device at constant current. The result is shown in Table 1.

The compounds used in the examples and comparative examples are shown below.

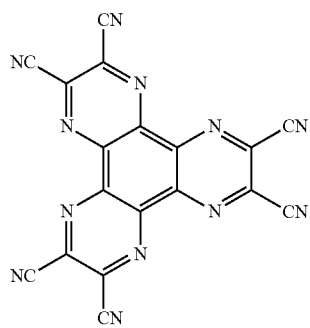

C-1

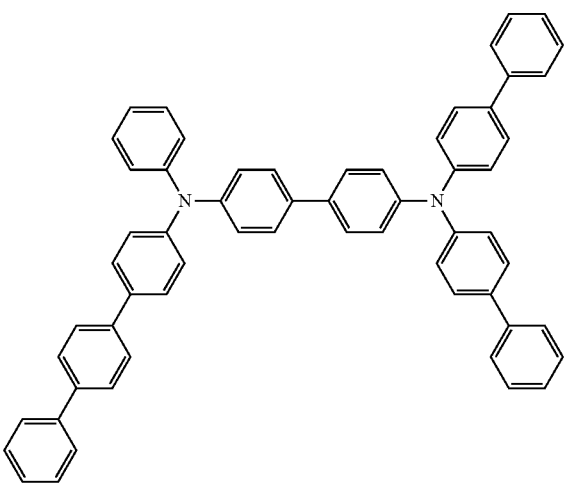

X1

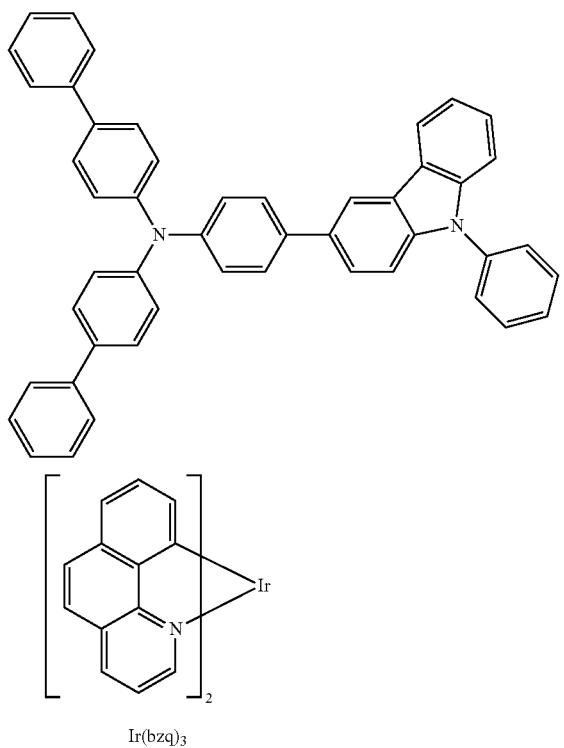

X2

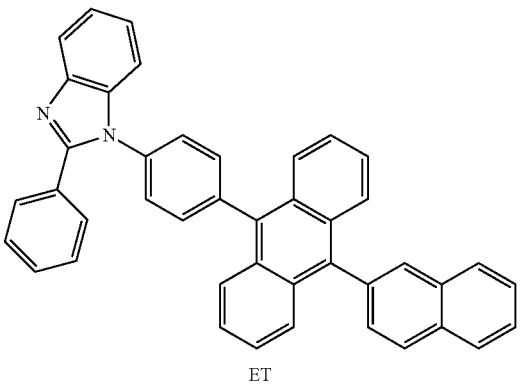

Ir(bzq)$_3$

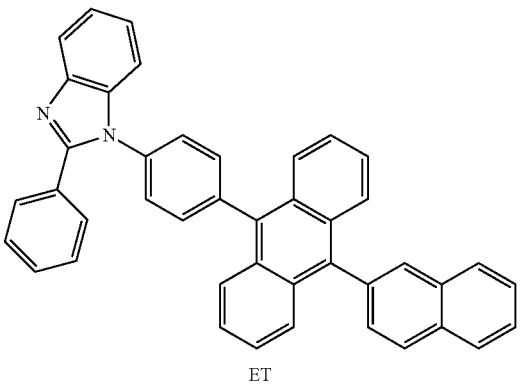

ET

-continued

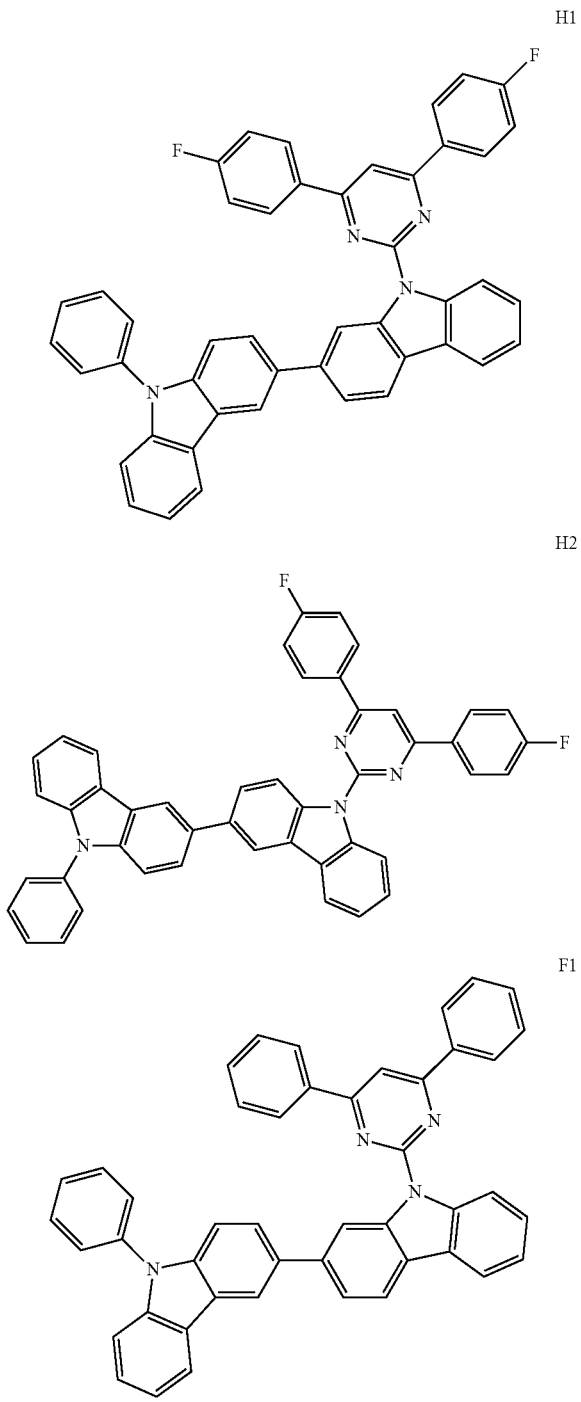

Example 2 and Comparative Example 1

Each organic EL device was produced in the same manner as in Example 1 except for forming the light emitting layer by using the compound H2 (Example 2) or the compound F1 (Comparative Example 1) in place of the host compound H1.

The results of the measurement of device performance made in the same manner as in Example 1 are shown in Table 1.

TABLE 1

| | Light emitting layer host material | 80% Lifetime (h) |
|---|---|---|
| Example 1 | Compound H1 | 500 |
| Example 2 | Compound H2 | 500 |
| Comparative Example 1 | Compound F1 | 350 |

As seen from Table 1, as compared with the organic EL device of Comparative Example 1 which employed the compound F1 having a similar central skeleton but having no substituent X at its terminal end, the organic EL devices of Examples 1 and 2, wherein each of the compounds H1 and H2 each having an azine ring substituted with the substituent X (—F) at the terminal end of the central skeleton comprising the carbazole derivative was used as the host material of the light emitting layer, had longer lifetimes.

INDUSTRIAL APPLICABILITY

As described above in detail, the material for organic EL device of the invention is useful as a material realizing an organic EL device with long lifetime.

REFERENCE NUMERALS

1: Organic electroluminescence device
2: Substrate
3: Anode
4: Cathode
5: Phosphorescent light emitting layer
6: Hole injecting/transporting layer
7: Electron injecting/transporting layer
10: Organic thin film layer (emission unit)

What is claimed is:
1. A material for organic electroluminescence device of formula (III):

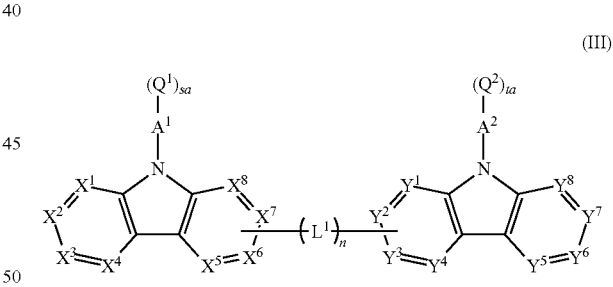

wherein:
each of $A^1$ and $A^2$ independently represents a single bond, a substituted or unsubstituted aromatic hydrocarbon group having 6 to 30 ring carbon atoms, or a substituted or unsubstituted heterocyclic group having 5 to 30 ring atoms;
each of $X^1$ to $X^8$ and $Y^1$ to $Y^8$ is $CR^a$;
$R^a$ represents a hydrogen atom;
$L^1$ represents a single bond;
n=0, and one of $X^5$ to $X^8$ is directly bonded to one of $Y^1$ to $Y^4$
each of sa and ta independently represents an integer of 0 to 5;
with the proviso that sa+ta is from 1 to 5;
when sa represents 1 to 5, $A^1$ is bonded to $Q^1$ of $(Q^1)_{sa}$;
when ta represents 1 to 5, $A^2$ is bonded to $Q^2$ of $(Q^2)_{ta}$;

when sa=0, $A^1$ represents a substituted or unsubstituted aromatic hydrocarbon group having 6 to 30 ring carbon atoms, or a substituted or unsubstituted heterocyclic group having 5 to 30 ring atoms;

when ta=0, $A^2$ represents a substituted or unsubstituted aromatic hydrocarbon group having 6 to 30 ring carbon atoms, or a substituted or unsubstituted heterocyclic group having 5 to 30 ring atoms;

each of $Q^1$ and $Q^2$ independently represents -Az-$W_q$;

q represents an integer of 1 to 4;

when two or more $Q^1$ groups exist, the $Q^1$ groups may be the same or different, and when two or more $Q^2$ groups exist, the $Q^2$ groups may be the same or different;

Az represents a q+1 valent residue of a ring represented by formula (Z):

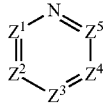

(Z)

wherein:

$Z^2$ is a nitrogen group, and $Z^1$, $Z^3$, $Z^4$ and $Z^5$ are each independently $CR^b$, wherein $R^b$ is as defined above with respect to $R^a$;

when two or more $R^b$ groups exist, the $R^b$ groups may be the same or different;

when two or more Az groups exist, the Az groups may be the same or different;

W is one selected from the group consisting of a non-fused aromatic hydrocarbon group having 6 to 15 ring carbon atoms substituted with a substituent X, a fused aromatic hydrocarbon group having 12 to 30 ring carbon atoms substituted with a substituent X, and a heterocyclic group having 5 to 30 ring atoms substituted with a substituent X, provided that the aromatic hydrocarbon group having 6 to 15 ring carbon atoms substituted with a substituent X, the fused aromatic hydrocarbon group having 12 to 30 ring carbon atoms substituted with a substituent X, and the heterocyclic group having 5 to 30 ring atoms substituted with a substituent X may optionally further comprise another substituent X;

the substituent X is F; and when two or more W groups exist, the W groups may be the same or different.

2. The material for organic electroluminescence device according to claim 1, wherein $X^7$ is bonded to $Y^3$.

3. The material for organic electroluminescence device according to claim 1, wherein $X^6$ is bonded to $Y^2$.

4. The material for organic electroluminescence device according to claim 1, wherein $X^6$ is bonded to $Y^3$.

5. The material for organic electroluminescence device according to claim 1, wherein Az represents a q+1 valent residue of a pyrimidine ring.

6. The material for organic electroluminescence device according to claim 1, wherein W is at least one of a phenyl group and a biphenyl group.

7. The material for organic electroluminescence device according to claim 1, wherein W is a phenylene group substituted with X, and Az and the substituent X are in a para-relationship.

8. The material for organic electroluminescence device according to claim 1, wherein W is selected from the group consisting of a naphthyl group, a phenanthrenyl group, a triphenylenyl group, a fluorenyl group, and a spirobifluorenyl group.

9. The material for organic electroluminescence device according to claim 1, wherein W is selected from a dibenzofuranyl group and a dibenzothiophenyl group.

10. The material for organic electroluminescence device according to claim 1, wherein W is a F-substituted phenyl group, a F-substituted biphenyl group, a F-substituted 9,9-dimethylfluorenyl group, a F-substituted dibenzofuranyl group, or a F-substituted dibenzothiophenyl group.

11. The material for organic electroluminescence device according to claim 1, wherein each of sa, and ta represents 0 or 1.

12. The material for organic electroluminescence device according to claim 1, wherein ta represents 0.

13. The material for organic electroluminescence device according to claim 1, wherein sa+ta represents 1.

14. The material for organic electroluminescence device according to claim 1, wherein q represents an integer of 2 to 4.

15. An organic electroluminescence device comprising one or more organic thin film layers between a cathode and an anode, wherein the organic thin film layers include a light emitting layer comprising the material for organic electroluminescence device according to claim 1.

16. The organic electroluminescence device according to claim 15, wherein the light emitting layer comprises the material for organic electroluminescence device.

17. The organic electroluminescence device according to claim 15, wherein the light emitting layer comprises a phosphorescent emitting material selected from an ortho-metallated complex of a metal selected from iridium (Ir), osmium (Os), and platinum (Pt).

18. The material for organic electroluminescence device according to claim 1, wherein $X^7$ is bonded to $Y^3$, $X^6$ is bonded to $Y^3$ or $X^6$ is bonded to $Y^2$.

19. The material for organic electroluminescence device according to claim 1, wherein $A^1$ represents a single bond, sa represents an integer of 1 to 5 and ta represents an integer of 0 to 5.

* * * * *